US010494422B2

(12) United States Patent
Wagner et al.

(10) Patent No.: US 10,494,422 B2
(45) Date of Patent: Dec. 3, 2019

(54) CCR5 DISRUPTION OF CELLS EXPRESSING ANTI-HIV CHIMERIC ANTIGEN RECEPTOR (CAR) DERIVED FROM BROADLY NEUTRALIZING ANTIBODIES

(71) Applicant: Seattle Children's Hospital, Seattle, WA (US)

(72) Inventors: Thor Wagner, Seattle, WA (US); Andrew M. Scharenberg, Seattle, WA (US); David J. Rawlings, Seattle, WA (US); Blythe Sather, Normandy Park, WA (US); Jaya Sahni, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

(21) Appl. No.: 15/306,643

(22) PCT Filed: Apr. 8, 2015

(86) PCT No.: PCT/US2015/024876
§ 371 (c)(1),
(2) Date: Oct. 25, 2016

(87) PCT Pub. No.: WO2015/167766
PCT Pub. Date: Nov. 5, 2015

(65) Prior Publication Data
US 2017/0044240 A1 Feb. 16, 2017

Related U.S. Application Data

(60) Provisional application No. 62/059,723, filed on Oct. 3, 2014, provisional application No. 61/985,947, filed on Apr. 29, 2014.

(51) Int. Cl.
| | | |
|---|---|---|
| *C07K 14/00* | (2006.01) | |
| *C07K 16/00* | (2006.01) | |
| *C12N 9/22* | (2006.01) | |
| *C07K 16/10* | (2006.01) | |
| *C12N 5/0783* | (2010.01) | |
| *C07K 14/725* | (2006.01) | |
| *C07K 14/705* | (2006.01) | |
| *C07K 14/715* | (2006.01) | |

(52) U.S. Cl.
CPC ...... *C07K 16/1054* (2013.01); *C07K 14/7051* (2013.01); *C07K 14/70517* (2013.01); *C07K 14/70578* (2013.01); *C07K 14/7158* (2013.01); *C12N 5/0636* (2013.01); *C12N 9/22* (2013.01); *C07K 2317/622* (2013.01); *C07K 2319/00* (2013.01); *C07K 2319/02* (2013.01); *C07K 2319/03* (2013.01); *C07K 2319/30* (2013.01); *C07K 2319/81* (2013.01); *C12N 2510/00* (2013.01)

(58) Field of Classification Search
CPC .............. C07K 14/00; C07K 14/70503; C07K 14/7051; C07K 14/70517; C07K 14/70578; C07K 16/00; C07K 16/1054; C07K 2317/00; C07K 2317/622; C07K 2319/00; C07K 2319/01; C07K 2319/02; C07K 2319/03; C07K 2319/035; C07K 2319/30; C07K 2319/81; C12N 5/0636; C12N 9/22; C12N 2510/00
See application file for complete search history.

(56) References Cited

U.S. PATENT DOCUMENTS

| | | | |
|---|---|---|---|
| 2008/0206264 A1* | 8/2008 | Anglister ............. | C07K 14/005 424/184.1 |
| 2009/0117097 A1 | 5/2009 | Igawa et al. | |
| 2011/0158957 A1* | 6/2011 | Bonini ..................... | C12N 9/22 424/93.7 |
| 2013/0287748 A1* | 10/2013 | June ........................ | A61K 35/17 424/93.21 |
| 2014/0120622 A1 | 5/2014 | Gregory et al. | |
| 2014/0205612 A1* | 7/2014 | Chan-Hui .......... | C07K 16/1063 424/148.1 |
| 2017/0015746 A1 | 1/2017 | Jensen | |
| 2017/0267739 A1* | 9/2017 | Berger ............. | C07K 14/70514 |
| 2018/0009891 A1 | 1/2018 | Jensen | |

FOREIGN PATENT DOCUMENTS

| | | |
|---|---|---|
| WO | WO 2013/055908 A1 | 4/2013 |
| WO | WO 2014/039523 A1 | 3/2014 |

OTHER PUBLICATIONS

Cartellieri et al, J. Biomed. Biotech. Article ID 956304, 13 pages, 2010.*
Patel et al, Gene Therapy 6: 412-419, 1999.*
Tebas, Pablo, et al. "Gene editing of CCR5 in autologous CD4 T cells of persons infected with HIV." *New England Journal of Medicine* 370.10 (2014): 901-910.
International Search Report dated Aug. 31, 2015, received in PCT/US2015/24876 filed Apr. 8, 2015.
International Preliminary Report on Patentability dated Nov. 1, 2016, received in PCT/US2015/24876 filed Apr. 8, 2015.
Lloyd et al., "Beyond the antigen receptor: editing the genome of T-cells for cancer adoptive cellular therapies," *Frontiers in Immunology*, Aug. 5, 2013, vol. 4, Art. 221, pp. 1-7.

(Continued)

*Primary Examiner* — Kevin K Hill
(74) *Attorney, Agent, or Firm* — Knobbe, Martens, Olson & Bear, LLP

(57) ABSTRACT

The present application generally relates to methods of genetically modifying a T-cell comprising a chimeric antigen receptor wherein the T-cell lacks a co-receptor for HIV. The application further relates to methods of making a nucleic acid encoding a chimeric antigen receptor, nucleic acids encoding a chimeric antigen receptor, and genetically modified T-cells comprising a chimeric antigen receptor disclosed herein. The application further relates to methods of treating, inhibiting, or ameliorating HIV in a subject including administering to the subject a cell disclosed herein.

26 Claims, 23 Drawing Sheets
Specification includes a Sequence Listing.

(56) References Cited

OTHER PUBLICATIONS

Lemaigre et al., "Transcriptional control of genes that regulate glycolysis and gluconeogenesis in adult liver," *Biochem J.*, Oct. 1, 1994, 303(Pt 1): 1-14.

Loeken, Mary R., "Effects of mutation of the CREB binding site of the somatostatin promoter on cyclic AMP responsiveness in CV-1 cells," *Gene Expression, The Journal of Liver Research*, (1993) vol. 3, No. 3, pp. 253-264.

McGehee, Jr. et al., "Differentiation-Specific Element: a cis-Acting Developmental Switch Required for the Sustained Transcriptional Expression of Angiotensinogen Gene During Hormonal-Induced Differentiation of 3T3-L1 Fibroblasts to Adipocytes," *Mol. Endo.* (1993) vol. 7, No. 4, pp. 551-560.

O'Reilly et al., "Identification of an Activating Transcription Factor (ATF) Binding Site in the Human Transforming Growth Factor-$\beta$2 Promoter," *The Journal of Biological Chemistry*, vol. 267, No. 28, Issue of Oct. 5, 1992, pp. 19938-19943.

Ye et al., "Characterization of a Silencer Regulatory Element in the Human Interferon-$\gamma$ Promoter," *The Journal of Biological Chemistry*, vol. 269, No. 41, Issue of Oct. 14, 1994, pp. 25728-25734.

Casucci et al., "Suicide Gene Therapy to Increase the Safety of Chimeric Antigen Receptor-Redirected T Lymphocytes," Journal of Cancer (2011) 2:378-382.

Maclean et al., "A novel real-time CTL assay to measure designer T-cell function against HIV Env+ cells," J Med Primatol (2014) 43:341-348.

\* cited by examiner

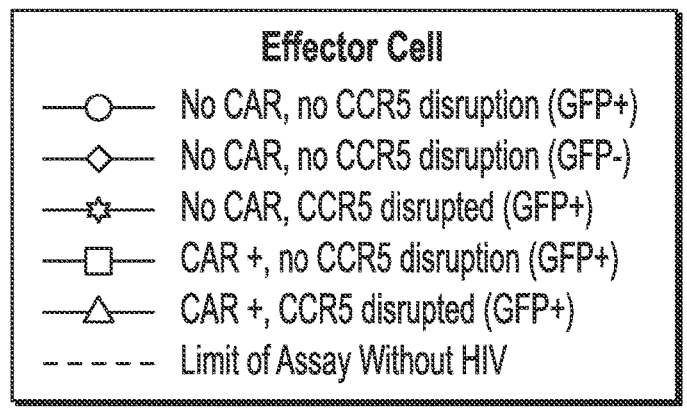
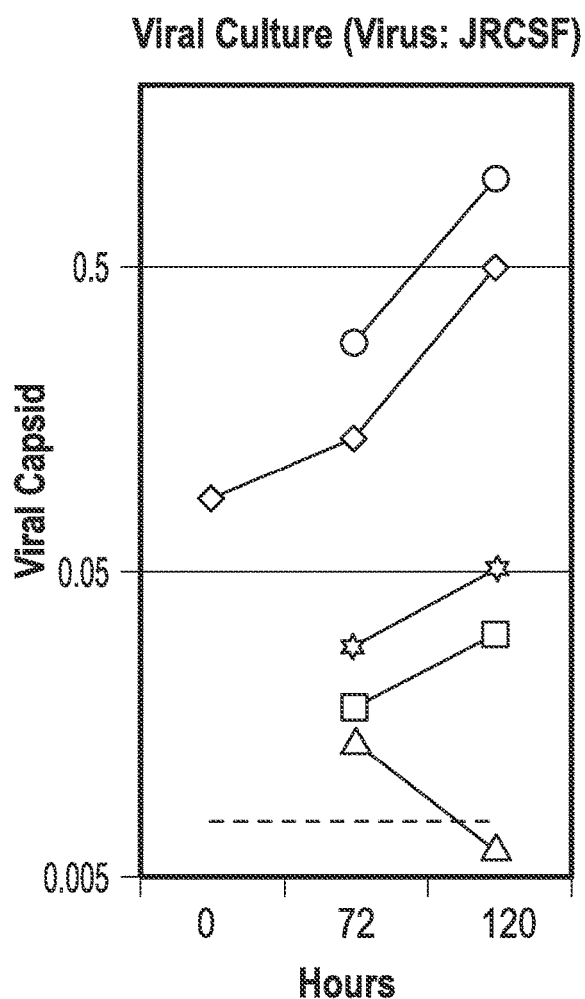
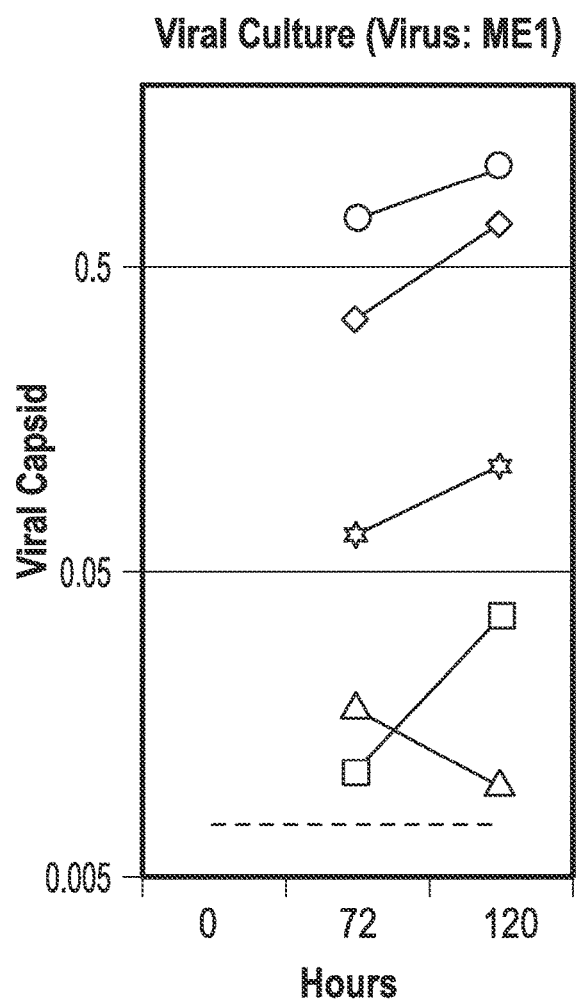
FIG. 4A
FIG. 4B

*representative of triplicates

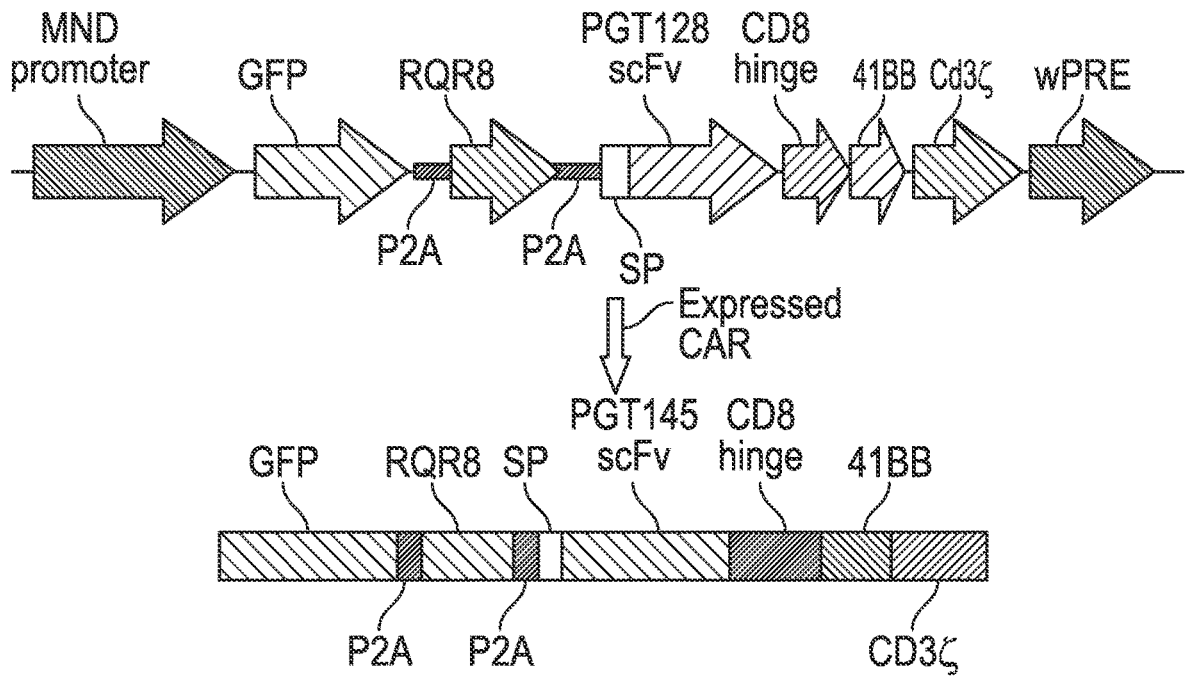

P2A= self cleaving 2a peptide from porcine teschovirus -1

T2A= self cleaving 2A peptide from Thosea asigna virus 2A

RQR8= Two rituximab binding epitopes flanking a single QBEnd10 epitope (monoclonal antibody in the Miltenyl CliniMACS CD34 selection system) on a CD8 stalk; small suicide/sort gene, can be detected by flow staining SP= signal peptide 41BB= CD137, activation-induced T-cell costimulatory molecule, signaling domain

FIG. 8-2

Data: Quantification of anti-CAR killing of HIV+cells
(mix CAR and HIV infected cells lines)

1. FLOW CYTOMETRY
Quantify the number of target cells (GFP(-) /cell tracker (+))
Among target cells, what percent take up live/dead stain eg. PG9 CAR + stimulated ACH (HIV+) cells 2. QUANTITATIVE PCR
Quantify the amount of HIV DNA in the cell culture
As CAR+ cells kill HIV infected cells there should be less HIV DNA Data: PGT145-based anti HIV CAR-Induced Killing of HIV-Infected Cells Median of triplicate wells at 72 hours (representative of two experiments)

Data: MND promoter seems to increase killing (but increased background)

Data: Dose Response (higher ratio CAR+ to HIV + cells lead to more killing)

CCR5 DISRUPTION OF CELLS EXPRESSING ANTI-HIV CHIMERIC ANTIGEN RECEPTOR (CAR) DERIVED FROM BROADLY NEUTRALIZING ANTIBODIES

CROSS-REFERENCED TO RELATED APPLICATIONS

The present application is a U.S. National Phase Application of PCT International Application Number PCT/US2015/024876, filed on Apr. 8, 2015, designating the United States of America and published in the English language, which claims the benefit of priority to U.S. Provisional Application Ser. No. 61/985,947, entitled "Anti-HIV Chimeric Antigen Receptor" filed Apr. 29, 2014, and U.S. Provisional Application Ser. No. 62/059,723, entitled "CCR5 Disruption of Cells Expressing Anti-HIV Chimeric Antigen Receptor (CAR) Derived from Broadly Neutralizing Antibodies" filed Oct. 3, 2014, the contents of which are hereby expressly incorporated by reference in their entirety.

STATEMENT REGARDING FEDERALLY SPONSORED R&D

The application presented herein was made with partial support under OPP104402, awarded by the Bill and Melinda Gates Foundation.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is Sequence Listing_SCRI.076WO.TXT, the date of creation of the ASCII text file is Mar. 17, 2015, and the size of the ASCII text file is 20 kb.

FIELD OF THE INVENTION

Aspects of the application described herein, include methods of treating, inhibiting and/or eliminating an HIV virus in a subject, as well as, methods to develop genetically modified t-cells comprising anti-HIV chimeric antigen receptors that can have binding domains for HIV-infected cells, such as HIV-infected t-cells, macrophages, microglial, and/or dendritic cells, wherein the genetically modified t-cells comprising anti-HIV chimeric antigen receptors have binding domains for HIV-infected cells and also lack a co-receptor for HIV. Included herein are also methods of inhibition and/or treatment of HIV by administering to a subject suffering from HIV, a genetically modified t-cell that lacks a co-receptor for HIV and expresses anti-HIV chimeric antigen receptors.

BACKGROUND

Human immunodeficiency virus (HIV) is a slowly replicating retrovirus, which leads to the progressive failure of the immune system allowing a subject infected with HIV to succumb to life-threatening infections and diseases. Despite drug intervention and prevention programs, 34 million people worldwide live with HIV. Currently, the standard treatment involves antiretroviral therapy (art), and therapy that target viral enzymes and in particular inhibition of the HIV replication cycle. Despite advances in medicine, there remains a need for additional approaches to inhibit and treat HIV.

SUMMARY

Some alternatives described herein relate to methods of genetically modifying a T-cell comprising a chimeric antigen receptor, wherein said T-cell lacks a co-receptor for HIV. Some such methods comprise delivering a nucleic acid sequence encoding a chimeric antigen receptor to a T-cell and disrupting a gene encoding a co-receptor for HIV in the T-cell. In some alternatives, the chimeric antigen receptor further comprises a signal peptide, an antigen-binding domain, a transmembrane CD8 hinge domain, a co-stimulatory domain, and/or an intracellular domain of a T-cell receptor. In some alternative, the antigen binding domain comprises a single chain variable fragment (scFv) domain from a high affinity broadly neutralizing antibody. In some alternatives, the high affinity broadly neutralizing antibody is an anti-HIV neutralizing antibody. In some alternatives, the anti-HIV neutralizing antibody comprises a sequence of PGT128 (SEQ ID NO: 1), PG9 (SEQ ID NO: 2), or PGT145 (SEQ ID NO: 3) or a binding fragment thereof the anti-HIV neutralizing antibody comprises a sequence of PGT145 (SEQ ID NO: 3) or a binding fragment thereof. In some alternatives, the co-stimulatory domain is CD137 (SEQ ID NO: 4). In some alternatives, the transmembrane CD8 hinge region is 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or within a range defined by any two of the aforementioned lengths. In some alternatives, wherein the co-stimulatory domain comprises a domain of CDζ and, wherein the domain of CDζ comprises an amino acid sequence of SEQ ID NO: 5. In some alternatives, the disrupting is performed by RNAi. In some alternatives, the disrupting is performed by a nuclease for targeted genome modification. In some alternatives, the nuclease is an engineered nuclease, a cleaving nuclease, a zinc finger nuclease, a transcription activator-like effector nuclease, meganuclease, a homing endonuclease, or a clustered regularly interspaced short palindromic repeat RNA guided nuclease, or a portion thereof. In some alternatives, the engineered nuclease comprises zinc fingers and, wherein the engineered nuclease comprises two, three, four, five, or six zinc fingers. In some alternatives, the engineered nuclease has a mutation enhancing activity. In some alternatives, the engineered nuclease further comprises a Fok1 nuclease, or a portion thereof. In some alternatives, the Fok1 nuclease is attached to the zinc fingers by a linker. In some alternatives, the linker is 4, 5, 6, 7, 8, 9, 10, 11, 12, 13, 14, or 15 amino acids in length or a length within a range defined by any two of the aforementioned lengths. In some alternatives, the zinc fingers are modified for enhanced binding. In some alternatives, the disrupting further comprises insertion of the nucleic acid into the gene. In some alternatives, the disrupting further comprises inserting the nucleic acid upstream from the gene. In some alternatives, the disrupting further comprises inserting the nucleic acid downstream from the gene. In some alternatives, the gene is a co-receptor gene. In some alternatives, the co-receptor is a co-receptor for viral entry. In some alternatives, the co-receptor is a co-receptor for HIV entry. In some alternatives, the co-receptor is CCR3, CXCR4 or CCR5. In some alternatives, the co-receptor is CCR5. In some alternatives, the cell is a CD4 or a CD8

T-cell. In some alternatives, delivering the nucleic acid sequence encoding a chimeric antigen receptor to the T-cell is performed by transduction with a lentiviral system. In some alternatives, the T cell is a precursor T cells. In some alternatives, the precursor T cell is a hematopoietic stem cell.

Some alternatives disclosed herein encompass a genetically modified T-cell. The genetically modified T-cell can comprise a chimeric antigen receptor, and wherein the genetically modified T-cell does not comprise a co-receptor for HIV or lacks at least one co-receptor for HIV. In some alternatives, the chimeric antigen receptor comprises a signal peptide, an antigen-binding domain, a transmembrane CD8 hinge domain, a co-stimulatory domain, and/or an intracellular domain of a T-cell receptor. In some alternatives, the antigen binding domain comprises a single chain variable fragment (scFv) domain from a high affinity broadly neutralizing antibody. In some alternatives, the high affinity broadly neutralizing antibody is an anti-HIV neutralizing antibody. In some alternatives, the anti-HIV neutralizing antibody comprises a sequence of PGT128 (SEQ ID NO: 1), PG9 (SEQ ID NO: 2), or PGT145 (SEQ ID NO: 3) or a binding fragment thereof. In some alternatives, the anti-HIV neutralizing antibody comprises a sequence of PGT145 (SEQ ID NO: 3) or a binding fragment thereof. In some alternatives, the co-stimulatory domain is CD137 (SEQ ID NO: 4). In some alternatives, the transmembrane CD8 hinge region is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the co-stimulatory domain comprises a domain of CDζ and, wherein the domain of CDζ comprises an amino acid sequence of SEQ ID NO: 5. In some alternatives, the co-receptor is a co-receptor for viral entry. In some alternatives, the co-receptor is a co-receptor for HIV entry. In some alternatives, the co-receptor is CCR3, CXCR4 and/or CCR5. In some alternatives, the co-receptor is CCR5. In some alternatives, the T cell is a precursor T cells. In some alternatives, the precursor T cell is a hematopoietic stem cell.

Some alternatives relate to methods of treating, inhibiting, or ameliorating HIV in a subject. Some methods comprise administering to the subject the genetically modified T-cell of any one of the alternatives described herein. In some alternatives, the subject is identified or selected to receive an anti-HIV therapy. In some alternatives, the method comprises monitoring or measuring the level or amount of HIV titer or a marker of HIV infection in said subject before, during, or after administration of the genetically modified T-cell of any one of the alternatives described herein. In some alternatives, the genetically modified T-cell is administered to said subject by adoptive cell transfer. In some alternatives, the subject is already receiving another form of anti-HIV therapy. In some alternatives, the anti-HIV therapy is administration of a fusion inhibitor, a nucleoside reverse transcriptase inhibitor, a non-nucleoside reverse transcriptase inhibitor, an integrase inhibitor, and/or a protease inhibitor or any combination thereof.

Some alternatives relate to methods of making chimeric antigen receptors that are specific for HIV antigens. Some such methods comprise providing nucleic acid sequence encoding a signal peptide, joining said nucleic acid sequence to a nucleic acid sequence encoding an antibody or binding sequence thereof (e.g., a sequence encoding a Fab fragment or a sequence encoding a CDR domain), attaching the nucleic acid encoding the antibody or binding sequence thereof to a nucleic acid encoding a transmembrane CD8 hinge, attaching the nucleic acid encoding the transmembrane CD8 hinge region gene sequence to a nucleic acid encoding a T-cell receptor co-stimulatory domain, attaching the nucleic acid encoding a T-cell receptor co-stimulatory domain to a nucleic acid encoding an intracellular domain of a T-cell receptor sequence and providing an enhancer (e.g., a nucleic acid encoding an enhancer sequence, for the chimeric antigen receptor gene sequence. In some alternatives, the antibody sequence or binding fragment thereof comprises a gene sequence encoding an HIV neutralizing antibody, or binding fragment thereof (e.g., a sequence encoding a Fab fragment or a sequence encoding a CDR domain). In some alternatives, the HIV neutralizing antibody or binding fragment thereof (e.g., a sequence encoding a Fab fragment or a sequence encoding a CDR domain) comprises an amino acid sequence of a domain of PGT128 (SEQ ID NO: 6), a domain of PG9 (SEQ ID NO: 7), or a domain of PGT145 (SEQ ID NO: 8). In some alternatives, the transmembrane CD8 hinge region comprises the full-length CD8 hinge region or a fragment thereof that is 10 to 69 amino acids in length (e.g., 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths). In some alternatives, the enhancer for the chimeric antigen receptor is codon optimized for expression in humans. In some alternatives, the codon optimization is performed by computational methods. In some alternatives, the co-stimulatory domain comprises a domain of CD137. In some alternatives, the domain of CD137 comprises the amino acid sequence of SEQ ID NO: 9. In some alternatives, the co-stimulatory domain comprises a domain of CDζ and, wherein the domain of CDζ comprises an amino acid sequence of SEQ ID NO: 10. In some alternatives, the antibody or binding fragment thereof is from a high affinity broadly neutralizing antibody that targets variable regions of HIV envelope. In some alternatives, the variable regions of HIV envelope are V1, V2, or V3. In some alternatives, the signal peptide comprises an amino acid sequence of SEQ ID NO: 11. In some alternatives, the transmembrane CD8 hinge region comprises an amino acid sequence of SEQ ID NO: 12.

Some alternatives encompass a chimeric antigen receptor. The chimeric antigen receptor can comprise a signal peptide, an antigen-binding domain, a transmembrane CD8 hinge domain, a co-stimulatory domain, and an intracellular domain of a T-cell receptor. In some alternatives, said antigen binding domain comprises a single chain variable fragments (scFv) from a high affinity broadly neutralizing antibody. Some alternatives also include a nucleic acid, such as an expression vector, preferably, an expression vector that is functional in human cells, comprising a nucleic acid that encodes said aforementioned chimeric antigen receptor, preferably, a nucleic acid that is codon-optimized for expression in humans. In some alternatives, the high affinity broadly neutralizing antibody is an anti-HIV neutralizing antibody. In some alternatives, the anti-HIV neutralizing antibody is comprised of amino acid sequences from PGT128 (SEQ ID NO: 6), PG9 (SEQ ID NO: 7), or PGT145 (SEQ ID NO: 8). In some alternatives, the co-stimulatory domain is CD137 (SEQ ID NO: 9). In some alternatives, the transmembrane CD8 hinge region comprises the full-length CD8 hinge region or a fragment thereof that is 10 to 69 amino acids in length (e.g., 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths). In some alternatives, the co-stimulatory domain comprises a domain of CDζ, wherein the domain of CDζ comprises an amino acid sequence of SEQ ID NO: 10. In some alternatives, the signal peptide comprises an amino acid sequence of SEQ ID NO: 11. In some alternatives, the transmembrane CD8 hinge region comprises an amino acid sequence of SEQ ID NO: 12.

More alternatives relate to methods of treating or inhibiting or ameliorating or eliminating HIV infection in a subject. Some methods comprise administering to a subject that has been identified or selected to receive an antiviral therapy, a chimeric antigen receptor expressing cell. In some alternatives, the subject that is identified or selected has HIV. In some alternatives, the chimeric antigen receptor comprises an antigen-binding domain, a transmembrane CD8 hinge domain, a co-stimulatory domain, and an intracellular domain of a T-cell receptor. In some alternatives, the antigen binding domain comprises a single chain variable fragment (scFv) from high affinity anti-HIV broadly neutralizing antibodies. In some alternatives, the anti-HIV neutralizing antibody is comprised of sequences from PGT128 (SEQ ID NO: 6), PG9 (SEQ ID NO: 7), or PGT145 (SEQ ID NO: 8). In some alternatives, the co-stimulatory domain is CD137 (SEQ ID NO: 9). In some alternatives, the transmembrane CD8 hinge region comprises the full-length CD8 hinge region or a fragment thereof that is 10 to 20 amino acids in length (e.g., 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths). In some alternatives, the co-stimulatory domain comprises a domain of CDζ wherein the domain of CDζ comprises an amino acid sequence of SEQ ID NO: 10. In some alternatives, the administering further comprises transferring of cells by adoptive cell transfer. In some of the aforementioned methods, the level or amount of HIV infection in said subject before, during, or after administration of anyone of the chimeric antigen receptors described herein is analyzed, monitored, or measured. The level or amount of HIV infection in said subject can be determined clinically and/or diagnostically, for example by detecting the presence of an HIV antigen or HIV nucleic acid in a biological sample obtained from the subject. In some alternatives, the subject is already receiving another form of anti-HIV therapy. Conventional kits for HIV analysis (e.g., a p24 detection kit or RT-PCR-based techniques can be employed).

Some alternatives disclosed herein relate to methods of making a nucleic acid encoding a chimeric antigen receptor. The methods include providing a nucleic acid sequence encoding a signal peptide, joining the nucleic acid sequence to a nucleic acid sequence encoding an antibody or binding fragment thereof, joining the nucleic acid sequence encoding the antibody or binding fragment to a nucleic acid encoding a transmembrane CD8 hinge region sequence, joining the nucleic acid encoding the transmembrane CD8 hinge region sequence to a nucleic acid encoding a T-cell receptor co-stimulatory domain gene sequence; and joining the nucleic acid encoding the T-cell receptor co-stimulatory domain gene sequence to a nucleic acid encoding an intracellular domain of a T-cell receptor sequence.

In some alternatives, the antibody or binding fragment thereof is an HIV neutralizing antibody or a binding fragment thereof. In some alternatives, the antibody or binding fragment thereof includes an amino acid sequence of a domain of PGT128 (SEQ ID NO: 6), a domain of PG9 (SEQ ID NO: 7), or a domain of PGT145 (SEQ ID NO: 8). In some alternatives, the transmembrane CD8 hinge region sequence is 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the nucleic acid or a portion thereof, for example the nucleic acid encoding the antibody or binding fragment thereof, the nucleic acid encoding the transmembrane CD8 hinge region sequence, the nucleic acid encoding a T-cell receptor co-stimulatory domain gene sequence, or the nucleic acid encoding an intracellular domain of a T-cell receptor sequence is codon optimized for expression in humans. In some alternatives, the codon optimization is performed by a computational method. In some alternatives, the co-stimulatory domain comprises a domain of CD137. In some alternatives, the domain of CD137 comprises the amino acid sequence of SEQ ID NO: 9. In some alternatives, the co-stimulatory domain comprises a domain of CDζ and wherein the domain of CDζ comprises an amino acid sequence of SEQ ID NO: 10. In some alternatives, nucleic acid sequence encoding an antibody or binding fragment thereof comprises or consists of a nucleic acid encoding a single chain variable fragments (scFv) from a high affinity broadly neutralizing antibody specific for HIV.

Some alternatives disclosed herein relate to nucleic acids encoding a chimeric antigen receptor including a signal peptide, an antigen-binding domain, a transmembrane CD8 hinge domain, a co-stimulatory domain, and an intracellular domain of a T-cell receptor. In some alternatives, the antigen binding domain includes a single chain variable fragment (scFv) from a high affinity broadly neutralizing antibody. In some alternatives, the high affinity broadly neutralizing antibody is an anti-HIV neutralizing antibody. In some alternatives, the anti-HIV neutralizing antibody includes a sequence of PGT128 (SEQ ID NO: 6), PG9 (SEQ ID NO: 7), or PGT145 (SEQ ID NO: 8) or a binding fragment thereof. In some alternatives, the co-stimulatory domain is CD137 (SEQ ID NO: 9). In some alternatives, the transmembrane CD8 hinge region is 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the co-stimulatory domain comprises a domain of CDζ, wherein the domain of CDζ comprises an amino acid sequence of SEQ ID NO: 10.

Some aspects and alternatives of the present disclosure relate to chimeric antigen receptors encoded by any one of the nucleic acids disclosed herein. Some aspects and alternatives of the present disclosure relate to cells including any one of the nucleic acids or chimeric antigen receptors disclosed herein.

Some alternatives disclosed herein relate to methods of treating, inhibiting, or ameliorating HIV in a subject including administering to the subject a cell that includes any one of the nucleic acids or chimeric antigen receptors disclosed herein. In some alternatives, the subject is identified or selected to receive an anti-HIV therapy. In some embodiments, the methods of treating, inhibiting, or ameliorating HIV in a subject disclosed herein further includes monitoring or measuring the level or amount of HIV titer or a marker of HIV infection in said subject before, during, or after administration of a cell that includes any one of the nucleic acids or chimeric antigen receptors disclosed herein. In some alternatives, the cell is administered to said subject by adoptive cell transfer. In some alternatives, the subject is already receiving another form of anti-HIV therapy. In some alternatives, the antibody or binding fragment thereof is from a high affinity broadly neutralizing antibody that targets variable regions of HIV envelope. In some alternatives, the variable regions of HIV envelope are V1, V2, and/or V3.

In some alternatives of the methods disclosed herein, the signal peptide comprises an amino acid sequence of SEQ ID NO: 11. In some alternatives, the transmembrane CD8 hinge region comprises an amino acid sequence of SEQ ID NO: 12. In some alternatives, the antigen-binding domain is from a high affinity broadly neutralizing antibody that targets variable regions of HIV envelope. In some alternatives, the variable regions of HIV envelope are V1, V2, and/or V3. In some alternatives, the signal peptide comprises an amino acid sequence of SEQ ID NO: 11. In some alternatives, the transmembrane CD8 hinge region comprises an amino acid sequence of SEQ ID NO: 12.

BRIEF DESCRIPTION OF THE DRAWINGS

FIG. 4 shows 2 graphs, panel A and B, illustrating the detectable amounts of viral protein (Viral capsid protein) over time after exposure of HIV infected cells to T-cells expressing $CAR^{145}$, T-cells expressing $CAR^{145}$ with a disrupted CCR5, and control cells lacking a $CAR^{PGT145}$ and/or lack CCR5 disruption. Two viral strains were tested, JRCSF and ME1. These experiments were performed in the absence of antiretrovirals.

DETAILED DESCRIPTION OF THE PREFERRED EMBODIMENT

Figure 1:
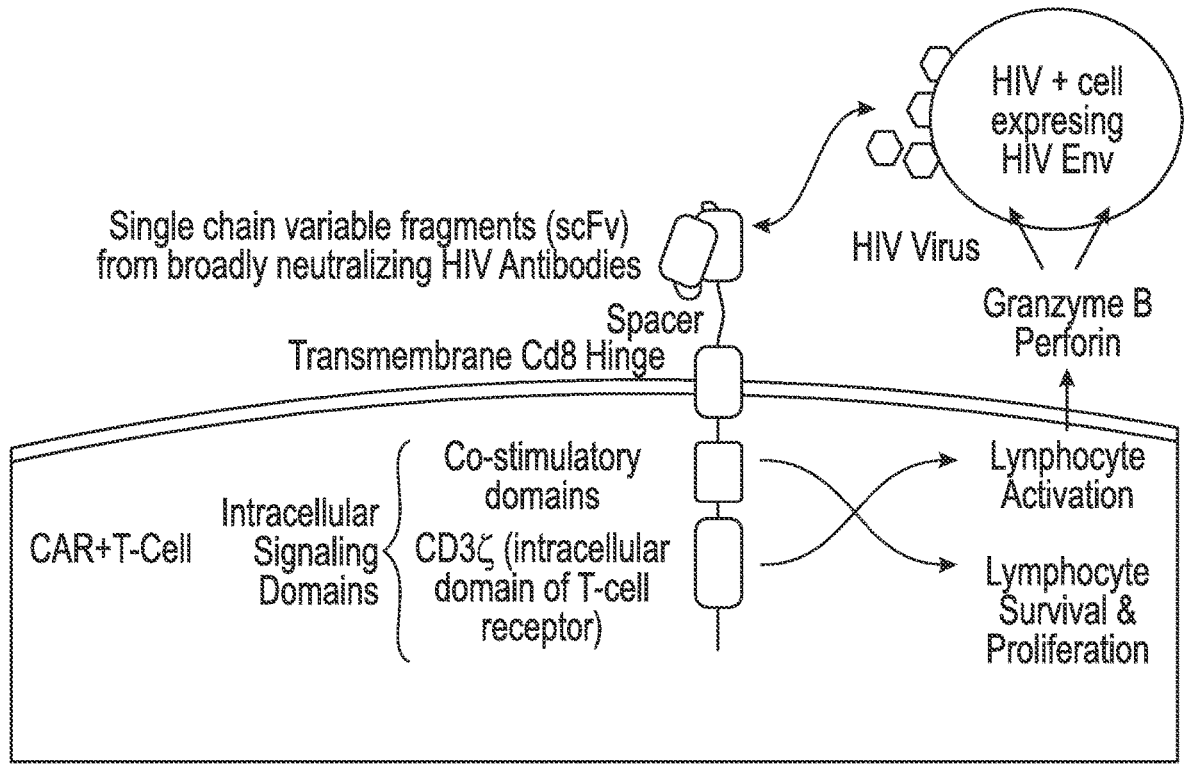
FIG. 1 illustrates a schematic of anti-HIV CAR interacting through a single chain variable fragment (scFv) domain with an HIV-infected cell expressing an HIV envelope and/or envelope proteins. In the schematic, the CAR comprises an intracellular domain that can comprise a co-stimulatory domain and an intracellular domain of a T-cell receptor. The extracellular portion comprises a transmembrane hinge and a scFv domain, which can bind to the HIV infected cell through interactions with an expressed protein on the surface. The anti-HIV CAR bearing cell also lacks or is engineered to lack a HIV co-receptor (CCR5), which prevents HIV infection of the anti-HIV CAR-expressing cell.

The following definitions are provided to facilitate understanding of the embodiments or alternatives of the invention.

As used herein, "a" or "an" can mean one or more than one.

As used herein, the term "about" indicates that a value includes the inherent variation of error for the method being employed to determine a value, or the variation that exists among experiments.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives described herein, a gene delivery polynucleotide for stable insertion of a nucleic acid into a gene is provided. "Oligonucleotide" can be used interchangeable with nucleic acid and can refer to DNA or RNA, either double stranded or a single stranded piece or DNA or RNA.

A "gene" is the molecular unit of heredity of a living organism, describing some stretches of deoxyribonucleic acids (DNA) and ribonucleic acids (RNA) that code for a polypeptide or for an RNA chain that has a function in the organism, and can be a locatable region in the genome of an organism. In some alternatives described herein, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, is provided.

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993); incorporated by reference in its entirety), cyclic AMP response elements (CREs), serum response elements (SREs; Treisman, Seminars in Cancer Biol. 1:47 (1990); incorporated by reference in its entirety), glucocorticoid response elements (GREs), and binding sites for other transcription factors, such as CRE/ATF (O'Reilly et al., J. Biol. Chem. 267:19938 (1992); incorporated by reference in its entirety), AP2 (Ye et al., J. Biol. Chem. 269:25728 (1994); incorporated by reference in its entirety), SP1, cAMP response element binding protein (CREB; Loeken, Gene Expr. 3:253 (1993); incorporated by reference in its entirety) and octamer factors (see, in general, Watson et al., eds., Molecular Biology of the Gene, 4th ed. (The Benjamin/Cummings Publishing Company, Inc. 1987; incorporated by reference in its entirety)), and Lemaigre and Rousseau, Biochem. J. 303:1 (1994); incorporated by reference in its entirety). As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives, a gene delivery polynucleotide is provided. In some alternatives, the gene delivery polynucleotide comprises a promoter sequence.

"Selectable marker cassette," is a gene introduced into a vector or a cell that confers a trait for artificial selection. A selectable marker cassette can be a screenable marker to allow a researcher to distinguish between wanted and unwanted cells, or to enrich for a specific cell type. In some alternatives, a gene delivery polynucleotide is provided. In some alternatives, the gene delivery polynucleotide comprises a selectable marker cassette.

A "protein" is a macromolecule comprising one or more polypeptide chains. A protein can also comprise non-peptide components, such as carbohydrate groups. Carbohydrates and other non-peptide substituents can be added to a protein by the cell in which the protein is produced, and will vary with the type of cell. Proteins are defined herein in terms of their amino acid backbone structures; substituents such as carbohydrate groups are generally not specified, but can be present nonetheless. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the gene delivery polynucleotide further comprises a sequence for at least one protein.

An "antibody" as described herein refers to a large Y-shape protein produced by plasma cells that is used by the immune system to identify and neutralize foreign objects such as bacteria and viruses. The antibody protein can comprise four polypeptide chains; two identical heavy chains and two identical light chains connected by disulfide bonds. Each chain is composed of structural domains called immunoglobulin domains. These domains can contain about 70-110 amino acids and are classified into different categories according to their size and function. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the gene delivery polynucleotide further comprises a sequence for at least one protein. In some alternatives, the gene delivery polynucleotide can comprise a sequence for an antibody or a portion thereof.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4$^-$CD8$^-$) cells. As they progress through their development, they become double-positive thymocytes (CD4$^+$CD8$^+$), and finally mature to single-positive (CD4$^+$CD8$^-$ or CD4$^-$CD8$^+$) thymocytes that are then released from the thymus to peripheral tissues.

About 98% of thymocytes die during the development processes in the thymus by failing either positive selection or negative selection, whereas the other 2% survive and leave the thymus to become mature immunocompetent T cells.

"Hematopoietic stem cells" or "HSC" as described herein, are precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M).

Chimeric Antigen Receptors

Chimeric antigen receptors (CAR), as described herein, are engineered protein receptors, which can confer specificity onto an immune effector cell. These receptors can be used to graft the specificity of a monoclonal antibody or binding fragment thereof onto a T-cell; with transfer of their coding sequence facilitated by retroviral vectors. CARs are genetically engineered T-cell receptors designed to redirect T-cells to target cells that express specific cell-surface antigens. Using a technique called adoptive cell transfer; T-cells can be removed from a subject and modified so that they can express receptors that can be specific for an antigen. The T-cells, which can then recognize and target an antigen, are reintroduced into the patient. In some alternatives, CAR expressing lymphocytes are described, wherein the CAR expressing lymphocyte can be delivered to a subject to target specific cells.

The structure of the CAR can comprise fusions of single-chain variable fragment (scFv) domains that are derived from monoclonal antibodies that are attached to transmembrane and cytoplasmic signaling domains. Most CARs can include an extracellular scFv domain that can be linked to an intracellular CD3ζ domain and can be designated as a first generation CAR. The CD3ζ can play a role in coupling antigen recognition to several intracellular signal-transduction pathways. However, linking the scFv domain to a co-stimulatory domain (e.g., CD137), can increase efficacy of treating using CAR expressing lymphocytes (second generation CAR). When T-cells express this molecule (often achieved by oncoretroviral vector transduction), they recognize and kill the target-cells that express a specific antigen targeted by the CAR. In some alternatives, the CARs comprise a scFv domain from high affinity binding antibodies including PG9, PGT128, and/or PGT145. In some alternatives, CARs can comprise a scFv domain from the high affinity binding antibody, PGT145 (see e.g., FIG. 1).

Enhancer domains, as described herein, also can refer to co-stimulatory domains of T-cell receptors. Enhancer domains of T-cell receptors can be located intracellularly and can control the type specific expression pattern of a T-cell receptor.

Upon binding recognition of the target antigen, the genetically engineered CAR can induce and/or effect or mediate cytolysis of the cell expressing the target antigen. Studies have shown that the effectiveness of the CAR approach can be observed in animal models, and clinical trials using CAR based genetically engineered T-lymphocytes for the treatment of subjects. Attention is directed to FIG. 1, illustrating the interaction of a CAR expressing lymphocyte with an infected cell. During exposure of CAR expressing T-cells to a virally infected cell, the scFv domains bind with high specificity to HIV infected cells expressing HIV envelop protein, such as T-cells and/or dendritic cells. Binding of the scFv domain triggers a translation of stimulatory responses to the intracellular stimulatory domains of the CAR, leading to the expression and secretion of molecules such as Perforin and Granzyme B, which effectively cause cell lysis and mediate apoptosis in target cells such as T-cells and/or dendritic cells.

In the present disclosure, the role of CAR has been extended to targeting T-cells to virally infected cells by genetically modifying T-cells to produce receptors that target viral proteins, preferably HIV antigens. In some alternatives, CAR expressing lymphocytes are described, wherein the CAR expressing lymphocyte can target HIV infected cells through an scFv comprising domains of PG9, PGT128 or PGT145. In some alternatives, CAR expressing lymphocytes are described, wherein the CAR expressing lymphocyte can cause killing of HIV infected T-cells.

The structure of a CAR comprises variable portions of an immunoglobulin heavy and light chain, and can, in some alternatives, be fused by a flexible linker to form a scFv domain. In some alternatives, the linker or spacer between the light and heavy chains can be 10 to 20 amino acids in length (e.g., at least, equal to 10, 11, 12, 13, 14, 15, 16, 17, 18, 19, or 20 amino acids or a length within a range defined by any two of the aforementioned lengths). The linker, which can also be referred to as a flexible spacer, allows the scFV domain to orient in multiple directions in order to enable an optimized antigen binding specificity. The scFv domain can be preceded by a signal peptide so as to direct the nascent protein to the endoplasmic reticulum and subsequent surface expression, whereby cleavage can occur. In some alternatives, a signal peptide precedes the scFv domain. A flexible spacer can also allow the scFv domain to orient in different directions to facilitate antigen binding. The transmembrane domain can, in some alternatives, be a typical hydrophobic alpha helix derived from the original molecule of the signaling endodomain, which protrudes into the cell and transmits the desired signal. A good spacer for allowing specific binding of the scFv domain can be determined empirically and is dependent on the scFv domain antigen recognition domain. In some alternatives, a linker is described, wherein the linker is an IgG1 hinge. In some alternatives, the linker comprises optimized spacer lengths so as to improve binding of scFv domain to the target cell, which may increase cytotoxic efficacy. In some alternatives, the linker or spacer between the scFv domain and the transmembrane can be 25 to 55 amino acids in length (e.g., at least, equal to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids or a length within a range defined by any two of the aforementioned lengths. In some alternatives, a linker that comprises the transmembrane region of CD8 or a portion thereof is provided.

Figure 2:
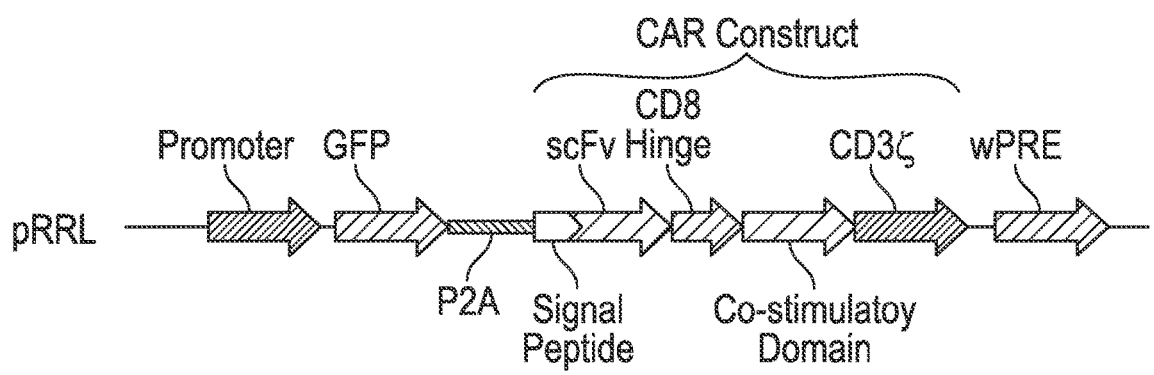
FIG. 2 shows an illustration of an anti-HIV CAR gene construct containing a gene for a GFP marker. As shown, the expressed CAR comprises a domain from the broadly neutralizing anti-HIV antibody, PGT145.
Figure 3:
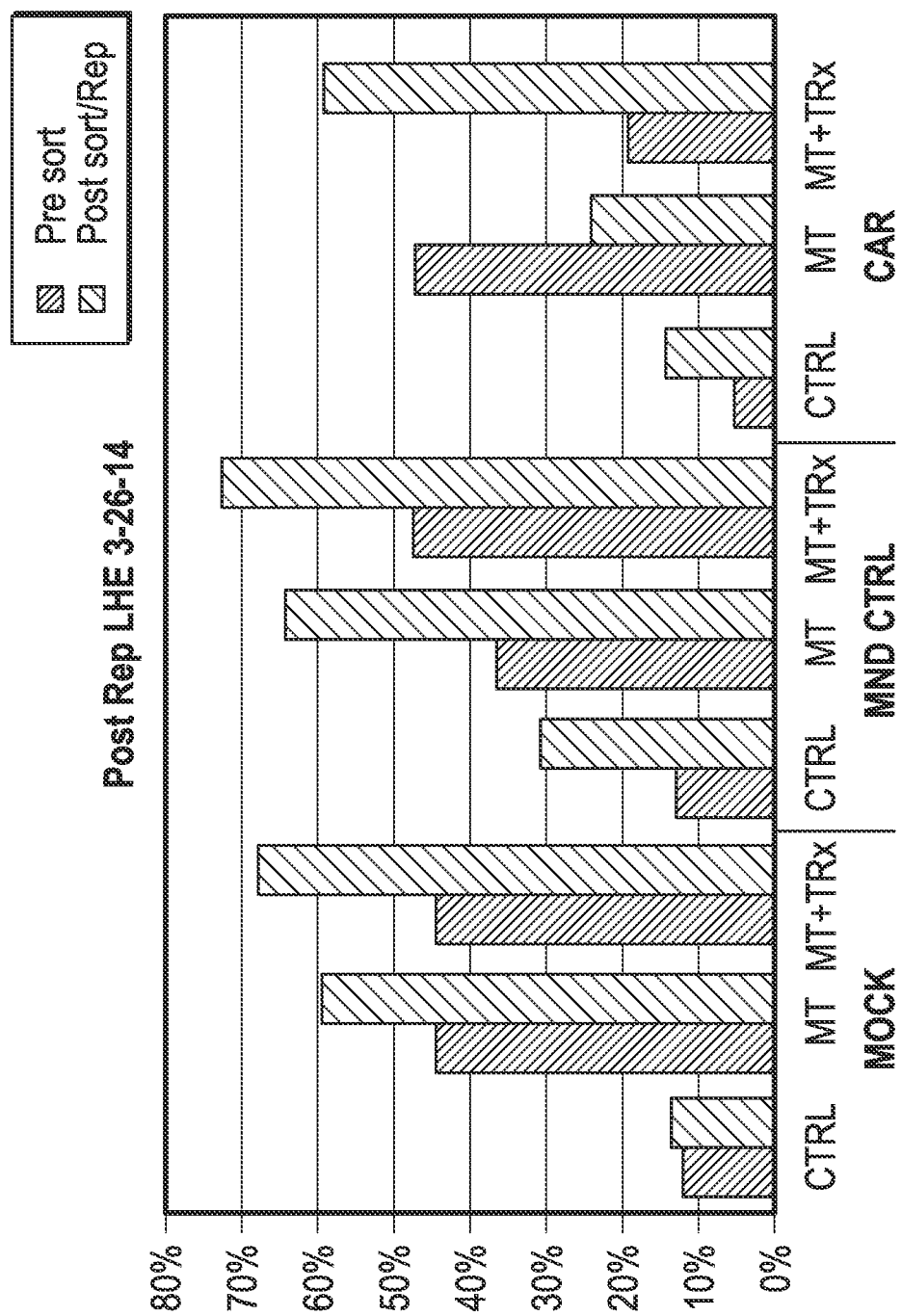
FIG. 3 shows a bar graph illustrating the results of CCR5 disruption in the CAR-expressing cells. For CCR5 disruption, three sets of cells were used: cells with no transduction (Mock), cells with a control GFP under the control of a MND promoter (MND CTRL), and cells carrying a $CAR^{PGT145}$ under the control of a MND promoter (CAR). The three types of cells were not targeted for CCR5 disruption (CTRL), were targeted for CCR5 disruption using a CCR5-specific megaTAL (MT), or were targeted for CCR5 disruption using a CCR5-specific megaTAL in conjunction with an end-processing nuclease (MT+Trx). The percentage of CCR5 disruption was evaluated by examining what percentage of the CCR5 gene can be disrupted in vitro using the CCR5-specific megaTAL.
Figure 5A:
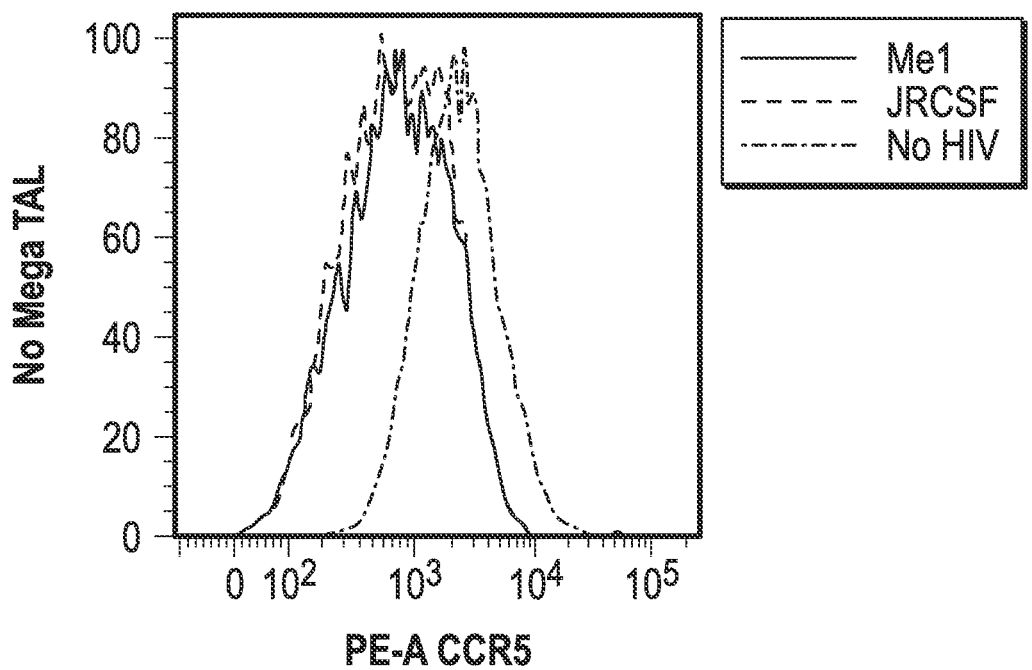
FIG. 5 shows panels A, B, C, and D illustrating fluorescence activating cell sorting (FACs) experiment that gated on cell surface CCR5 expression (using a CCR5 monoclonal antibody conjugated to PE) when grown in the presence of active HIV replication. Anti-HIV CAR+ T-cells that contain a single chain variable fragment (scFv) derived from PGT145 shown in FIG. 2 (panel B and D) and controls without CAR (panels A and C) were treated with (panel C and D) or without (panel A and B) the CCR5-specific megaTAL. Cells were grown in the presence of no HIV or two different HIV strain (JR-SCF or ME1). Panels A, B, C and D are histograms showing the mean fluorescence of CCR5 on CAR-expressing (as indicated by GFP) and CD4+ cells that appear alive based on the live/dead stain. In the absence of HIV there is comparable CCR5 expression by all cell types. In the presence of HIV replication, there is a decrease in CCR5 expression among CAR+ all cell types. However, in the presence of CCR5 disruption (panels C and D) there is much more enrichment for cells with low CCR5 expression, demonstrating that CCR5 has been disrupted.
Figure 5B:
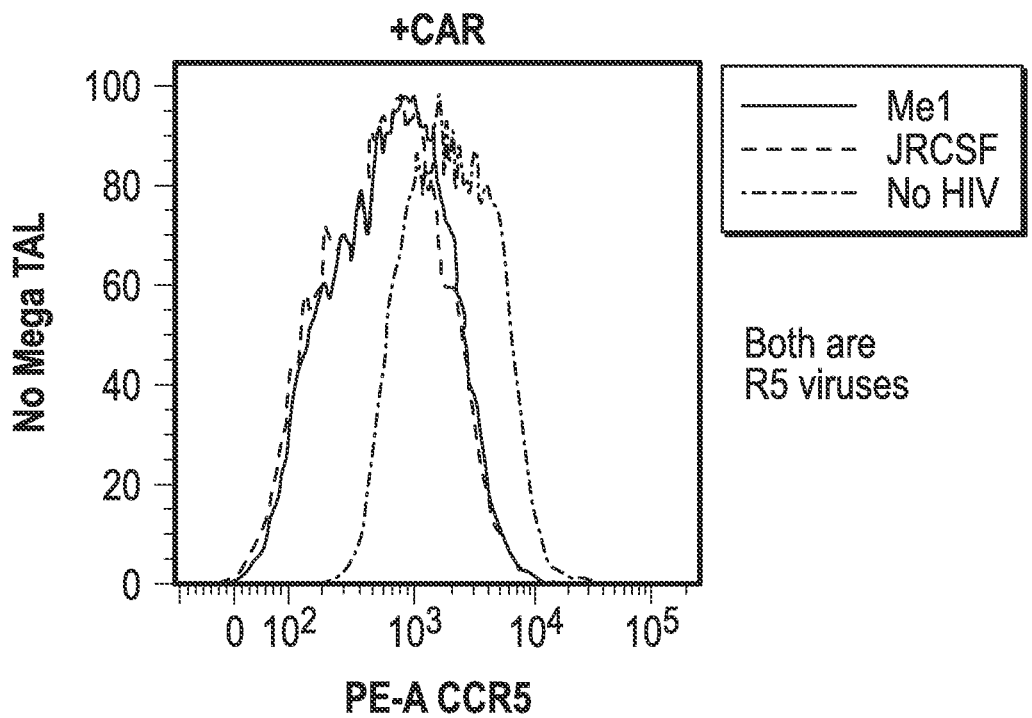
Figure 5C:
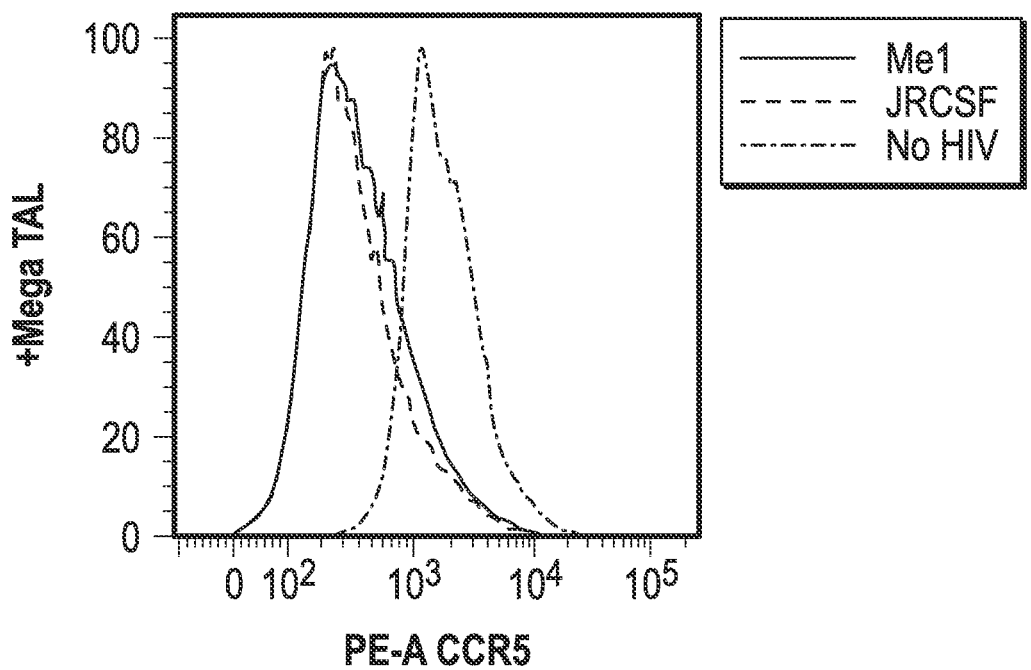
Figure 5D:
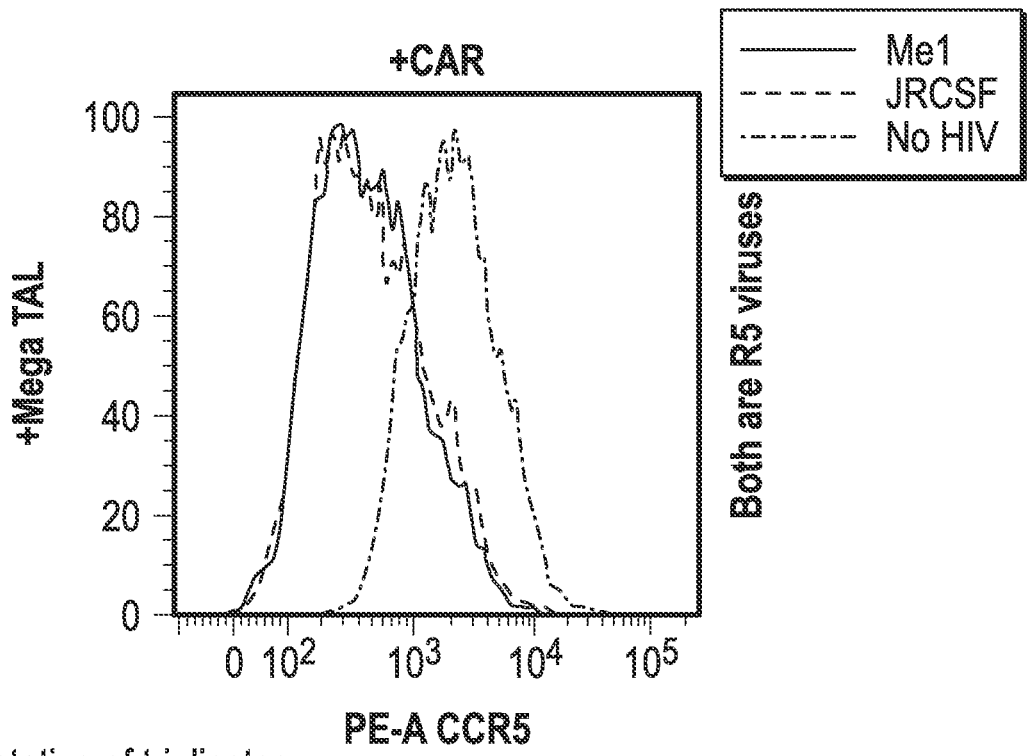
Figure 6A:
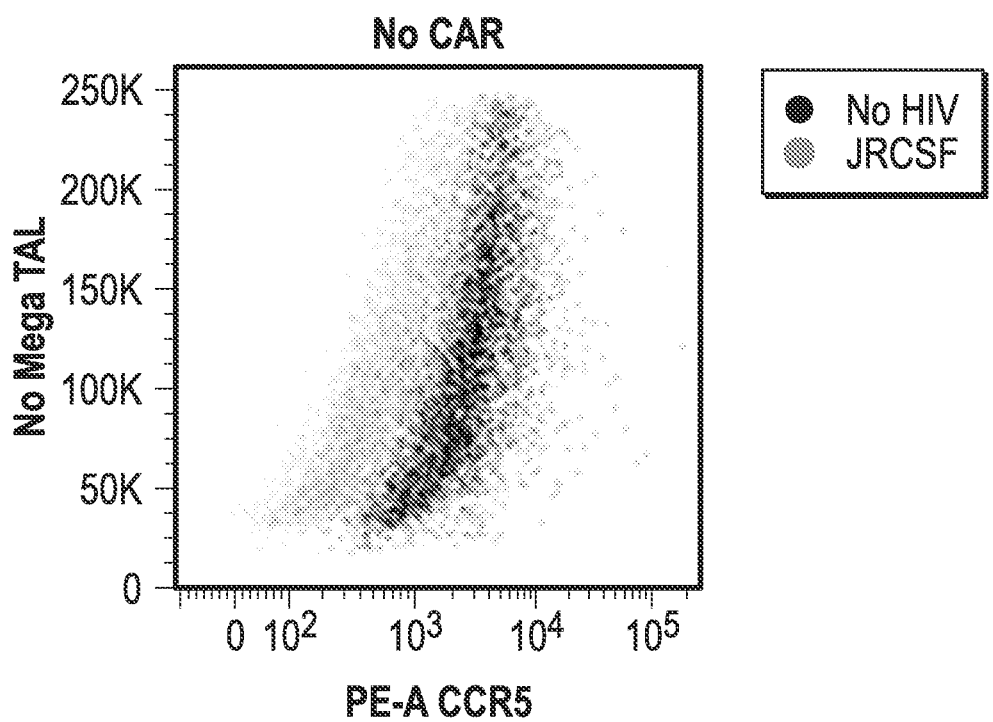
FIG. 6 shows a subset of the data from FIG. 5. The four graphs in panels A, B, C, and D, are arranged as in FIG. 5, wherein CAR-expressing cells (panel B and D) and cells with CCR5 disruption (panels C and D are gated on the live, CAR(GFP)+, live cells, and CCR5 cell-surface expression is plotted on the X-axis. Dot plots are shown of the cells in the presence of no HIV or the JR-CSF variant. Dot plots are shown instead of histograms as in FIG. 5 to provide more detail of the distribution than is available in the histograms in FIG. 5. The cells without CCR5 disruption (panels A and B) had reduced CCR5 expression compared to the cells treated with the CCR5 megaTAL to disrupt CCR5 (panels C and D). The more distinct two populations in Panels C and D than in panels A and B are noted, demonstrating CCR5 disruption. Specifically, panel D demonstrates a clear population of anti-HIV CAR containing cells that express reduced CCR5.
Figure 6B:
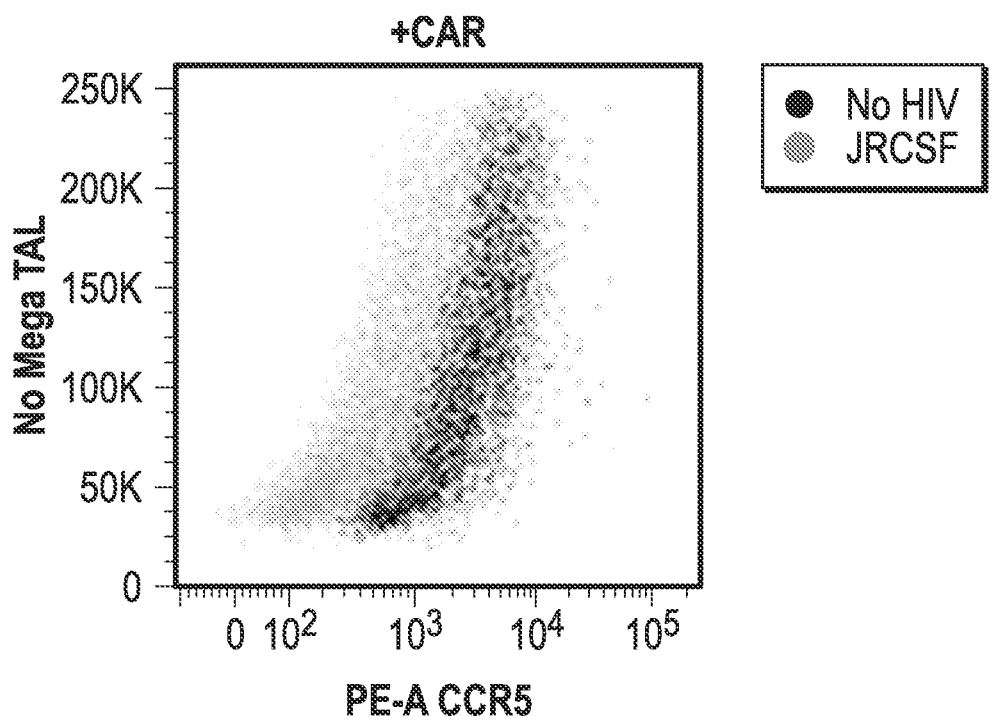
Figure 6C:
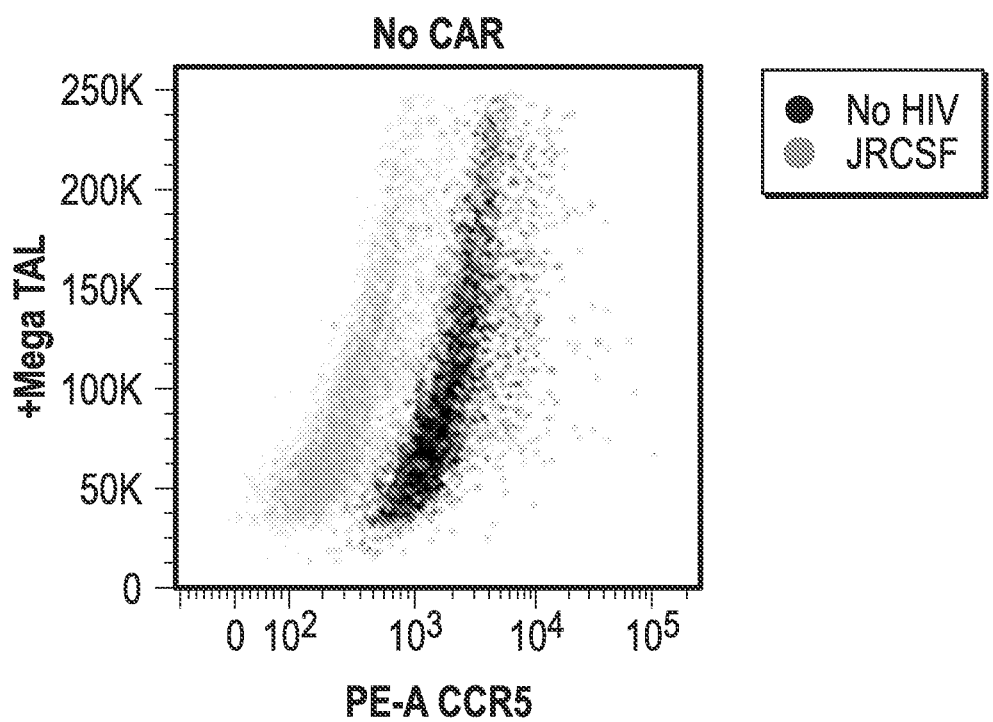
Figure 6D:
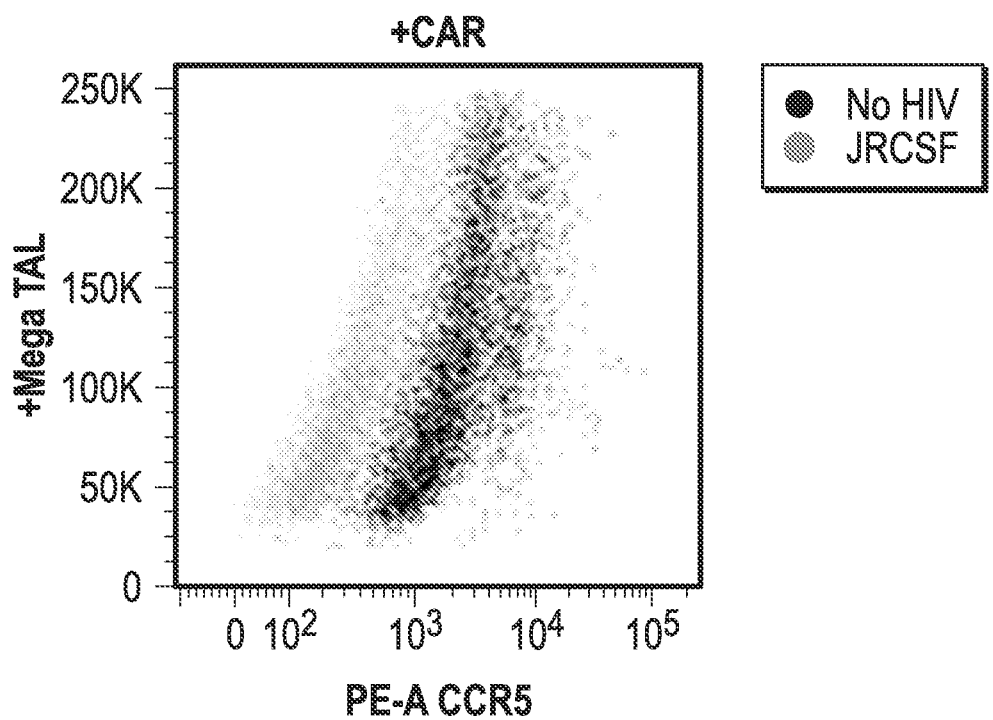

In an alternative shown in FIG. 2, a construct of an anti-HIV CAR was created as follows: Genes for a synthetic promoter that contains the U3 region of a modified MoMuLV LTR with myleoproliferative sarcoma virus enhancer (MND promoter; SEQ ID NO: 13), Green Fluorescent protein (GFP), PGT145, CD8 hinge region, CD137 co-stimulatory signaling domain, and CD3 were codon optimized for human expression using a commercially available algorithm. Gene constructs comprising these genes can then be commercially obtained through Integrated DNA Technologies, for example. To generate the CAR expressing T-cells, gene constructs containing the sequences for the CAR fusion protein were inserted into a backbone of a pRRL plasmid. Cells were then transduced with a lentivirus encoding anti-HIV CAR so as to generate a population of CAR expressing cells.

T-lymphocytes or T-cells, as referred to herein, are cells that can play a role in cell mediated immunity. There are several distinctions such as T-helper cells, cytotoxic T-cells, memory T-cells, Regulatory T-cells, Natural T-cells, Mucosal associated invariant T-cells, and Gamma delta T-cells. Microglial cells, as described herein, refer to a type of glial cell that are the resident macrophages of the brain and spinal cord, and can act as the first and main form of active immune defense in the central nervous system (CNS). Dendritic cells, as described herein, are antigen-presenting cells or accessory cells of the mammalian immune system. Their main function is to process antigen material and present it on the cell surface to the T cells of the immune system. They act as messengers between the innate and the adaptive immune systems.

Dendritic cells are present in tissues that are in contact with the external environment, (e.g. skin, inner lining of the nose, lungs, stomach and intestines) They can also be found in an immature state in the blood. Once activated, they migrate to the lymph nodes where they interact with T cells and B cells to initiate and shape the adaptive immune response.

In the present disclosure, the role of CAR has been extended by developing CARs that specifically direct T-cells to virally infected cells, such as T cells, macrophages, microglial, and/or dendritic cells. Such alternatives have been realized by genetically modifying T-cells to produce receptors that target viral proteins but, which lack HIV co-receptors. In some alternatives, the target viral proteins are HIV antigens. In some alternatives, CAR expressing lymphocytes are described, wherein the CAR expressing lymphocyte can target HIV infected cells, such as T cells and/or dendritic cells, through a scFv domain comprising domains of PG9, PGT128 or PGT145. In some alternatives, CAR expressing lymphocytes are described, wherein the CAR expressing lymphocyte can target HIV infected cells, such as T cells, macrophages, microglial and/or dendritic cells, through a scFv domain comprising domains of PGT145. In some alternatives, CAR expressing lymphocytes are described, wherein the CAR expressing lymphocytes induce or facilitate the killing of HIV infected cells, such as T-cells, macrophages, microglial, and/or dendritic cells, contribute to the reduction of HIV viral titer, and, therefore, ameliorate, inhibit, or treat HIV infection in a subject that receives a therapy utilizing said CARs.

Disclosed herein are methods for making a genetically modified T-cell comprising a CAR and lacking a co-receptor for HIV, and methods for developing CAR-expressing lymphocytes, wherein the CAR is designed to redirect T-cells to target-cells that express specific cell surface antigens, such as T-cells, macrophages, microglial and/or dendritic cells. Gene transcripts for CAR can be synthesized through standard molecular cloning techniques known to those skilled in the art and can be transduced into T-cells using a lentivirus encoding the CAR genetic transcript of interest. In some alternatives, the chimeric antigen receptor further comprises a signal peptide, an antigen-binding domain, a transmembrane CD8 hinge domain, a co-stimulatory domain, and/or an intracellular domain of a T-cell receptor. In some alternatives, the antigen binding domain comprises a single chain variable fragment (scFv) domain from a high affinity broadly neutralizing antibody. In some alternatives, the high affinity broadly neutralizing antibody is an anti-HIV neutralizing antibody. In some alternatives, the anti-HIV neutralizing antibody comprises a sequence of PGT128 (SEQ ID NO: 1), PG9 (SEQ ID NO: 2), or PGT145 (SEQ ID NO: 3) or a binding fragment thereof. In some alternatives, the anti-HIV neutralizing antibody comprises a sequence of PGT145 (SEQ ID NO: 3) or a binding fragment thereof. In some alternatives, the co-stimulatory domain is CD137 (SEQ ID NO: 4). In some alternatives, the CAR is an anti-HIV CAR comprising the CD8 linker region or a modified CD8 linker region of 10 to 69 amino acids in length (e.g., 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths). In some alternatives, the co-stimulatory domain comprises a domain of CDζ and, wherein the domain of CDζ comprises an amino acid sequence of SEQ ID NO: 5. In some alternatives, a signal peptide precedes the scFv domain.

T-Cell Co-Receptors for Viral Entry

A "co-receptor" as described herein, refers to a cell surface protein receptor that is bound to a plasma membrane surface of a cell. The co-receptor can bind to a biomolecule for cell signaling pathways and other cellular processes. Without being limiting, the biomolecule can be a ligand, a protein, a nucleic acid, or a signaling molecule that can initiate a biological process such as entry of a bacterial or a viral pathogen into the host cell.

CCR family receptors are G-protein coupled receptors (GPCRs) that can function as a chemokine receptor. CCR receptors are expressed in neuronal cells, such as dendrites and microglia, and are mainly found on immunological cells, such as T-cells. CCR receptors are integral membrane proteins that respond to the cytokines of the CC chemokine family. To date there are ten documented members of the CC chemokine receptor subfamily, which are named CCR1 to CCR10. Structural and functional similarities can be found among the family members as many can bind the same chemokines. CCR family receptors can also function as a cellular co-receptor.

CCR5 is expressed on several cell types and includes peripheral blood derived dendritic cells, CD34+ hematopoietic progenitor cells, and activated/memory Th1 lymphocytes. CCR5 is implicated in susceptibility to HIV-1 infection and disease, and acts as a primary co-receptor for HIV-1. However, CCR5 is not the only member of the CCR family that can facilitate HIV entry and infection. CCR5 has structural similarities to other proteins of the CCR family in structure and in ligand binding, in which the similar ligand binding can be due to conserved structural domains in the family. As such, CCR2b, CCR3, and CCR8 can be utilized by some HIV strains as co-receptors for viral entry.

CCR5 and CXCR4 are structurally related chemokine receptors. CCR5 is of interest as CCR5-deficient (CCR5−/−) *Homo sapiens* are highly resistant to HIV infection. This lack of CCR5 expression is caused by a naturally occurring 32 base pair deletion in the CCR5 gene. Previous studies have indicated that HIV resistance in CCR5Δ32 homozygotes can be from the result of the loss of CCR5 on the cell surface, as well as, the active down-regulation of CXCR4 expression by the mutant CCR5Δ32 protein.

CXCR4 was originally identified as an orphan receptor, and later gained attention when it was isolated as a co-receptor for HIV-1. CXCR4 is expressed on the cell surface of various cancer cells and plays a role in cell proliferation and migration of cancer cells.

As HIV co-receptors, CCR5 and CXCR4 can physically associate with a protein on the cell surface of HIV infected cells, GP120. HIV fusion is initiated by sequential receptor binding of GP120, first binding to CD4 and then to a specific chemokine receptor, which can be CCR5 or CXCR4. These events preclude the fusion that can occur during infection of the T-cell.

CCR3, another chemokine receptor of the G-protein coupled receptors family, has also been shown to exhibit activity as a co-receptor for HIV-1 entry. Recombinant CCR3 has been shown to interact with various HIV-1 isolates that include dual-tropic and some M-tropic strains. Several M-tropic HIV-1 strains were shown to use endogenous CCR3 for infection of microglial cells in vitro. CCR3 is strongly expressed on primary eosinophils, and importantly for HIV infections, has been shown to be expressed on a small subset of T-cells. CCR2b, another chemokine receptor of the G-protein coupled receptors family, has also been shown to exhibit activity as an entry co-factor for T- and M-tropic virus strains of HIV.

As evidenced by their roles in HIV infection, mutations or knockouts to the genes expressing CCR family receptors that are HIV co-receptors, can prevent or protect cells from HIV infection. In conjunction with T-cells displaying CARs on the cell surface, disruption of co-receptors can prevent CAR displaying T-cells from susceptibility to HIV infections, thereby depleting the HIV reservoir in the subject and can have a therapeutic benefit for HIV infected individuals. Disclosed herein are methods for making a genetically modified T-cell comprising a CAR and lacking a co-receptor for HIV, and methods for developing CAR-expressing lymphocytes, wherein the CAR is designed to redirect T-cells to target-cells that express specific cell surface antigens, such as HIV-infected T cells and/or dendritic cells. In some alternatives, a method of genetically modifying a T-cell comprising a chimeric antigen receptor, wherein said T-cell lacks a co-receptor for HIV is provided. The method can comprise delivering a nucleic acid sequence encoding a chimeric antigen receptor to a T-cell and disrupting a gene encoding a co-receptor for HIV in the T-cell. In some alternatives, the disrupting is performed by RNAi. In some alternatives, the disrupting is performed by a nuclease for targeted genome modification. In some alternatives, the gene that is mutated, knocked out, or removed is a co-receptor gene. In some alternatives, the co-receptor that is mutated, knocked out, or removed is a co-receptor for viral entry. In some alternatives, the co-receptor that is mutated, knocked out, or removed is a co-receptor for HIV entry. In some alternatives, the co-receptor that is mutated, knocked out, or removed is CCR2b, CCR3, CXCR4 and/or CCR5. In some alternatives, the co-receptor that is mutated, knocked out, or removed is CCR3, CXCR4 and/or CCR5. In some alternatives, the co-receptor that is mutated, knocked out, or removed is CCR5.

Cells that can be genetically modified to comprise an anti-HIV CAR and lack a co-receptor for HIV are contemplated. As described herein, "CD4$^+$ T-cells" are mature T helper-cells that play a role in the adaptive immune system. HIV can target CD4$^+$ cells, such as macrophages, dendritic cells, and CD4$^+$ T cells. HIV-1 can use CD4 to gain entry into host T-cells by binding through its viral envelope protein GP120. Binding to CD4 causes a conformational change in GP120 allowing the viral protein GP41, to insert into the host cell, allowing the outer membrane of the virus to fuse with the cell membrane. As such, HIV infection can lead to a progressive decline in the number of T cells expressing CD4.

As described herein, "CD8 T-cells" or "killer T-cells" are T-lymphocytes that can kill cancer cells, cells that are infected with viruses or cells that are damages. CD8 T-cells recognize specific antigens, or a protein that is capable of stimulating an immune response and is produced by cancer cells or viruses. If the T-cell receptor of the CD8 T– cell recognizes the antigen, the CD8 T-cell can bind to the presented antigen and destroy the cell. During the early ages of HIV infection, CD8 T cells can multiply rapidly and are generally able to kill cells that are infected with the HIV virus. While most of these T-cells can die within the course of the infection, "memory T-cells" can be left behind. In most viral infections, the memory T-cells can respond when the invading virus returns, however with HIV, the CD8 response decreases over time and HIV replication cannot be controlled. It is well documented that CD8 T– cells are not natural hosts for HIV infections. However, CD8 T-cells expressing anti-HIV CAR can be a potential target for HIV viral infection, as anti-HIV CAR allows contact of HIV infected cells with the CD8 T-cells expressing anti-HIV CAR through interaction with the scFv domain. Therefore, knocking down CCR5 in anti-HIV expressing CD8 T-cells would be crucial in preventing HIV infection of the CD8 T-cell.

In some alternatives, the T-cell is a CD4 T-cell. In some alternatives, the T-cell is a CD8 T-cell. In some alternatives, the delivering of the nucleic acid sequence encoding a chimeric antigen receptor to the T-cell is performed by transduction with a lentiviral system.

Gene Knock-Down

Gene knock down can refer to techniques in which expression of one or more of an organisms genes are reduced. Gene knock down can occur through genetic modification, treatment with a reagent, and other methods known to those skilled in the art. Genetic knock down can occur using a reagent. By way of example and not of limitation reagents for genetic knock down can be short DNA or RNA oligonucleotides that are complimentary to the gene or mRNA transcript that are intended to be knocked down.

"RNA interference" as described herein, refers to a means of silencing genes by way of mRNA degradation. RNA is often the choice used to silence gene expression in somatic cells and lentivirus mediated RNAi is also used for sustained and efficient silencing. Genetic knockdown is achieved by introducing small double stranded interfering RNAs (siRNA) into the cytoplasm. Lentiviral RNAi systems express short hairpin RNAs (shRNA) from RNApol III promoters which can drive high levels of transcription using initiation and termination sites. However, a problem with lentiviral mediated RNAi is the constant generation of shRNAs which can interfere with endogenous miRNA biogenesis and result in the deregulation of gene expression. Once the siRNAs are introduced into the cell, they are processed by the RNA-induced silencing complex (RISC). siRNA is complementary to the target mRNA to be silenced, and the RISC uses the siRNA as a template for locating the target mRNA for degradation, thus preventing translation of a protein. After RISC localizes to the target mRNA, the RNA is degraded by the ribonuclease.

Knocking down a gene can also be performed by targeted genome modification, which is a tool for altering gene expression. Targeted genome modification can also be referred to as genome editing, or genome editing with engineered nucleases. Targeted genome modification can comprise a specific type of genetic engineering in which nucleic acid is inserted, replaced or removed from a genome using an artificially engineered nuclease or nucleases. The nucleases perform by introducing specific double stranded breaks at the desired locations in a genome and harness the cells mechanisms of repair to repair the induced break by homologous recombination and nonhomologous end-joining mechanism. Several engineered nucleases can be used. By way of example and not of limitation, nucleases can include zinc finger nucleases (ZFNs), Transcription Activator-like Effector Nucleases (TALENs), the CRISPR/Cas system, RNA guided endonucleases and/or engineered meganuclease re-engineered homing endonucleases.

Targeted gene disruption has wide applicability for research, therapeutic, agricultural, and industrial uses. One strategy for producing targeted gene disruption is through the generation of double-strand DNA breaks caused by site-specific endonucleases. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

The term "endonuclease" refers to enzymes that cleave the phosphodiester bond within a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An endonuclease may cut a polynucleotide symmetrically, leaving "blunt" ends, or in positions that are not directly opposing, creating overhangs, which may be referred to as "sticky ends." The methods and compositions described herein may be applied to cleavage sites generated by endonucleases.

Transcription activator-like effector nucleases (TALENS) are artificial restriction enzymes generated by fusing a Tal effector DNA binding domain to a DNA cleavage domain. Tal effectors are bacterial DNA-binding proteins consisting of highly homologous 34 amino-acid modules that can bind one nucleotide with high affinity. The variable twelfth and thirteenth amino acids of the TALENS module referred to as repeat-variable di-nucleotide, confers base specificity (i.e., NN→G/A, NI→A, NG→T, NK→G, HD→C, and NS→A/T/C/G) and TALEN arrays that can target a nucleotide sequence can be generated by assembling the individual modules. The relationship between the amino acid sequence and the DNA recognition has allowed engineering of specific DNA binding domains by the selecting of a combination of the repeat segments contacting the correlating Repeat Variable Diresidue (RVDs). TALENS can be used to edit genomes by inducing double-strand breaks (DSB) in the cells of interest, and in which the cells can respond with several types of repair mechanisms.

Zinc finger proteins (ZFP) are eukaryotic DNA binding proteins. The most common ZFP motifs for genome editing, for example, are the Cys2-His2 fingers, and each type are specific for a nucleotide triplet. Artificial ZFP domains can be generated to target specific DNA sequences that are usually 9-18nt long by the assembly of individual zinc fingers. The term "Designer zinc finger proteins," refers to zinc finger proteins with purposefully re-engineered DNA-binding specificities that can provide a broadly applicable technology for targeting functional domains to almost any gene of interest in many types of cells. Zinc finger nucleases (ZFNs) are a powerful tool for performing targeted genomic manipulation in a variety of cell types in humans. ZFNs consist of an engineered DNA-binding zinc finger domain linked to a non-specific endonuclease domain and can introduce double-stranded breaks (DSBs) that stimulate both homologous and non-homologous recombination, which can then be harnessed to perform genomic manipulation. As such, ZFPs have potential in both research and gene therapy applications.

Clustered Regularly Interspaced Short Palindromic Repeats (CRISPR) comprise a DNA loci that can contain short repetitions of base sequences, in which each repetition is followed by short segments of spacer DNA from viral exposure. The CRISPR regions can be associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. As a genome editing mechanism, an RNA guided endonuclease, a Cas protein, and appropriate guide RNA can be delivered into a cell and the organisms' genome can be cut at a desired location. CRISPRS are an efficient mechanism for targeting/modifying genes and the mechanism is known to those skilled in the art.

Another nuclease known to those skilled in the art, is the FokI nuclease. FokI is naturally found in *Flavobacterium okeanokoites*, and is a bacterial type IIS restriction endonuclease consisting of an N-terminal DNA-binding domain and a non-specific DNA cleavage domain at the C-terminal. When Fok1 is bound to duplex DNA via its DNA-binding domain at the 5'-GGATG-3':3'-CATCC-5' recognition site, the DNA cleavage domain is activated and cleaves, without further sequence specificity, the first strand 9 nucleotides downstream and the second strand 13 nucleotides upstream of the nearest nucleotide of the recognition site.

An engineered nuclease such as a "MegaTal" nuclease can also be used for targeting and modifying a gene of interest. A MegaTal, as described herein, refers a hybrid nuclease architecture which combines the engineerability of a TAL effector with the cleavage sequence specificity of a meganuclease (mn) cleavage domain. The architecture of the MegaTal allows the generation of active and specific nucleases that are compatible with viral and nonviral cell delivery methods.

Disclosed herein are methods for making a genetically modified T-cell comprising a CAR and lacking a co-receptor for HIV, and methods for developing CAR-expressing lymphocytes, wherein the CAR is designed to redirect T-cells to target-cells that express specific cell surface antigens, such as HIV-infected T cells, macrophages, microglial and/or dendritic cells. In some alternatives, a method of genetically modifying a T-cell comprising a chimeric antigen receptor, wherein said T-cell lacks a co-receptor for HIV is provided. The method can comprise delivering a nucleic acid sequence encoding a chimeric antigen receptor to a T-cell and disrupting a gene encoding a co-receptor for HIV in the T-cell. In some alternatives, the disrupting, inhibition, or gene knockdown is performed by RNAi. In some alternatives, the disrupting, inhibition, or gene knockdown is performed by a nuclease for targeted genome modification. In some alternatives, the nuclease used for disrupting, inhibition, or gene knockdown is a zinc finger nuclease, Transcription Activator-like Effector Nuclease, a nuclease from a CRISPR/Cas system, an RNA guided endonucleases, or an engineered meganuclease re-engineered homing endonucleases. In some alternatives, the nuclease used for disrupting, inhibition, or gene knockdown is an engineered nuclease, a cleaving nuclease, a zinc finger nuclease, a transcription activator-like effector nuclease, meganuclease, a homing endonuclease, or a clustered regularly interspaced short palindromic repeat RNA guided nuclease, or a portion thereof. In some alternatives, the engineered nuclease comprises a TAL effector with the cleavage sequence specificity of a meganuclease (mn) cleavage domain. In some alternatives, the engineered nuclease used for disrupting, inhibition, or gene knockdown comprises a MegaTal. In some alternatives, the engineered nuclease used for disrupting, inhibition, or gene knockdown comprises zinc fingers and, wherein the engineered nuclease comprises two, three, four, five, or six zinc fingers. In some alternatives, the engineered nuclease used for disrupting, inhibition, or gene knockdown has a mutation enhancing activity. In some alternatives, the engineered nuclease used for disrupting, inhibition, or gene knockdown further comprises a Fok1 nuclease, or a portion thereof. In some alternatives, the Fok1 nuclease used for disrupting, inhibition, or gene knockdown is attached to the zinc fingers by a linker. In some alternatives, the linker is 4, 5, 6, 7, 8, 9, 10, 11, 12, 13, 14, or 15 amino acids in length or a length within a range defined by any two of the aforementioned lengths. In some alternatives, the zinc fingers used for disrupting, inhibition, or gene knockdown are modified for enhanced binding. In some alternatives, the disrupting, inhibition or gene knock down further comprises insertion of a nucleic acid into the gene. In some alternatives, the disrupting, inhibition, or gene knock down further comprises inserting a nucleic acid upstream from the gene. In some alternatives, the disrupting, inhibition, or gene knock down further comprises inserting a nucleic acid downstream from the gene. In some alternatives, nucleic acid is not inserted into the site of the gene, wherein the gene is not disrupted by insertion of the nucleic acid.

In some alternatives, the gene that is disrupted, inhibited, that is knocked-down is a co-receptor gene. In some alternatives, the co-receptor, which is disrupted, inhibited, or that is knocked-down is a co-receptor for viral entry. In some alternatives, the co-receptor, which is disrupted, inhibited, or that is knocked-down is a co-receptor for HIV entry. In some alternatives, the co-receptor, which is disrupted, inhibited, or that is knocked-down is CCR3, CXCR4 or CCR5. In some alternatives, the co-receptor, which is disrupted, inhibited, or that is knocked-down is CCR5. In some alternatives, the cell is a CD4 or a CD8 T-cell. In some alternatives, delivering the nucleic acid sequence encoding a chimeric antigen receptor to the T-cell is performed by transduction with a lentiviral system.

End Processing Nucleases

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. A end-processing enzyme can modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and/or chemotherapy agents.

The term "DNA end-processing enzyme" refers to an enzyme that modifies the exposed ends of DNA. A DNA end-processing enzyme can modify blunt ends or staggered ends (ends with 5' or 3' overhangs). A DNA end-processing enzyme can modify single stranded or double stranded DNA. A DNA end-processing enzyme can modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and/or chemotherapy agents. DNA end-processing enzymes can modify exposed DNA ends by adding one or more nucleotides, removing one or more nucleotides, removing or modifying a phosphate group and/or removing or modifying a hydroxyl group. Non-limiting examples of types of DNA end-processing enzymes include 5-3' exonucleases, 5-3' alkaline exonucleases, 3-5' exonucleases, 5' flap endonucleases, helicases, phosphatases, hydrolases and template-independent DNA polymerases. Examples of DNA end-processing enzymes that can be used include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CtIP, Pol mu, Pol lambda, MUS81, EME1, EME2, SLX1, SLX4 and/or UL-12. Many DNA end-processing enzymes are highly conserved throughout evolution, and thus likely to function in several different species. Further, homologues of DNA end-processing enzymes can be readily identifiable in organisms of biotechnological interest, including plants, animals, and algae.

The term "endonuclease/end-processing enzyme fusion protein" or "fusion protein having endonuclease and end-processing activity" refers to an enzyme, which has an endonuclease catalytic domain and an end-processing catalytic domain and exhibits endonuclease and end-processing activity.

Targeted DNA double-strand breaks introduced by rare-cleaving endonucleases can be harnessed for gene disruption applications in diverse cell types by engaging non-homologous end joining DNA repair pathways. However, endonucleases that create chemically clean breaks, which are often subject to precise repair, limit the efficiency of targeted gene disruption. Several alternatives described herein relate to a method of improving the rate of targeted gene disruptions caused by imprecise repair of endonuclease-induced site-specific DNA double-strand breaks. DNA end-processing enzymes or nucleases can be used to optimize activity or processivity. Some alternatives described herein utilize site specific endonucleases, such as end-processing nucleases that are coupled with the engineered nuclease to enhance the rate of targeted gene disruption. Coupling can be, for example, physical, spatial, and/or temporal.

Adoptive Cell Transfer

"Adoptive cell transfer" as described herein refers to the transfer of cells, immune-derived cells, back into the same patient or into a different recipient host. For isolation of immune cells for adoptive transfer, blood can be drawn into tubes containing anticoagulant and the PBM (buffy coat) cells are isolated, typically by density barrier centrifugation. In T-cell based therapies, the cells can be expanded in vitro using cell culture methods relying heavily on the immuno-modulatory action of interleukin-2 and returned to the patient in large numbers intravenously in an activated state. Anti-CD3 antibody can be used to promote the proliferation of T-cells in culture. Research into interleukin-21 suggests it can also play an important role in enhancing the efficacy of T cell based therapies prepared in vitro. Cells used in adoptive cell transfer can be used to deliver genetically modified lymphocytes, using recombinant DNA technology so as to achieve any number of goals. Disclosed herein are methods for introducing a CAR expressing lymphocyte into a subject. In alternatives described herein, adoptive cell transfer is used to transfer cells into a subject, wherein the cells are CAR expressing lymphocytes lacking a co-receptor for HIV.

Codon Optimization

Those skilled in the art will appreciate that gene expression levels are dependent on many factors, such as promoter sequences and regulatory elements. Another factor for maximal protein selection is adaptation of codons of the transcript gene to the typical codon usage of a host. As noted for most bacteria, small subsets of codons are recognized by tRNA species leading to translational selection, which can be an important limit on protein expression. In this aspect, many synthetic genes can be designed to increase their protein expression level. The design process of codon optimization can be to alter rare codons to codons known to increase maximum protein expression efficiency. In some alternatives, codon selection is described, wherein codon selection is performed by using algorithms that are known to those skilled in the art to create synthetic genetic transcripts optimized for higher levels of transcription and protein yield. Programs containing algorithms for codon optimization are known to those skilled in the art. Programs can include, for example, OptimumGene™, GeneGPS® algorithms, etc. Additionally synthetic codon optimized sequences can be obtained commercially for example from Integrated DNA Technologies and other commercially available DNA sequencing services. In some alternatives, CARs are prepared such that the genes for an scFv domain are codon optimized for expression in humans. In some alternatives, CARs are described, wherein the genes for the complete gene transcript are codon optimized for expression in humans, which can include gene transcripts for the intracellular signaling domains, co-stimulatory domains, spacer/linker domain and the scFv domain. In some alternatives, CARs are described, wherein genes for the CAR are optimized to have selected codons specifically for maximal protein expression in human cells, which can increase the concentration of CARs on a T-cell.

HIV

Human immunodeficiency virus (HIV) is a slowly replicating retrovirus, which leads to the progressive failure of the immune system allowing a subject infected with HIV to succumb to life-threatening infections and diseases. Despite drug intervention and prevention programs, 34 million people worldwide live with HIV. Currently, the standard treatment involves antiretroviral therapy (ART), and therapy that target viral enzymes and in particular inhibition of the HIV replication cycle. In many studies, specific binding to the HIV envelop proteins is highly desired in an attempt to neutralize the virus. However, a desirable method for inhibiting HIV proliferation and/or eradicating the infection completely is to specifically target and destroy HIV-infected cells, such as T cells, macrophages, microglial, and/or dendritic cells, using one or more of the CARs described herein. In some alternatives, CARs are described, wherein the CAR expressing lymphocytes specifically target HIV cells, such as T-cells and/or dendritic cells, for depletion. In some alternatives, CARs are described, wherein the CAR expressing lymphocytes specifically targeting HIV cells, such as T-cells, macrophages, microglial, and/or dendritic cells, can have a scFv domain that comprises domains, element, or portions of PG9, PGT128, and/or PGT145. In several alternatives, CARs have been shown to exhibit a cell killing effect when CAR expressing lymphocytes are exposed to HIV infected cells. In several alternatives, CAR expressing lymphocytes were shown to be specifically activated after stimulation by the presence of HIV+ infected cells.

HIV can enter its target cell by fusion at the plasma membrane by interacting initially with co-receptors that allow the HIV virus to dock onto the surface of the cell. In the present disclosure, the role of CAR has been extended to targeting T-cells to virally infected cells by genetically modifying T-cells to produce receptors that target viral proteins. Disclosed herein are methods for making a genetically modified T-cell comprising a CAR and lacking a co-receptor for HIV, and methods for developing CAR-expressing lymphocytes, wherein the CAR is designed to redirect T-cells to target-cells that express specific cell surface antigens, such as HIV-infected T-cells and/or dendritic cells. In some alternatives, a method of genetically modifying a T-cell comprising a chimeric antigen receptor, wherein said T-cell lacks a co-receptor for HIV is provided. In some alternatives, the method comprises delivering a nucleic acid sequence encoding a chimeric antigen receptor to a T-cell and disrupting a gene encoding a co-receptor for HIV in the T-cell. In some alternatives, the disrupting or inhibition is performed by RNAi. In some alternatives, the disrupting or inhibition is performed by a nuclease for targeted genome modification. In some alternatives, the nuclease used for disruption or inhibition is an engineered nuclease, a cleaving nuclease, a zinc finger nuclease, a transcription activator-like effector nuclease, meganuclease, a homing endonuclease, or a clustered regularly interspaced short palindromic repeat RNA guided nuclease, or a portion thereof. In some alternatives, the engineered nuclease used for disruption or inhibition comprises zinc fingers and, wherein the engineered nuclease comprises two, three, four, five, or six zinc fingers. In some alternatives, the engineered nuclease used for disruption or inhibition has a mutation enhancing activity. In some alternatives, the engineered nuclease used for disruption or inhibition further comprises a Fok1 nuclease, or a portion thereof. In some alternatives, the Fok1 nuclease used for disruption or inhibition is attached to the zinc fingers by a linker. In some alternatives, the linker is 4, 5, 6, 7, 8, 9, 10, 11, 12, 13, 14, or 15 amino acids in length or a length within a range defined by any two of the aforementioned lengths. In some alternatives, the zinc fingers are modified for enhanced binding.

In some alternatives, the disrupting or inhibition further comprises insertion of the nucleic acid into the gene. In some alternatives, the disrupting or inhibition further comprises inserting the nucleic acid upstream from the gene. In some alternatives, the disrupting or inhibition further comprises inserting the nucleic acid downstream from the gene. In some alternatives, the gene that is disrupted or inhibited is a co-receptor gene. In some alternatives, the co-receptor that is disrupted or inhibited is a co-receptor for viral entry. In some alternatives, the co-receptor that is disrupted or inhibited is a co-receptor for HIV entry. In some alternatives, the co-receptor that is disrupted or inhibited is CCR3, CXCR4 and/or CCR5. In some alternatives, the co-receptor that is disrupted or inhibited is CCR5. In some alternatives, delivering the nucleic acid sequence encoding a chimeric antigen receptor to the T-cell is performed by transduction with a lentiviral system.

HIV Therapy

HIV management can include the use of anti-retroviral drugs in order to control HIV infection. By way of example and not of limitation, classes of drugs for the treatment or management of HIV can include entry or fusion inhibitors (e.g., maraviroc and enfuvirtide), nucleoside reverse transcriptase inhibitors (e.g., zidovudine, abicavir, lamivudine, emtricitabine, and tenofovir), Non-nucleoside reverse transcriptase inhibitors (e.g., nevirapine, efavirenz, etravirine, and rilpivirine), integrase inhibitors (e.g., elvitegravir and dolutegravir), and/or protease inhibitors (e.g., Lopinavir, Indinavir, Nelfinavir, Amprenavir, Ritonavir, Darunavir, and Atazanavir). Combinational therapy with any of the disclosed classes of drugs in conjunction with one or more of the CAR-containing T-cells described herein can also be used for the treatment and management of HIV.

Disclosed herein are genetically modified T-cells, methods for making a genetically modified T-cell comprising a CAR and lacking a co-receptor for HIV, and methods for treating, inhibiting, or ameliorating HIV in a subject. In some alternatives, the genetically modified T-cell comprises a chimeric antigen receptor, wherein the genetically modified T-cell does not comprise a co-receptor for HIV. In some alternatives, the chimeric antigen receptor comprises a signal peptide, an antigen-binding domain, a transmembrane CD8 hinge domain, a co-stimulatory domain, and/or an intracellular domain of a T-cell receptor. In some alternatives, the antigen binding domain comprises a single chain variable fragment (scFv) domain from a high affinity broadly neutralizing antibody. In some alternatives, the high affinity broadly neutralizing antibody utilized is an anti-HIV neutralizing antibody. In some alternatives, the anti-HIV neutralizing antibody utilized comprises a sequence of PGT128 (SEQ ID NO: 1), PG9 (SEQ ID NO: 2), and/or PGT145 (SEQ ID NO: 3) or a binding fragment thereof. In some alternatives, the anti-HIV neutralizing antibody utilized comprises a sequence of PGT145 (SEQ ID NO: 3) or a binding fragment thereof. In some alternatives, the co-stimulatory domain utilized is CD137 (SEQ ID NO: 4). In some alternatives, the transmembrane CD8 hinge region utilized is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the co-stimulatory domain utilized comprises a domain of CDζ and, wherein the domain of CDζ comprises an amino acid sequence of SEQ ID NO: 5. In some alternatives, the co-receptor that is disrupted or inhibited is a co-receptor for viral entry. In some alternatives, the co-receptor that is disrupted or inhibited is a co-receptor for HIV entry. In some alternatives, the co-receptor that is disrupted or inhibited is CCR3, CXCR4 and/or CCR5. In some alternatives, the co-receptor that is disrupted or inhibited is CCR5.

Disclosed herein are methods of treating, inhibiting, or ameliorating HIV in a subject. In some alternatives, the method can comprise administering to the subject the genetically modified T-cell of any of the alternatives described herein. In some alternatives, the subject is identified or selected to receive an anti-HIV therapy. In some alternatives, the method further comprises monitoring or measuring the level or amount of HIV titer or a marker of HIV infection in said subject before, during, or after administration of the cell of any one of the alternatives described herein. In some alternatives, the genetically modified T-cell is administered to said subject by adoptive cell transfer. In some alternatives, the subject is already receiving or is provided or administered another form of anti-HIV therapy before during or after providing or administering any one or more of the CAR-containing T-cells described herein. In some alternatives, the anti-HIV therapy that is utilized in combination with one or more of the CAR-containing T-cells described herein is a fusion inhibitor, a nucleoside reverse transcriptase inhibitor, a non-nucleoside reverse transcriptase inhibitor, an integrase inhibitor, or a protease inhibitor or any combination thereof.
Additional Alternatives Methods of making a nucleic acid encoding a chimeric antigen receptor comprising providing nucleic acid sequence encoding a signal peptide, joining said nucleic acid sequence to a nucleic acid sequence encoding an antibody or binding fragment thereof; joining said nucleic acid sequence encoding an antibody or binding fragment to a nucleic acid encoding a transmembrane CD8 hinge region sequence; joining said nucleic acid encoding said transmembrane CD8 hinge region sequence to a nucleic acid encoding a T-cell receptor co-stimulatory domain gene sequence; and joining said nucleic acid encoding said T-cell receptor co-stimulatory domain gene sequence to a nucleic acid encoding an intracellular domain of a T-cell receptor sequence. In some alternatives, said antibody or binding fragment thereof is an HIV neutralizing antibody or a binding fragment thereof. In some alternatives, the antibody or binding fragment thereof comprises an amino acid sequence of a domain of PGT128 (SEQ ID NO: 6), a domain of PG9 (SEQ ID NO: 7), or a domain of PGT145 (SEQ ID NO: 8). In some alternatives, the transmembrane CD8 hinge region sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, said nucleic acid or a portion thereof, for example the nucleic acid encoding the antibody or binding fragment thereof, the nucleic acid encoding the transmembrane CD8 hinge region sequence, the nucleic acid encoding a T-cell receptor co-stimulatory domain gene sequence, or the nucleic acid encoding an intracellular domain of a T-cell receptor sequence, is codon optimized for expression in humans. In some alternatives, the codon optimization is performed by a computational method. In some alternatives, the co-stimulatory domain comprises a domain of CD137. In some alternatives, the domain of CD137 comprises the amino acid sequence of SEQ ID NO: 9. In some alternatives, the co-stimulatory domain comprises a domain of CDζ, and wherein the domain of CDζ comprises an amino acid sequence of SEQ ID NO: 10. In some alternatives, said nucleic acid sequence encoding an antibody or binding fragment thereof comprises or consists of a nucleic acid encoding a single chain variable fragments (scFv) from a high affinity broadly neutralizing antibody specific for HIV. In some alternatives, the antibody or binding fragment thereof is from a high affinity broadly neutralizing antibody that targets variable regions of HIV envelope. In some alternatives, the variable regions of HIV envelope are V1, V2, or V3. In some alternatives, the signal peptide comprises an amino acid sequence of SEQ ID NO: 11. In some alternatives, the transmembrane CD8 hinge region comprises an amino acid sequence of SEQ ID NO: 12.

More alternatives include a nucleic acid encoding a chimeric antigen receptor comprising a signal peptide, an antigen-binding domain, a transmembrane CD8 hinge domain, a co-stimulatory domain, and an intracellular domain of a T-cell receptor. In some alternatives, the antigen binding domain comprises a single chain variable fragments (scFv) from a high affinity broadly neutralizing antibody. In some alternatives, the high affinity broadly neutralizing antibody is an anti-HIV neutralizing antibody. In some alternatives, the anti-HIV neutralizing antibody comprises a sequence of PGT128 (SEQ ID NO: 6), PG9 (SEQ ID NO: 7), or PGT145 (SEQ ID NO: 8) or a binding fragment thereof. In some alternatives, the co-stimulatory domain is CD137 (SEQ ID NO: 9). In some alternatives, the transmembrane CD8 hinge region is 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the co-stimulatory domain comprises a domain of CDζ, wherein the domain of CDζ comprises an amino acid sequence of SEQ ID NO: 10. In some alternatives, the transmembrane CD8 hinge region comprises an amino acid sequence of SEQ ID NO: 12. In some alternatives, the signal peptide comprises an amino acid sequence of SEQ ID NO: 11. In some alternatives, the antigen-binding domain is from a high affinity broadly neutralizing antibody that targets variable regions of HIV envelope. In some alternatives, the variable regions of HIV envelope are V1, V2, and/or V3. More alternatives concern a chimeric antigen receptor encoded by any one of the nucleic acids described above. More alternatives concern a cell comprising any one of the nucleic acids or chimeric antigen receptors set forth above. More alternatives concern methods of treating, inhibiting, or ameliorating HIV in a subject comprising administering to the subject the aforementioned cell. In some alternatives, the subject is identified or selected to receive an anti-HIV therapy. Some alternatives further comprise monitoring or measuring the level or amount of HIV titer or a marker of HIV infection in said subject before, during, or after administration of the cell. In some alternatives, the cell is administered to said subject by adoptive cell transfer. In some alternatives, the subject is already receiving another form of anti-HIV therapy.

Disclosed here are methods of genetically modifying a T-cell comprising a chimeric antigen receptor, wherein said T-cell lacks a co-receptor for HIV. In some alternatives, the method can comprise delivering a nucleic acid sequence encoding a chimeric antigen receptor to a T-cell and disrupting a gene encoding a co-receptor for HIV in the T-cell. In some alternatives, the chimeric antigen receptor further comprises a signal peptide, an antigen-binding domain, a transmembrane CD8 hinge domain, a co-stimulatory domain, and/or an intracellular domain of a T-cell receptor. In some alternatives, the antigen binding domain that is utilized comprises a single chain variable fragment (scFv) domain from a high affinity broadly neutralizing antibody. In some alternatives, the high affinity broadly neutralizing antibody that is utilized is an anti-HIV neutralizing antibody. In some alternatives, the anti-HIV neutralizing antibody comprises a sequence of PGT128 (SEQ ID NO: 1), PG9 (SEQ ID NO: 2), and/or PGT145 (SEQ ID NO: 3) or a binding fragment thereof. In some alternatives, the anti-HIV neutralizing antibody that is utilized comprises a sequence of PGT145 (SEQ ID NO: 3) or a binding fragment thereof. In some alternatives, the co-stimulatory domain that is utilized is CD137 (SEQ ID NO: 4). In some alternatives, the transmembrane CD8 hinge region that is utilized is 10, 11, 12, 13, 14, 15, 16, 17, 18, 19, 20, 21, 22, 23, 24, 25, 26, 27, 28. 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the co-stimulatory domain that is utilized comprises a domain of CDζ and, wherein the domain of CDζ comprises an amino acid sequence of SEQ ID NO: 5.

In some alternatives, the step of disrupting or inhibiting a gene is performed by RNAi. In some alternatives, the disrupting or inhibiting of the gene is performed by a nuclease for targeted genome modification. In some alternatives, the nuclease that is utilized is an engineered nuclease, a cleaving nuclease, a zinc finger nuclease, a transcription activator-like effector nuclease, meganuclease, a homing endonuclease, and/or a clustered regularly interspaced short palindromic repeat RNA guided nuclease, and/or a portion thereof. In some alternatives, the engineered nuclease that is utilized comprises zinc fingers and, wherein the engineered nuclease comprises two, three, four, five, or six zinc fingers. In some alternatives, the engineered nuclease that is utilized has a mutation enhancing activity. In some alternatives, the engineered nuclease that is utilized further comprises a Fok1 nuclease, or a portion thereof. In some alternatives, the Fok1 nuclease that is utilized is attached to the zinc fingers by a linker. In some alternatives, the linker is 4, 5, 6, 7, 8, 9, 10, 11, 12, 13, 14, or 15 amino acids in length or a length within a range defined by any two of the aforementioned lengths. In some alternatives, the zinc fingers that are utilized are modified for enhanced binding. In some alternatives, the disrupting or inhibiting further comprises insertion of the nucleic acid into the gene. In some alternatives, the disrupting or inhibiting further comprises inserting the nucleic acid upstream from the gene. In some alternatives, the disrupting or inhibiting further comprises inserting the nucleic acid downstream from the gene. In some alternatives, the gene that is disrupted or inhibited is a co-receptor gene. In some alternatives, the co-receptor that is disrupted or inhibited is a co-receptor for viral entry. In some alternatives, the co-receptor that is disrupted or inhibited is a co-receptor for HIV entry. In some alternatives, the co-receptor that is disrupted or inhibited is CCR3, CXCR4 and/or CCR5. In some alternatives, the co-receptor that is disrupted or inhibited is CCR5. In some alternatives, the cell is a CD4 or a CD8 T-cell. In some alternatives, delivering the nucleic acid sequence encoding a chimeric antigen receptor to the T-cell is performed by transduction with a lentiviral system.

Disclosed herein is a genetically modified T-cell. In some alternatives, the genetically modified T-cell can comprise a chimeric antigen receptor, and wherein the genetically modified T-cell does not comprise a co-receptor for HIV. In some alternatives, the chimeric antigen receptor comprises a signal peptide, an antigen-binding domain, a transmembrane CD8 hinge domain, a co-stimulatory domain, and/or an intracellular domain of a T-cell receptor. In some alternatives, the antigen binding domain that is utilized comprises a single chain variable fragment (scFv) domain from a high affinity broadly neutralizing antibody. In some alternatives, the high affinity broadly neutralizing antibody that is utilized is an anti-HIV neutralizing antibody. In some alternatives, the anti-HIV neutralizing antibody that is utilized comprises a sequence of PGT128 (SEQ ID NO: 1), PG9 (SEQ ID NO: 2), and/or PGT145 (SEQ ID NO: 3) or a binding fragment thereof. In some alternatives, the anti-HIV neutralizing antibody that is utilized comprises a sequence of PGT145 (SEQ ID NO: 3) or a binding fragment thereof. In some alternatives, the co-stimulatory domain that is utilized is CD137 (SEQ ID NO: 4). In some alternatives, the transmembrane CD8 hinge region that is utilized is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths. In some alternatives, the co-stimulatory domain comprises a domain of CDζ and, wherein the domain of CDζ comprises an amino acid sequence of SEQ ID NO: 5. In some alternatives, the co-receptor that is inhibited or disrupted is a co-receptor for viral entry. In some alternatives, the co-receptor that is inhibited or disrupted is a co-receptor for HIV entry. In some alternatives, the co-receptor that is inhibited or disrupted is CCR3, CXCR4 and/or CCR5. In some alternatives, the co-receptor that is inhibited or disrupted is CCR5.

Disclosed herein are methods of treating, inhibiting, or ameliorating HIV in a subject. In some alternative, the method can comprise administering to the subject the genetically modified T-cell of any of the alternatives described herein. In some alternatives, the subject is identified or selected to receive an anti-HIV therapy. In some alternatives, the method can further comprise monitoring or measuring the level or amount of HIV titer or a marker of HIV infection in said subject before, during, or after administration of the T-cell of any of the alternatives described herein. In some alternatives, the cell is administered to said subject by adoptive cell transfer. In some alternatives, the subject is already receiving or is provided or administered another form of anti-HIV therapy before during or after providing or administering any one or more of the CAR-containing T-cells described herein. In some alternatives, the anti-HIV therapy is administration of a fusion inhibitor, a nucleoside reverse transcriptase inhibitor, a non-nucleoside reverse transcriptase inhibitor, an integrase inhibitor, or a protease inhibitor or any combination thereof.

Constructs

Constructs of the anti-HIV CAR were created as follows: The domains of the construct (MND promoter, GFP, scFv of PGT145, CD8 hinge region, CD137 co-stimulatory signaling domain, and CD3ζ), were codon optimized for human expression using a commercially available algorithm. Constructs were then ordered through Integrated DNA Technologies as needed. A schematic of the CARs for the PGT145 CAR is shown in FIG. 2.

CAR were constructed through the fusion of the scFv domain from PGT145 to a transmembrane CD8 hinge domain to a cytoplasmic co-stimulatory domain derived from CD137, and to a intracellular signaling domain CD3ζ. The vectors used to carry the genetic transcript for the PGT145 CAR is controlled by a MND promoter (SEQ ID NO: 13) and also contains a GFP marker. To generate CAR expressing T-cells, gene constructs containing the sequences for the CAR fusion protein were inserted into a backbone of a pRRL plasmid. Cells were transduced with lentivirus encoding anti-HIV PGT145 CAR to generate a population of CAR expressing cells. Flow cytometry can be used to enrich for cells expressing GFP or other marker.

Constructs of the anti-HIV CAR were created as follows: Genes for an EF1α promoter, GFP, PGT128, CD8 hinge region, CD137 co-stimulatory signaling domain, CD3, and were codon optimized for human expression using a commercially available algorithm. Gene constructs were then ordered through Integrated DNA Technologies. A schematic outlining the steps involved in the development of the CARs for the PGT128 CAR, PG9 CAR and the PGT145 CAR are shown in FIG. 2.

Second generation CARs were constructed through the fusion of the scFv from either PG9, PGT127, PGT145 to a transmembrane CD8 hinge domain to a cytoplasmic co-stimulatory domain derived from CD137, and to a intracellular signaling domain CD3ζ. The vectors used to carry the genetic transcript for all CARs, pRRL, were controlled by a MND promoter and also comprised a GFP marker fusion to the CAR. To generate CAR expressing T-cells, gene constructs containing the sequences for the CAR fusion protein were inserted into a backbone of a pRRL plasmid. Cells were transduced with lentivirus encoding anti-HIV CAR to generate a population of CAR expressing cells.

Cell Activation Assays

Cell activation assays were performed as follows: For small scale cultures, non-transduced or transduced primary donor lymphocyte cells (PGT128-CAR, PG9-CAR, PGT145-CAR) were incubated with uninfected T-cells, and HIV+ infected T-Cells. For controls, the primary donor lymphocytes expressing a CAR19, were incubated with HIV+ infected cells, and cells expressing anti-HIV CAR were mixed with HIV-uninfected target cells.

Cell killing of HIV-infected cells were performed as follows: HIV-infected cells (targets) were mixed with CAR-expressing lymphocytes (effectors) that lacked co-receptors for HIV. Graphs show the results of the PGT145 CAR or mock CAR lymphocytes mixed with stimulated HIV-infected cells or the uninfected parental cell line, as assessed by flow cytometry. The CAR contains GFP and the target T-cells are loaded with fluorescent Cell Tracker (Invitrogen).

Activation of Anti-HIV CAR+ T-Cells in the Presence of HIV Infected Cells

Anti-HIV PGT145 CAR+ T-cells lacking a co-receptor for HIV can be used to target HIV infected cells for killing. Anti-HIV PGT145 CAR+ T-cells are activated in the presence of HIV infected T-cells. In an experiment to evaluate killing of HIV infected cells by CAR expressing T-cells that lack an HIV co-receptor, T-cells expressing Anti-HIV CARs comprising scFv domains derived from PGT145, and controlled by a MND promoter can be incubated with HIV+ infected T-cells for 24 hours. As a control, T-cells carrying a Mock gene can be incubated with HIV+ infected T-cells, and Anti-HIV CAR expressing T-cells were incubated with uninfected cells. All CAR expressing T-cells can then be assayed for expression of cell surface CD137 as a marker for CAR activation. It should be expected that only Anti-HIV PGT145 CAR expressing T-cells lacking a co-receptor for HIV can be activated in the presence of HIV+ T-cells, while the control using a mock vector would not have activation in the presence of HIV+ T-cells, and the control Anti-HIV CAR expressing T-cells lacking a co-receptor for HIV would not have activation in the presence of uninfected T-cells.

Activation of Anti-HIV CAR+ T-Cells, where the T-Cells Lack Expression of a CCR5 Co-Receptor, in the Presence of HIV Infected Cells Anti-HIV CAR+ T-cells lacking a co-receptor for HIV can be used to target HIV infected cells for killing. In an experiment, T-cells expressing Anti-HIV CARs comprising scFv domains derived from PGT145, a co-stimulatory domain, and controlled by a promoter can be incubated with HIV infected T-cells. As a control, T-cells carrying mock CAR are incubated with HIV infected T-cells. Experiments can be run in duplicate. IFNγ is known to be secreted early in the immune response. A standard curve can be generated using concentrations of IFNγ at 31 pg/μl, 62 pg/μl, 125 pg/μl, 250 pg/μl, 0.5 ng/μl, and 1 ng/μl to obtain a standard curve of concentration vs OD at 280 nm. IFNγ expression can be measured for wells carrying a blank, unstimulated HIV positive cells, stimulated HIV positive cells, HIV negative cells, stimulated HIV negative cells, T-cells lacking a co-receptor (CCR5) and expressing $CAR^{PGT145}$ controlled by an EF1α promoter, T-cells lacking a co-receptor (CCR5) and expressing $CAR^{PGT145}$ controlled by an MND promoter, T-cells expressing a mock CAR, unstimulated HIV+ cells mixed with T-cells lacking a co-receptor (CCR5) and expressing $CAR^{PGT145}$ under a EF1 promoter, unstimulated HIV positive cells mixed with T-cells lacking a co-receptor (CCR5) and carrying CAR$^{PGT145}$ under an MND promoter, unstimulated HIV positive cells mixed with T-cells lacking a co-receptor (CCR5) and carrying a mock CAR, stimulated HIV+ cells mixed with T-cells lacking a co-receptor (CCR5) and expressing CAR$^{PGT145}$ under a EF1 promoter, stimulated HIV positive cells mixed with T-cells lacking a co-receptor (CCR5) and carrying CAR$^{PGT145}$ under an MND promoter, stimulated HIV positive cells mixed with T-cells carrying a mock CAR, unstimulated HIV negative cells mixed with T-cells lacking a co-receptor (CCR5) and expressing CAR$^{PGT145}$ under a EF1 promoter, unstimulated HIV negative cells mixed with T-cells lacking a co-receptor (CCR5) and carrying CAR$^{PGT145}$ under an MND promoter, unstimulated HIV negative cells mixed with T-cells carrying a mock CAR, stimulated HIV negative cells mixed with T-cells lacking a co-receptor (CCR5) and expressing CAR$^{PGT145}$ under a EF1 promoter, stimulated HIV negative cells mixed with T-cells lacking a co-receptor (CCR5) and carrying CAR$^{PGT145}$ under an MND promoter, and stimulated HIV negative cells mixed with T-cells lacking a co-receptor (CCR5) and carrying a mock CAR. The tests can be performed and compared with the standard curve. It can be expected that the production of IFNγ is specifically induced in T-cells lacking a co-receptor (CCR5) and carrying CARs comprising scFv domains of strong neutralizing antibodies of HIV are specifically activated in the presence of HIV positive cells.

Quantification of Anti-CAR Killing of HIV Infected Cells

Anti-HIV CAR$^{PGT145}$ T-cells lacking a co-receptor (CCR5) can be used to target HIV infected cells for killing. For the experiment, $CAR^{PGT145}$ expressing T-cells can be mixed with HIV infected cell lines, and assayed for the quantification of anti-HIV $CAR^{PG145}$ killing of HIV positive cells. The $CAR^{PGT145}$ expressing T cells can contain GFP and the target T-cells can be loaded with fluorescent Cell Tracker (Invitrogen). Flow cytometry can be used to separate the target cells (GFP(−)) and the CAR expressing T-cells (GFP(+)). It would be expected that anti-HIV CAR carrying T-cells lacking a co-receptor (CCR5) can kill HIV infected cells and lead to the decrease of HIV DNA in the cell culture. Furthermore it can be expected that the decrease of HIV DNA is increased in a T-cell lacking a co-receptor (CCR5) than with a T-cell that only comprises an $CAR^{PGT145}$.

Knock Down of the Co-Receptor (CCCR5) by MegaTal

For the experimental design, donor PBMC were isolated and stimulated with anti-CD3/CD28 for 24 hours. After stimulation, the stimulated PBMC were transduced with a lentiviral vector containing an anti-HIV chimeric antigen receptor (CAR) and GFP gene construct. After 4-5 days, the transduced PBMCs were then transfected with MegaTal mRNA in order to target the CCR5 gene. The cells can then be sorted for negative CCR5 negative GFP positive cells. After sorting, the cells are then expanded for 7-21 days. The expanded cell set can then be mixed with HIV infected cells and with fresh PBMC cells from allogeneic donors and cultured for 1-7 days.

Attention is drawn to FIG. 3 which shows a bar graph illustrating the results of CCR5 disruption in the CAR-expressing cells. As shown, three sets of cells were used: cells with no transduction (Mock), cells with a control GFP under the control of a MND promoter (MND CTRL), and cells carrying a $CAR^{PGT145}$ under the control of a MND promoter (CAR). The three types of cells were not targeted for CCR5 disruption (CTRL), were targeted for CCR5 disruption using a CCR5-specific megaTAL (MT), or were targeted for CCR5 disruption using a CCR5-specific megaTAL in conjunction with an end-processing nuclease (MT+Trx). The percentage of CCR5 disruption was evaluated by examining what percentage of the CCR5 gene can be disrupted in vitro using the CCR5-specific megaTAL. As shown, CCR5 specific MegaTal disruption can knock down CCR5 in CAR+ T-cells.

Anti-CAR Function of T-Cells that Lack HIV Co-Receptors in the Absence of Antiretrovirals Fresh donor PBMC were treated with CD3/CD28 overnight before being spinoculated with virus or mixed (co-cultured) with HIV-infected cells. Results are shown with two different viral strains, JR-CSF and ME1. HIV protein production was assessed by p24 ELISA which detects HIV capsid protein. When there was detectable virus production, or at time points after infection when we expected to have detectable HIV production, CAR+ lymphocytes or controls were added to the viral culture at prescribed effector to target cell ratios. Often a ratio of 2 CAR+ cells to 1 target cell was used. Once CAR+ lymphocytes or controls were added, supernatant and cells were collected at regular intervals. Supernatant was tested for HIV capsid protein using a commercially available p24 ELISA detection kit. Cells were also evaluated by flow cytometry at defined time points. These experiments were performed in the absence of antiretrovirals.

As shown in FIGS. 4A and 4B, anti-HIV $CAR^{PGT145}$ T-cells lacking co-receptors are capable of reducing the amount of HIV protein (viral capsid proteins) in culture in the absence of antiretrovirals. Two different HIV viruses (JRCSF and ME1) were grown in the donor cells for approximately three days and then mixed with: no allogeneic cells, allogeneic cells engineered to express either no CAR (negative control), GFP plus an anti-HIV CAR ($CAR^{PGT145}$) without disruption of CCR5, allogeneic cells expressing an anti-HIV CAR ($CAR^{PGT145}$) with disrupted CCR5, allogeneic cells with no CAR but with disruption of CCR5, allogeneic cells transduced with GFP and expanded but without an anti-HIV CAR or CCR5 disruption, or allogeneic cells transduced with GFP and with CCR disrupted but no CAR. At 72 and 120 hours, the amount of HIV protein detected was more than a log less when cells with an anti-HIV CAR ($CAR^{PGT145}$) were added versus when cells without an anti-HIV CAR were added. This figure shows that the T-cells with anti-HIV CAR with the CCR5 disruption are able to decrease the amount of HIV capsid protein (p24) produced in viral culture. As such, evidence is provided that both anti-CAR and CCR5 disruption reduce the amount of HIV protein more than either intervention alone. This data provides evidence that CD4+ T-cells engineered to be HIV-specific can be infected with HIV and also that the HIV specific CD4 cells may be important for optimal control of HIV infection.

Effect of HIV Infection on Cell Surface Expression of CCR5

The effect of HIV infection on cell surface expression of CCR5 was investigated. T-cells were mixed with cells from a different donor with actively replicating HIV. The T-cells used were T-cells expressing Anti-HIV CARs comprising scFv domains derived from PGT145 and controlled by a MND promoter, and T-cells expressing Anti-HIV CARs comprising scFv domains derived from PGT145 controlled by a MND promoter and disrupted with megaTAL for CCR5, as well as control cells with no $CAR^{PGT145}$, and control cells with no $CAR^{PGT145}$ which were also treated with megaTAL for CCR5. The T-cells were cultured in the presence of active replicating HIV for 24 hours. Two strains were used for the experiment, JRCSF, and ME1. The T-cells were then assayed for expression of cell surface CCR5.

Attention is drawn to FIG. 5, which shows panels A, B, C, and D illustrating fluorescence activating cell sorting (FACs) experiment gated on cell surface CCR5 expression (using a CCR5 monoclonal antibody conjugated to PE) when grown in the presence of active HIV replication. Anti-HIV CAR+ T-cells that contain a single chain variable fragment (scFv) derived from PGT145 shown in FIG. 2 (panel B and D) and controls without CAR (panels A and C) were treated with (panel C and D) or without (panel A and B) the CCR5-specific megaTAL. Cells were grown in the presence of no HIV or two different HIV strain (JR-SCF or ME1). Panels A, B, C and D are histograms showing the mean fluorescence of CCR5 on CAR-expressing (as indicated by GFP) and CD4+ cells that appear alive based on the live/dead stain.

As shown in the bottom panels, CCR5 megaTAL treated cells have less detectable CCR5 expression after HIV infection. As shown in panel D of FIG. 5, CCR5 disrupted cells with anti-HIV $CAR^{PGT145}$ have a greater decrease in CCR5 expression than with the cells with only the anti-HIV $CAR^{PGT145}$, indicating that CCR5 disruption in the anti-HIV CAR containing cell population substantially causes cells to have less detectable cell surface CCR5.

Anti-HIV $CAR^{PGT145}$ T-cells lacking the co-receptor CCR5 are relatively protected from HIV infection. For the experiment, $CAR^{PGT145}$ expressing T-cells were mixed with HIV infected cell culture or non-infected cell culture. The modified T-cells were assayed for CCR5 expression by flow cytometry. Attention is drawn to FIG. 6, which shows a subset of the data shown in FIG. 5. The four graphs in panels A, B, C, and D, are arranged as in FIG. 5, wherein CAR-expressing cells (panel B and D) and cells with CCR5 disruption (panels C and D are gated on the live, CAR (GFP)+, live cells, and CCR5 cell-surface expression is plotted on the X-axis. Dot plots are shown of the cells in the presence of no HIV or the JR-CSF variant. Dot plots are shown instead of histograms as in FIG. 5 to provide more detail of the distribution than is available in the histograms in FIG. 5. In the bottom panels CCR5-disrupted cells with anti-HIV CAR had a greater decrease in CCR5 expression than the cells with only the anti-HIV CAR (upper right panels) when grown in the presence of HIV replication, demonstrating effective CCR5 disruption in the anti-HIV CAR containing cell population.

Anti-HIV CAR Expressing T-Cells Function in the Absence of Retrovirals

T-cells used for the experiment were T-cells without $CAR^{PGT145}$ and without CCR5 co-receptor disruption, T-cells expressing a $CAR^{PGT145}$ without CCR5 co-receptor disruption, and T-cells without $CAR^{PGT145}$ but with disrupted CCR5 co-receptor, and T-cells expressing a $CAR^{PGT145}$ with CCR5 co-receptor disruption. The T-cells were grown with and without exposure to HIV (JR-CSF). There was very little CCR5 expression by any of the cells when they were first mixed with virus (0 Hours). Over time the percentage of CCR5-expressing cells increases. However, it is clear that there are fewer CCR5+ cells when grown in the presence of replicating HIV (bottom four lines). When cells were mixed with replicating HIV, this data also demonstrates that in cells with CCR5 disruption there is much less CCR5 expression (bottom two lines).

Figure 7:
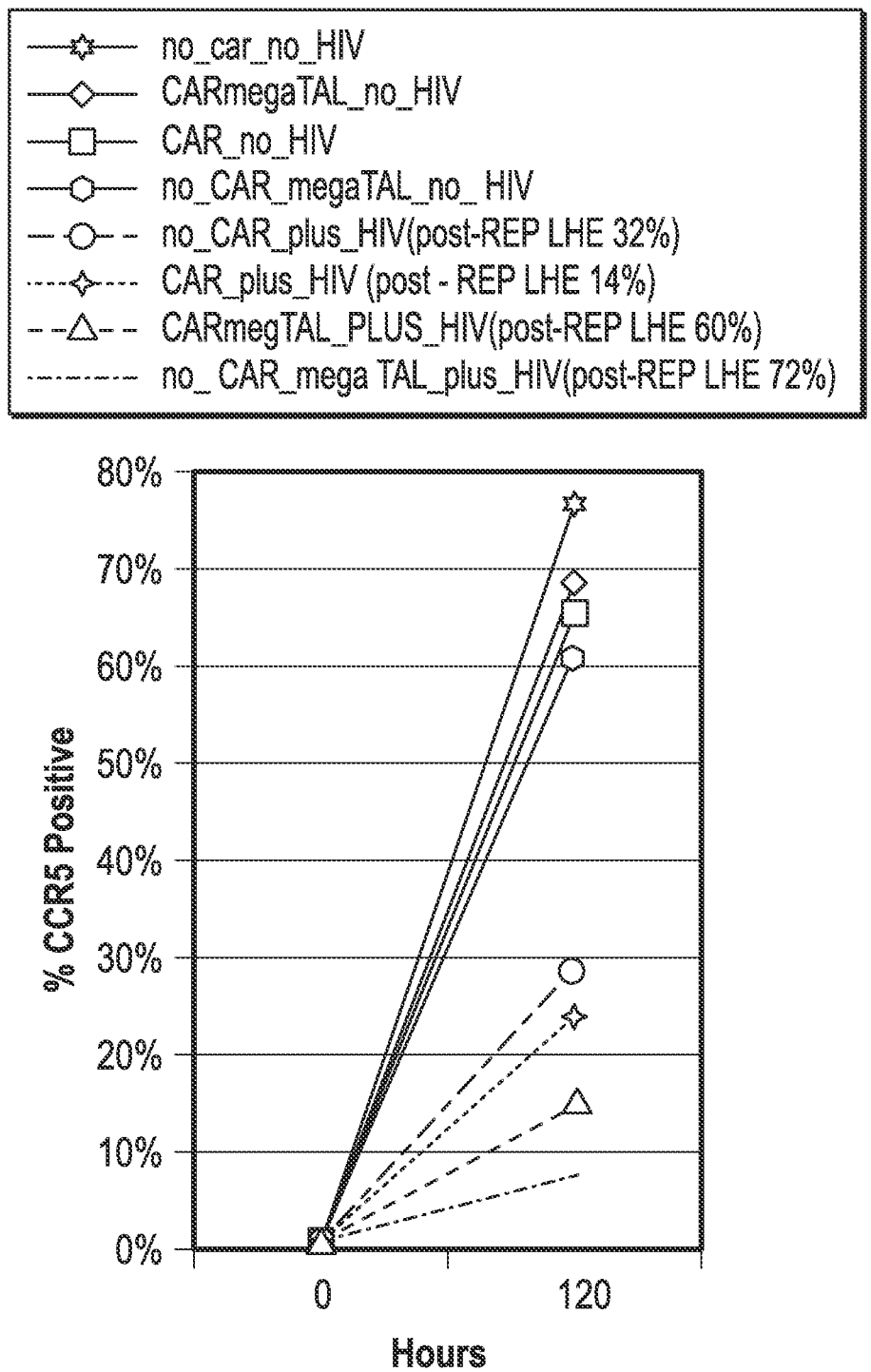
FIG. 7 shows a graph illustrating the amount of CCR5 positive T-cells after exposure to HIV infected cells after 120 hours. T-cells used for the experiment were T-cells without $CAR^{PGT145}$ and without CCR5 co-receptor disruption, T-cells expressing a $CAR^{PGT145}$ without CCR5 co-receptor disruption, and T-cells without $CAR^{PGT145}$ but with disrupted CCR5 co-receptor, and T-cells expressing a $CAR^{PGT145}$ with CCR5 co-receptor disruption. The T-cells were grown with and without exposure to HIV (JR-CSF). There was very little CCR5 expression by any of the cells when they were first mixed with virus (0 Hours). Over time the percentage of CCR5-expressing cells increases. However, it is clear that there are fewer CCR5+ cells when grown in the presence of replicating HIV (bottom four lines). When cells were mixed with replicating HIV, this data also demonstrates that in cells with CCR5 disruption there is much less CCR5 expression (bottom two lines).
Figures 1, 8:
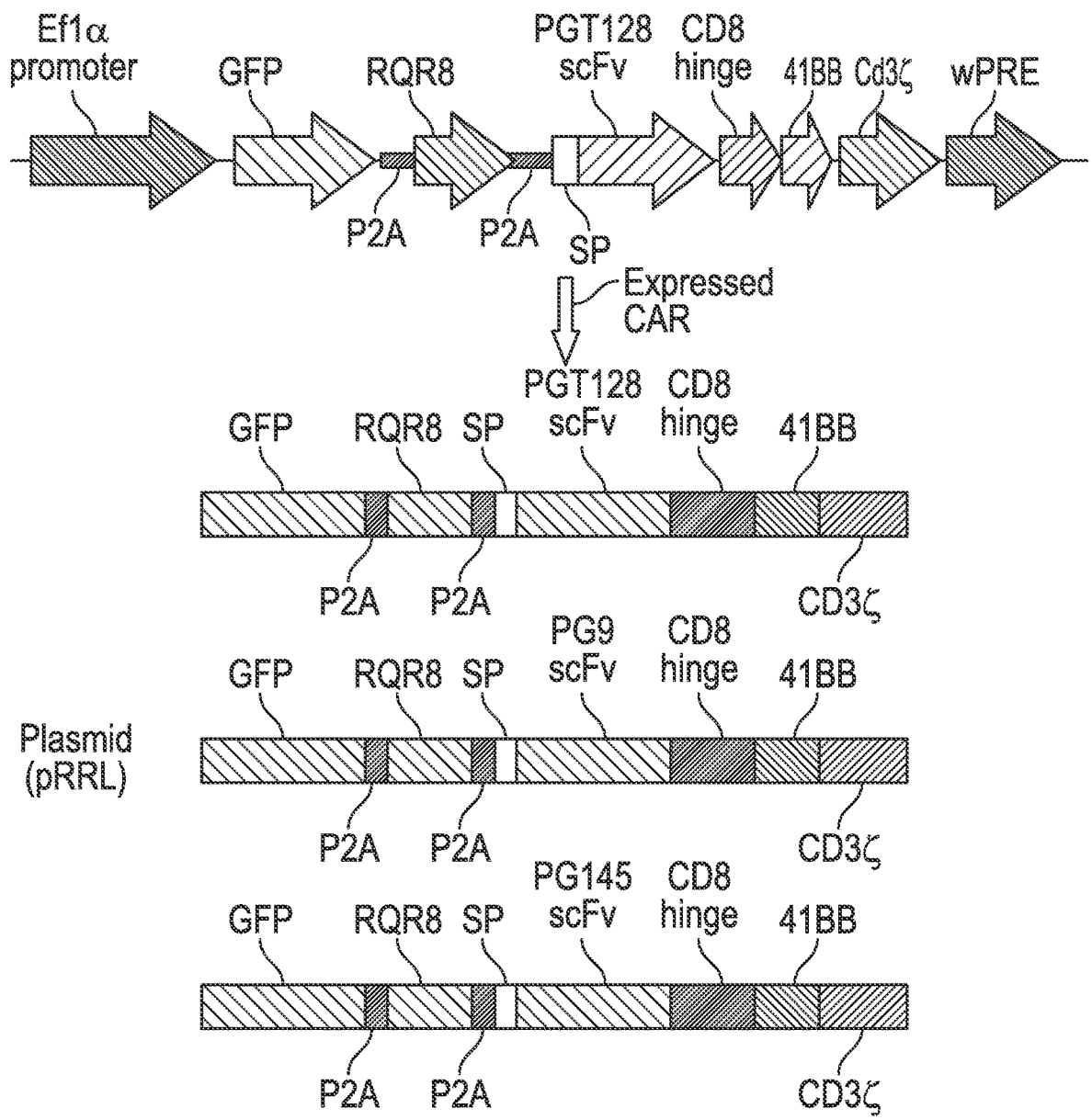
FIG. 8 is a graphical illustration of four anti-HIV CAR gene constructs containing genes for GFP markers. The constructs can contain genes of domains from the broadly neutralizing anti-HIV antibodies, PG9, PGT128, and PGT145.

As shown in FIG. 7, anti-HIV $CAR^{PGT145}$ expressing T-cells that lack the co-receptor CCR5 have a reduced percentage of CCR5-expressing cells when grown in culture with HIV in the absence of antiretrovirals. The HIV virus was grown in the donor cells for approximately three days and then mixed with allogeneic cells engineered to express either no $CAR^{PGT145}$ (control), $CAR^{PGT145}$, $CAR^{PGT145}$ with CCR5 co-receptor, no $CAR^{PGT145}$ with CCR5 co-receptor, GFP plus an anti-HIV CAR ($CAR^{PGT145}$) or GFP and no CAR (negative control). In 120 hours, the amount of CCR5 co-receptor expression on the cell surface was detected by flow cytometry. As shown, the percentage of cells expressing CCR5 was decreased as expected when CCR5 was disrupted. This effect was more pronounced over a five day period.

Activation of Anti-HIV CAR+ T-Cells in the Presence of HIV Infected Cells.

Figure 9:
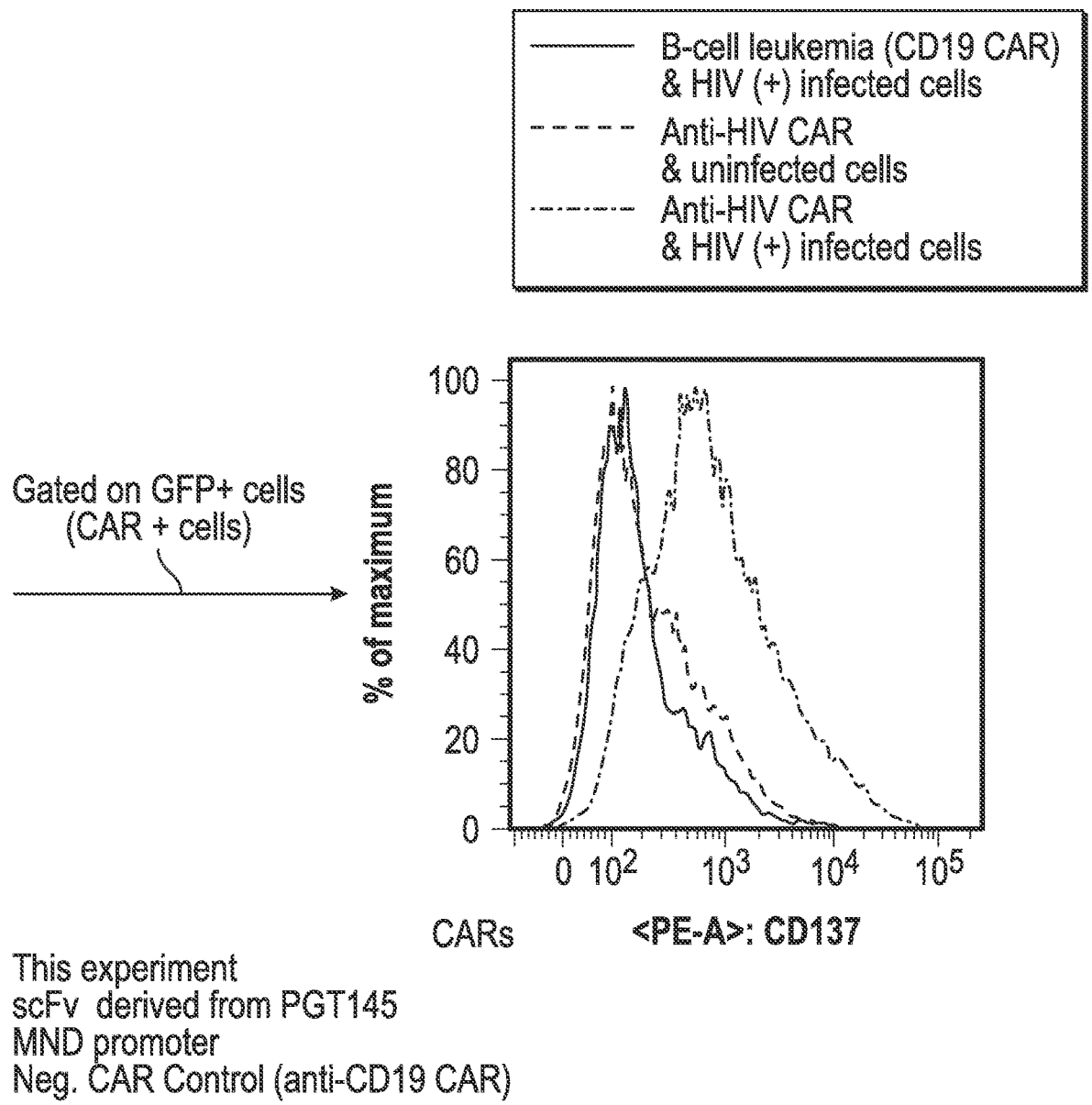
FIG. 9 is a graph illustrating a fluorescence activating cell sorting (FACs) experiment that gated on GFP for the detection of Anti-HIV CAR+ T-cells that carry the genes of PGT145 shown in FIG. 3. As shown, the first control cells, B-cell leukemia (CD19 CAR), when mixed with HIV cells for 24 hours are not activated. The second control, anti-HIV CAR is mixed with uninfected cells for 24 hours, and is not activated. Anti-HIV CAR expressing cells, when mixed with HIV+ infected cells are activated. Extracellular staining of CD137 was used as a marker of CAR activation. The experiments were performed in the presence of antiretrovirals.

Anti-HIV CAR+ T-cells can be used to target HIV infected cells for killing. As shown in FIG. 9, Anti-HIV CAR+ T-cells are activated in the presence of HIV infected T-cells. In the experiment, T-cells expressing Anti-HIV CARs comprising scFv derived from PGT145, and controlled by a MND promoter were incubated with HIV+ infected T-cells for 24 hours. As a control, Anti-leukemia CARCD19CAR+ expressing T-cells, were incubated with HIV+ infected T-cells, and Anti-HIV CAR expressing T-cells were incubated with uninfected cells. All CAR expressing T-cells were then assayed for expression of cell surface CD137 as a marker for CAR activation. As shown in the graph, Anti-HIV CAR expressing T-cells were activated only in the presence of HIV+ T-cells, while the control using T-cells expressing CARCD19 did not have activation in the presence of HIV+ T-cells, and the control Anti-HIV CAR expressing T-cells did not have activation in the presence of uninfected T-cells. In conclusion, anti-HIV CAR expressing T-cells had specific activation only in the presence of HIV+ infected T– cells.

Activation of Anti-HIV CAR+ T-Cells in the Presence of HIV Infected Cells.

Figure 10:
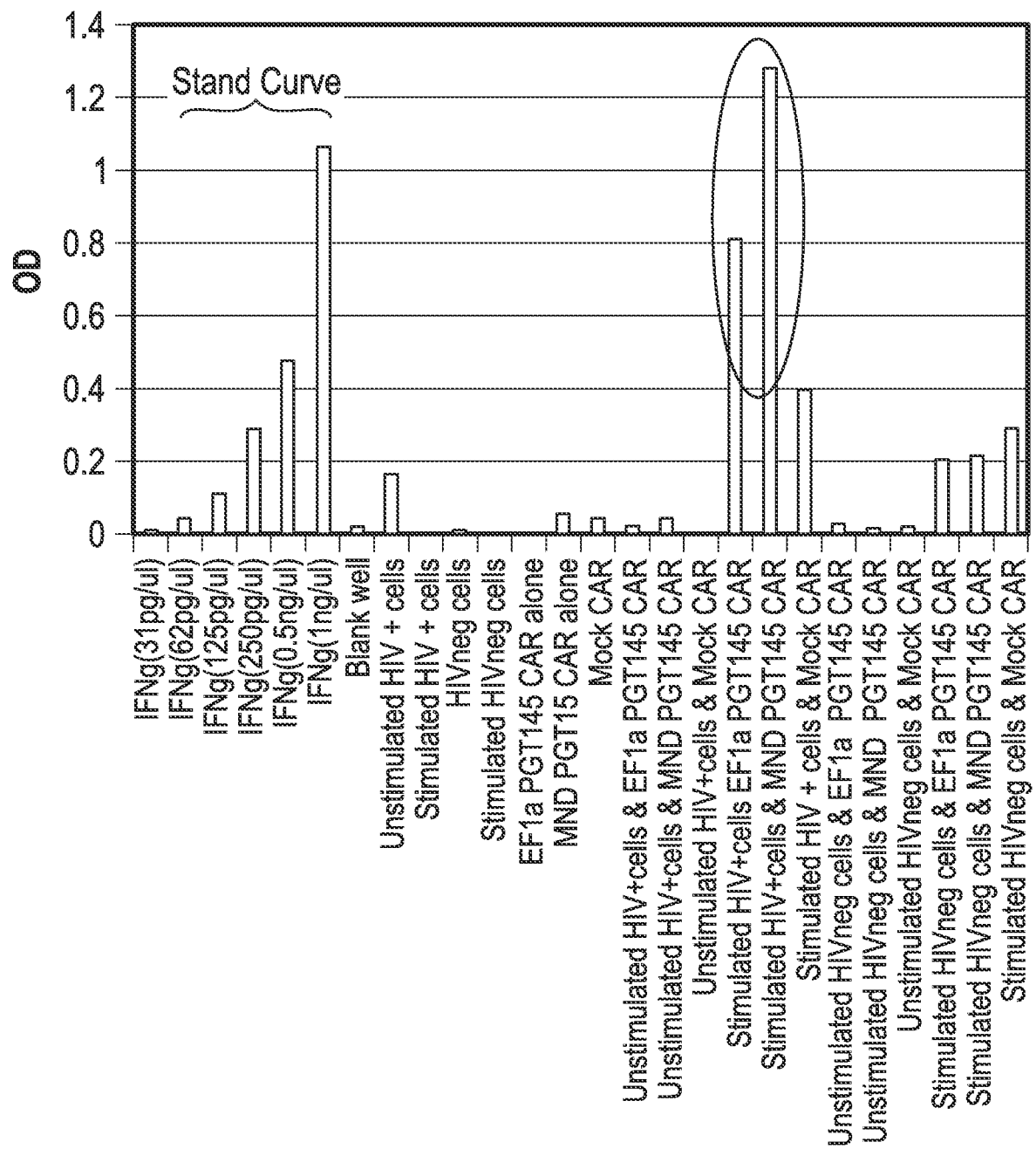
FIG. 10 is a graph depicting IFN-γ expression of T-cells. As shown in the control of a mock CAR exposed to HIV+ cells, the IFN-γ expression is low. However, anti-HIV CAR+ T cells express IFN-γ in the presence of HIV-infected cells, indicating activation. These experiments were carried out in the presence of antiretrovirals.
Figure 11A:
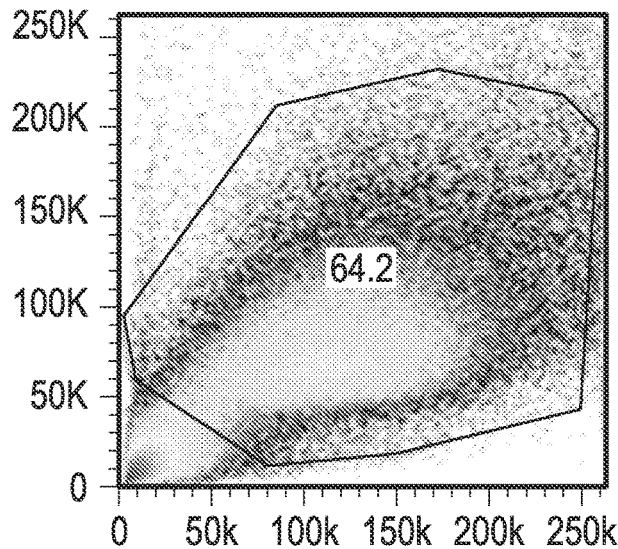
FIG. 11 shows a series of graphs depicting the gating strategy used to quantify the killing of HIV-infected cells (target cells) by the anti-HIV CAR. As shown, in the series of plots, flow cytometry was used to quantify the number of target-cells (HIV+ cells). In the graphs depicted the T-cells expressed the PG9 CAR and were used to kill stimulated ACH2 (HIV+) cells. These experiments were carried out in the presence of antiretrovirals.
Figure 11B:
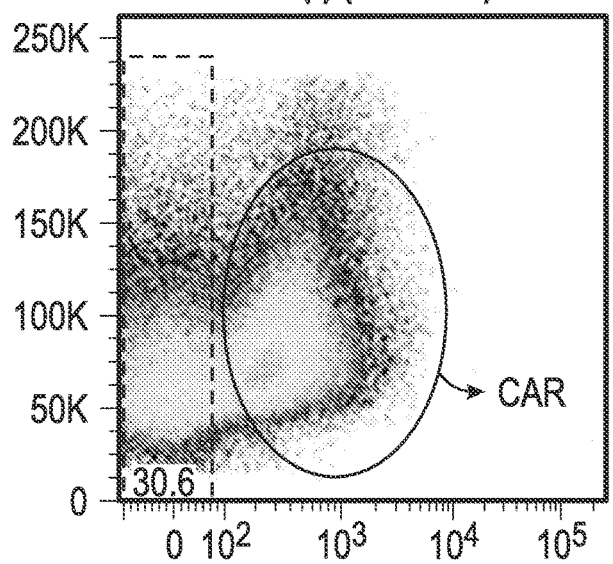
Figure 11C:
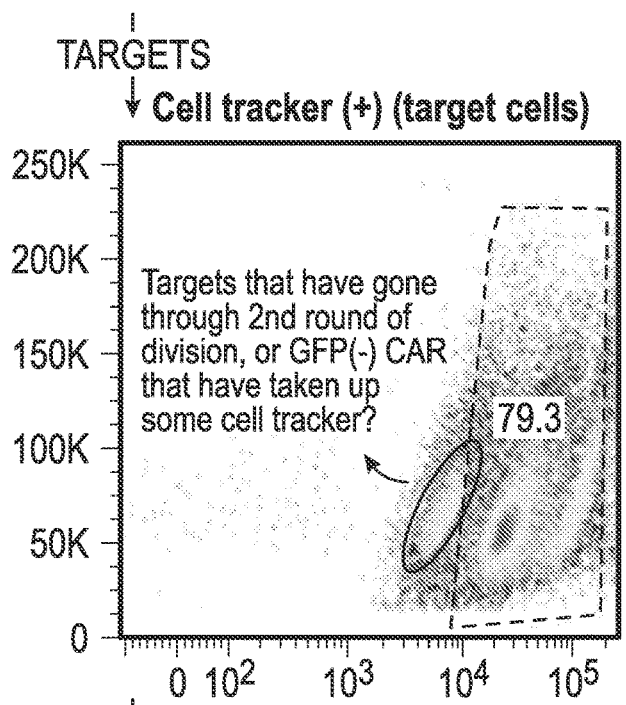
Figure 11D:
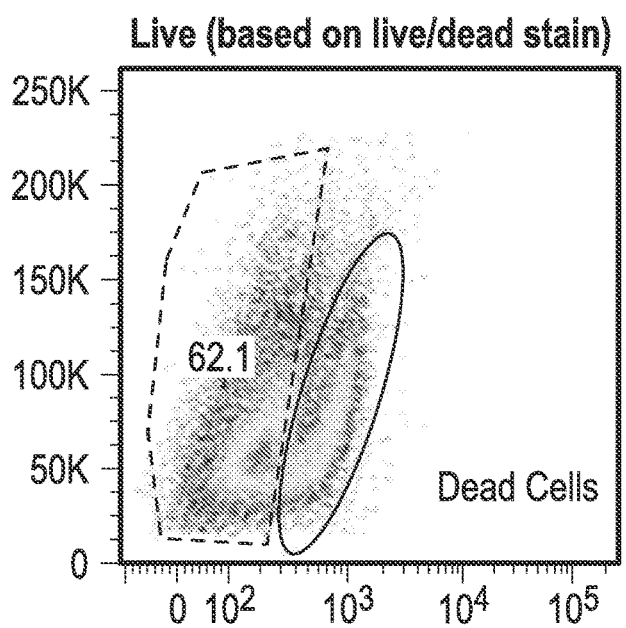

Anti-HIV CAR+ T-cells can be used to target HIV infected cells for killing. Attention is drawn to FIG. 10, which show a graphical representation of the secretion of IFNγ when Anti-HIV CAR+ T-cells are activated in the presence of HIV infected T-cells. In the experiment, T-cells expressing Anti-HIV CARs comprising scFv derived from PGT145, a co-stimulatory domain, and controlled by a promoter were incubated with HIV infected T-cells. As a control, T-cells carrying mock CAR were incubated with HIV infected T-cells. Experiments were run in duplicate. IFNγ is known to be secreted early in the immune response. A standard curve was generated using concentrations of IFNγ at 31 pg/μl, 62 pg/μl, 125 pg/μl, 250 pg/μl, 0.5 ng/μl, and 1 ng/μl to obtain a standard curve of concentration vs OD at 280 nm. IFNγ expression was measured for wells carrying a blank, unstimulated HIV positive cells, stimulated HIV positive cells, HIV negative cells, stimulated HIV negative cells, T-cells expressing CARPGT145 controlled by an EF1a promoter, T-cells expressing CARPGT145 controlled by an MND promoter, T-cells with expressing a mock CAR, unstimulated HIV+ cells mixed with T cells expressing CARPGT145 under a EF1 promoter, unstimulated HIV positive cells mixed with T-cells carrying CARPGT145 under an MND promoter, unstimulated HIV positive cells mixed with T-cells carrying a mock CAR, stimulated HIV+ cells mixed with T cells expressing CARPGT145 under a EF1 promoter, stimulated HIV positive cells mixed with T-cells carrying CARPGT145 under an MND promoter, stimulated HIV positive cells mixed with T-cells carrying a mock CAR, unstimulated HIV negative cells mixed with T cells expressing CARPGT145 under a EF1 promoter, unstimulated HIV negative cells mixed with T-cells carrying CARPGT145 under an MND promoter, unstimulated HIV negative cells mixed with T-cells carrying a mock CAR, stimulated HIV negative cells mixed with T cells expressing CARPGT145 under a EF1 promoter, stimulated HIV negative cells mixed with T-cells carrying CARPGT145 under an MND promoter, and stimulated HIV negative cells mixed with T-cells carrying a mock CAR. As shown from FIG. 4, in comparison with the standard curve, the highest inducer of IFNγ are the T-cells that express CARPGT145 under the control of an MND promoter, with a production of IFNγ at about roughly 1.5 ng/μl in the presence of stimulated HIV positive cells. In comparison to the standard curve, T-cells that express CARPGT145 under the control of an EF1a promoter in the presence of stimulated HIV positive cells can induce production of IFNγ at about 1 ng/μl, and T-cells that express mock CAR can be induced to produce IFNγ at about 0.4 ng/μl in the presence of stimulated HIV positive cells. It can be concluded that the production of IFNγ is specifically induced in T-cells carrying CARs comprising scFv of strong neutralizing antibodies of HIV are specifically activated in the presence of HIV positive cells.

Quantification of Anti-CAR Killing of HIV Infected Cells.

Anti-HIV CARPG9 T-cells can be used to target HIV infected cells for killing. For the experiment, CARPG9 expressing T-cells were mixed with HIV infected cell lines, and assayed for the quantification of anti-HIV CARPG9 killing of HIV positive cells. The CARPG9 expressing T cells contained GFP and the target T-cells were loaded with fluorescent Cell Tracker (Invitrogen). As shown in FIG. 11, flow cytometry was used to separate the target cells (GFP (−)) and the CAR expressing T-cells (GFP(+)). In panel 1, live cells are shown on a forward and side light scattering. Panel 2 shows the CAR expressing T-cells and the target cells carrying the tracker (HIV positive cells). As the cells go into the second round of division, a small percentage is shown of some CAR expressing cells (GFP+) taking up some cell tracker, but there is also a decrease in the target cells carrying the tracker. As shown in the fourth panel, there are dead cells over time due to the presence of activated T-cells carrying the anti-HIV CARPG9 leading to the killing of the HIV positive target cells. HIV DNA in the combined cell culture is extracted and the HIV DNA is quantified, and as expected anti-CAR carrying T-cells killing HIV infected cells leads to the decrease of HIV DNA in the cell culture.

Activity of Anti-HIV CAR Carrying T Cells from CARPG9 and CARPGT128

Figure 12:
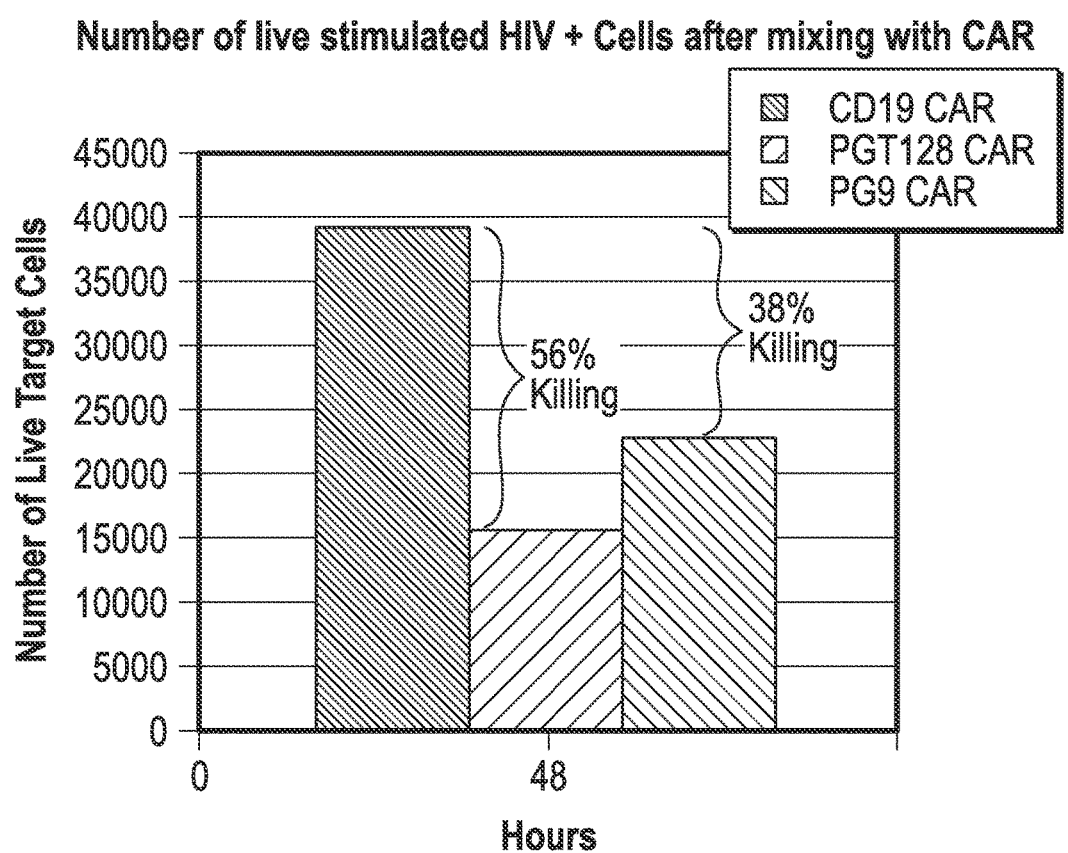
FIG. 12 is a graphical representation of results from cell killing assays. Shown are the number of live target-cells after mixing with either CD19 CAR, PGT128 CAR, or GP9 CAR. The killing of HIV+ cells by anti-HIV CAR (PG9 and PGT128-derived) was quantified in comparison to the number of target cells that survived when cultured with a non-specific CD19 CAR. The graphs represent the median cell killing of three cell killing assays that were run in triplicate for 48 hours. These experiments were performed in the presence of antiretrovirals.

Anti-HIV CARPG9 and CARPGT128 carrying T-cells were used to target HIV infected cells for killing. As shown in FIG. 12, Anti-HIV CAR+ T-cells are activated in the presence of HIV infected T-cells after incubation for 48 hours. Experiments were carried out in triplicate. In the experiment, T-cells expressing Anti-HIV CARs comprising scFv derived from PGT9 or PGT128, were mixed with HIV positive cells. As a control HIV positive cells were incubated with T cells carrying CARCD19. As shown in FIG. 6, all reactions started with the same number of HIV-infected target cells, and there were about 40,000 live HIV-infected target cells after 48 hours of incubation with CARCD19 T-cells. However, when HIV positive cells were mixed with CARPGT128 T-cells there were 15,000 viable HIV-infected cells at 48 hours, indicating that 56% of the HIV-infected cells were killed; and when HIV positive cells were mixed with CARPG9 T-cells there were 20,000 viable HIV-infected cells at 48 hours, indicating that 38% of the HIV-infected were killed. The results indicate killing of HIV-infected cells is a specific function of T-cells carrying anti-HIV CARs. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Anti-HIV CAR PGT145+ T-Cells Kill HIV-Infected Cells

Figure 13A:
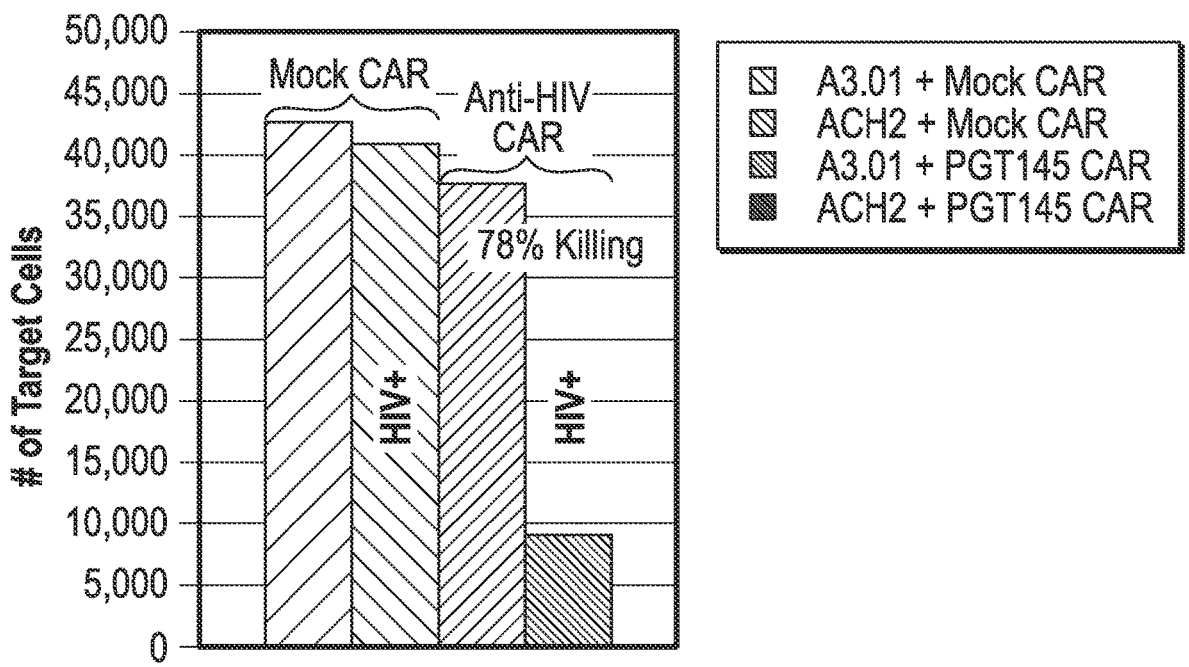
FIG. 13 shows a series of graphical representations of PGT145 based anti-HIV CAR induced killing of HIV infected cells. The graphs represent the median cell killing of three killing assays that were run in triplicate for 72 hours. Similar results were obtained in separate experiments (not represented). All experiments were performed in the presence of antiretrovirals.
Figure 13B:
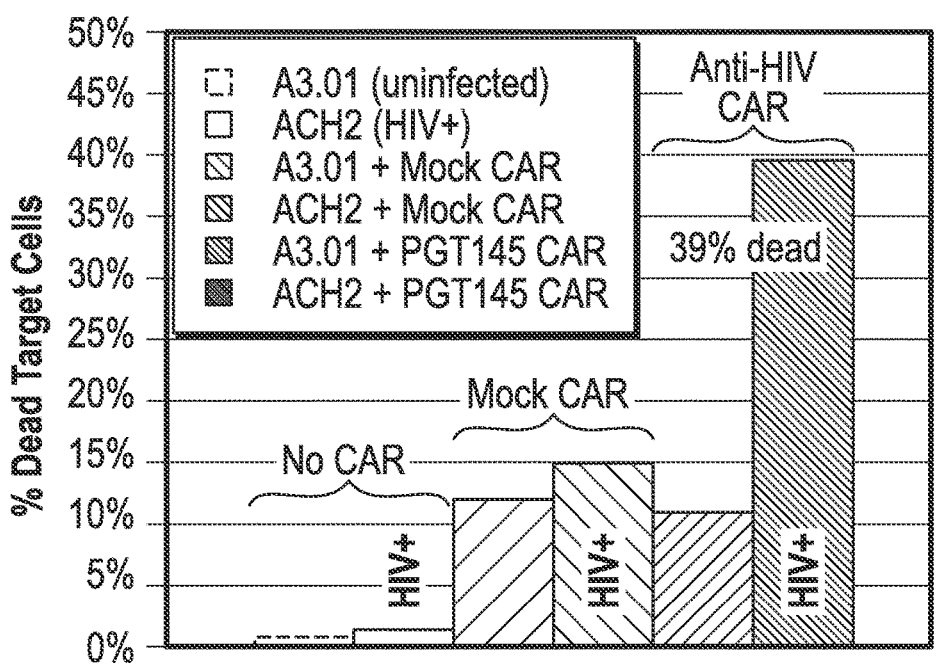

T-cells carrying anti-HIV CARPGT145 were used to induce the killing of HIV infected cells. In FIG. 13, the two graphs indicate the number of target cells and the percent dead target cells respectively. The experiments were carried out in triplicate and the graphs are representative of two experiments. As shown in the first graph, T-cells carrying a mock CAR were incubated with uninfected cells and HIV infected cells and show a target cell count of 40,000 live cells. However in the presence of T-cells carrying anti-HIV CARPGT145, the control uninfected cells were not affected by the presence of the T-cells carrying anti-HIV CAR-PGT145 (dark blue). But in the presence of HIV-infected cells, T-cells carrying anti-HIV CARPGT145 are activated and result in the number of target cells being decreased to less than 10,000, indicating a 78% killing in the presence of T-cells carrying anti-HIV CARPGT145. As shown in the right panel, not only is the number of HIV-infected cells decreased, but the percent of HIV-infected target cells that stain as dead is increased when they are cultured with T-cells carrying anti-HIV CARPGT145, indicating a specificity for the T-cells carrying anti-HIV CARPGT145 only to HIV positive cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Figure 14:
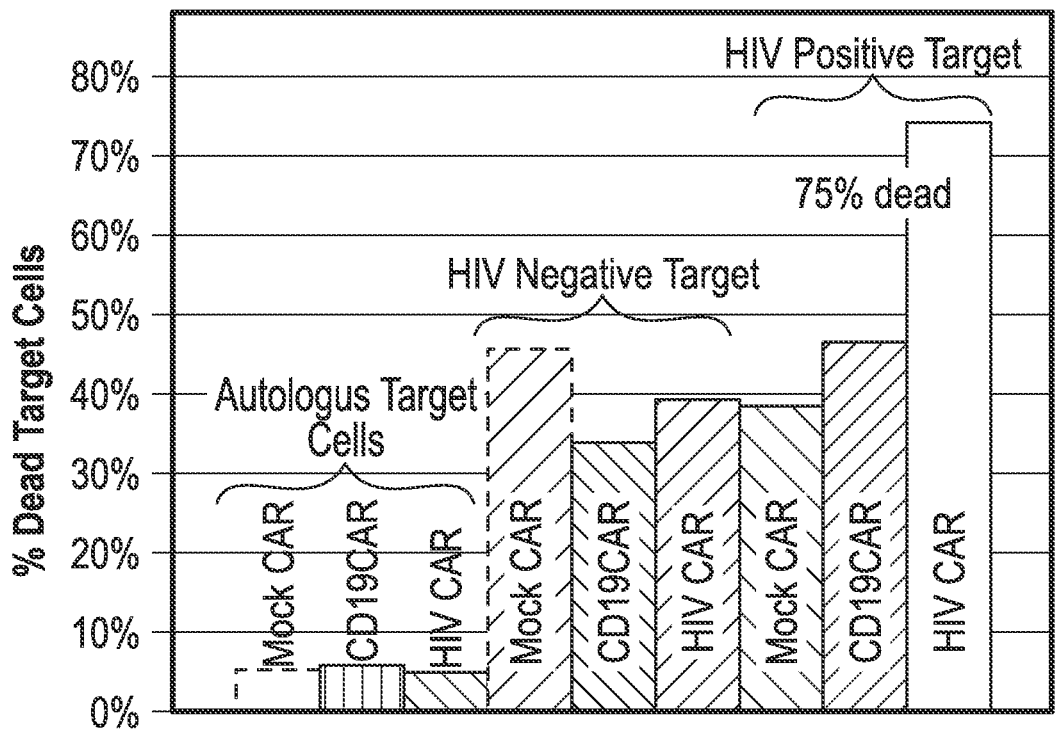
FIG. 14 is a graphical representation of the percentage of HIV-infected cells that stain as dead when mixed with cells with anti-HIV CAR that utilize the EF1a promoter. The cell killing assay was run in triplicate and analyzed by flow cytometry at 72 hours. As shown, when HIV-infected target-cells are mixed with anti-HIV CAR a large percentage of the HIV-infected cells stain as dead (75%). Autologous and non-autologous HIV-negative target cells were used as controls. As shown, the autologous target cells had a much lower percentage of cells that stain as dead. These experiments were carried out in the presence of antiretrovirals.

Anti-HIV CAR PGT145+ T-Cells Under Control of an EF1a Promoter Induce Death of HIV-Infected Cells The effect of the EF1a promoter on T-cells carrying anti-HIV CARPGT145 was tested by targeting HIV-infected cells for killing. Cell killing assays were run in triplicate in at least two separate experiments. For all experiments, T cells carrying mock CAR, CARCD19, and anti-HIV CAR under an EF1a promoter were used for cell killing. As shown in FIG. 14, when CAR carrying T-cells were exposed to autologous target cells, there was less than 5% cell killing (control). However in the presence of HIV negative target cells, cell killing for all CAR expressing T-cells ranged from 40 to 45% cell killing. In the presence of HIV positive cells, only the T-cell expressing anti-HIV CAR under the EF1a promoter showed an increase of cell killing at 75% killing indicating that T-cells expressing anti-HIV CAR under a EF1a promoter is specifically activated only in the presence of HIV positive cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Figure 15:
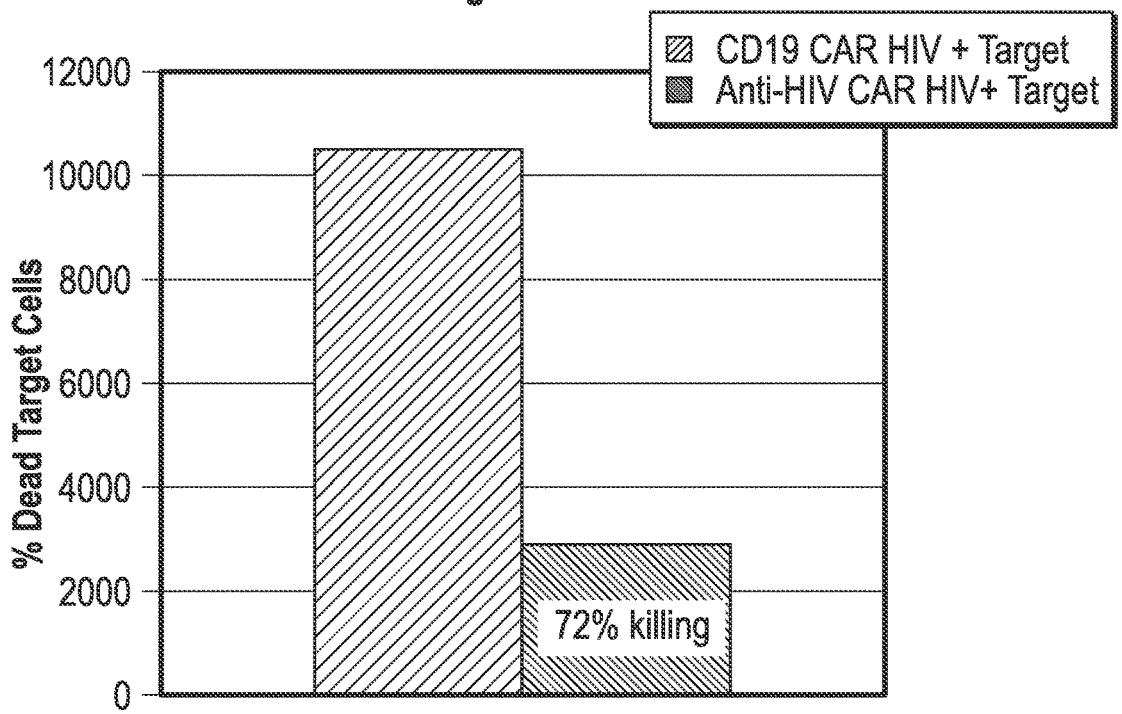
FIG. 15 is a graphical representation of cell killing with anti-HIV CAR comprising an EF1a promoter. As shown, the cells with the anti-HIV CAR kill 72% of the HIV-infected target cells, compared to the number of HIV+ target cells present when cultured with cells that have an anti-CD19 CAR. These experiments were done in the presence of antiretrovirals.

Anti-HIV CARPGT145+ T-Cells Under Control of an EF1a Promoter Reduce the Number of HIV-Infected Cells HIV-infected cells were exposed to T-cells modified to contain the anti-HIV CARPG9 to examine cell killing. As a control, HIV positive cells were also exposed to a control T-cell carrying a non-specific CAR (CARCD19) in the presence of a EF1 promoter. As shown in FIG. 15, after 72 hours 72% of the HIV-infected target cells were killed when mixed with the anti-HIV CARPG9 compared to the non-specific CARCD19. From the experiment, the indication is that T-cells carrying anti-HIV CAR under the control of a EF1 promoter are specifically activated and induced to kill HIV-infected cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Figure 16:
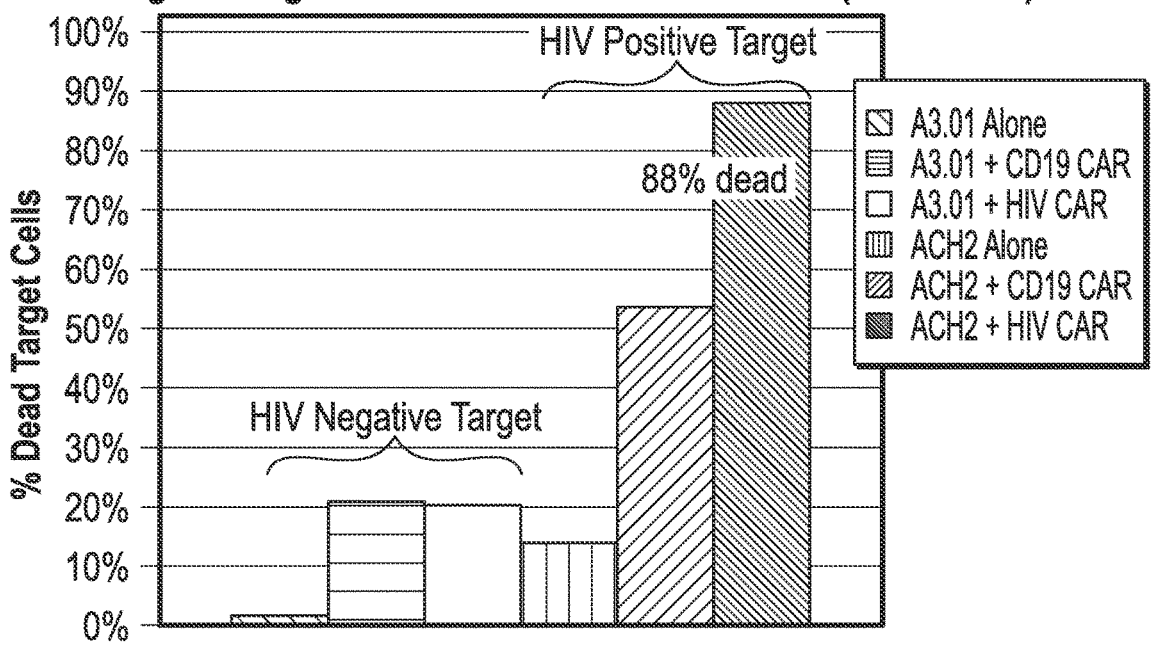
FIG. 16 is a graphical representation of the percentage of HIV-infected cells that stain as dead when mixed with cells with anti-HIV CAR that utilize the MND promoter. The cell killing assay was run in triplicate and analyzed by flow cytometry at 72 hours. As shown when HIV-infected target-cells are mixed with anti-HIV CAR a large percentage of the HIV-infected cells stain as dead (88%). These experiments were carried out in the presence of antiretrovirals.

Anti-HIV CARPGT145+ T-Cells Under Control of an MND Promoter Induce Death of HIV-Infected Cells Cell killing assays were run with HIV positive and negative cells using T-cells carrying Anti-HIV CAR under the control of an MND promoter. For the experiment, HIV infected and uninfected targets cells were incubated with either control T-cells carrying CARCD19 or T-cells carrying anti-HIV CAR under control of an MND promoter for 72 hours. Cells were stained and assessed by flow cytometry to determine what percentage of target cells stained as dead/dying. As shown in FIG. 16, about 20% of the control HIV negative cells stain as dead when exposed to CAR expressing T cells. However, when HIV positive cells were exposed to T-cells expressing anti-HIV CAR under the MND promoter, about 88% target cells stain as dead/dying. The results indicate that cell killing is specific for T-cells expressing anti-HIV CAR under the control of an MND promoter, and that activation is only seen when the CAR expressing T-cell is exposed to HIV positive cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Figure 17:
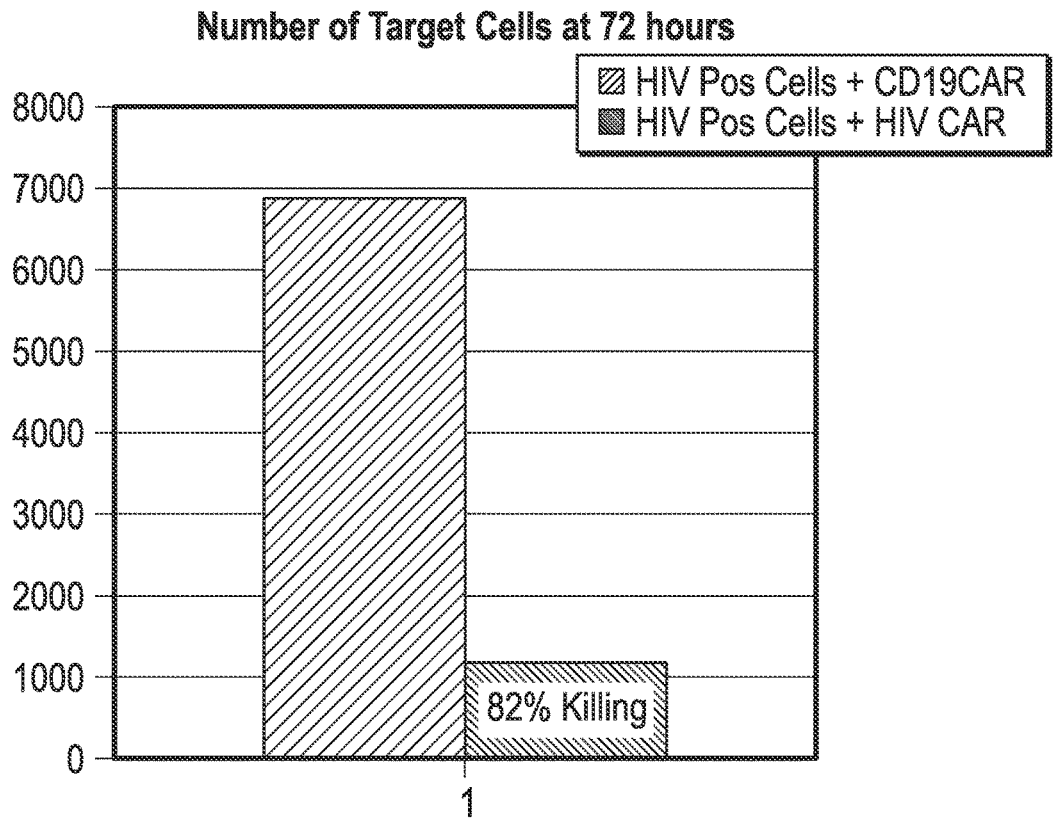
FIG. 17 is a graphical representation of cell killing with anti-HIV CAR comprising an MND promoter. As shown, the cells with the anti-HIV CAR kill 82% of the HIV-infected target cells, compared to the number of HIV+ target cells present when cultured with cells that have an anti-CD19 CAR. These experiments were performed in the presence of antiretrovirals.

Anti-HIV CARPGT145+ T-Cells Under Control of an MND Promoter Reduced the Number of HIV-Infected Cells Anti-HIV CAR+ T-cells can be used to target HIV infected cells for killing. As shown in FIG. 17, the control T-cells carrying CARCD19 were incubated with HIV positive cells for 72 hours and exhibited a cell count number of approximately 7000. However, anti-HIV CAR+ T-cells under an MND promoter were activated in the presence of HIV infected T-cells and at 72 hours of exposure led to an 82% cell killing (cell count at 1000) indicating that T cells expressing anti-HIV CAR under a MND promoter are specifically activated and induce killing of HIV positive cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Figure 18:
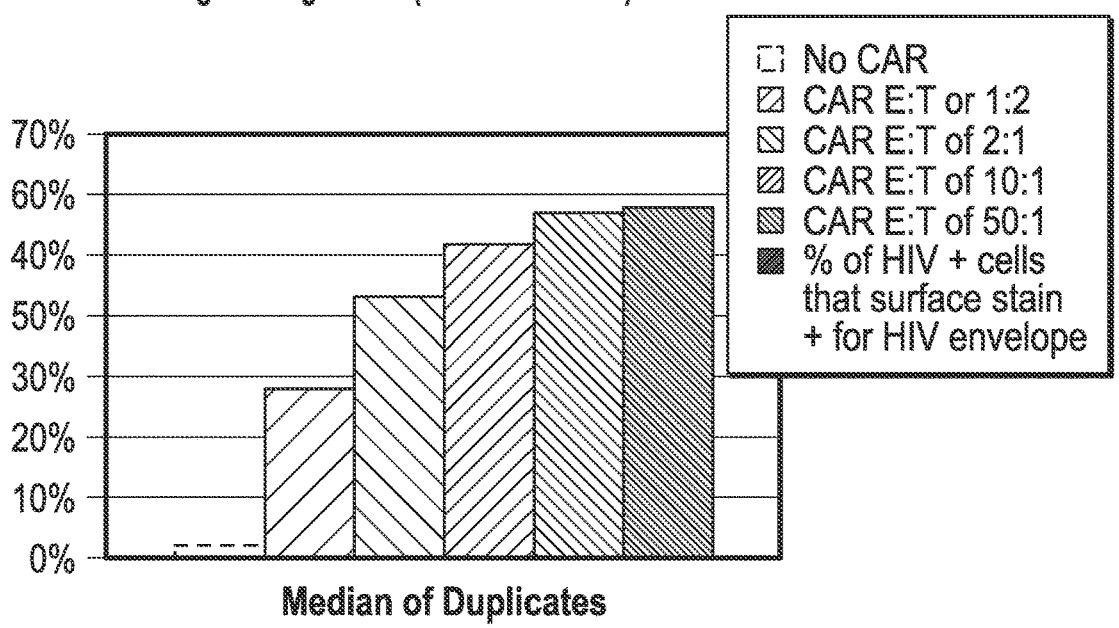
FIG. 18: graphically summarizes dose response data showing the percentage of HIV infected target-cells that stain as dead when exposed to an increasing ratio of cells with anti-HIV CARs. The percentage of HIV-infected target cells that stain dead are shown in comparison to the percentage of cells that stain positive for HIV envelope at the cell surface. The experiment shows the average result of duplicate results, measured by flow cytometry at 36 hours. These experiments were done in the presence of antiretrovirals.

Dose Response of Anti-HIV CAR Carrying T-Cells in the Presence of HIV Infected Cells Anti-HIV CAR+T-cells can be used to target HIV infected cells for killing. In order to test for dose response of T-cells carrying anti-HIV CARs, ratios of T-cells carrying anti-HIV CARs to HIV positive cells were carried out at 36 hours and the cells were stained and assessed by flow cytometry in order to identify dead cells. The ratios of anti-HIV CAR carrying T-cells to HIV infected cells were as follows: 1:2, 2:1, 10:1 and 50:1. As shown in FIG. 18, Anti-HIV CAR+ T-cells are activated in the presence of HIV infected T-cells, and lead to more killing of HIV-infected cells in a dose dependent manner. At the 50:1 ratio the anti-HIV CAR are able to kill almost the same percentage of cells that express detectable HIV envelope at the cell surface, suggesting that at higher concentrations the cells with anti-HIV CAR are capable of killing almost all HIV-expressing cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Kinetics of Anti-HIV CAR Killing

Figure 19A:
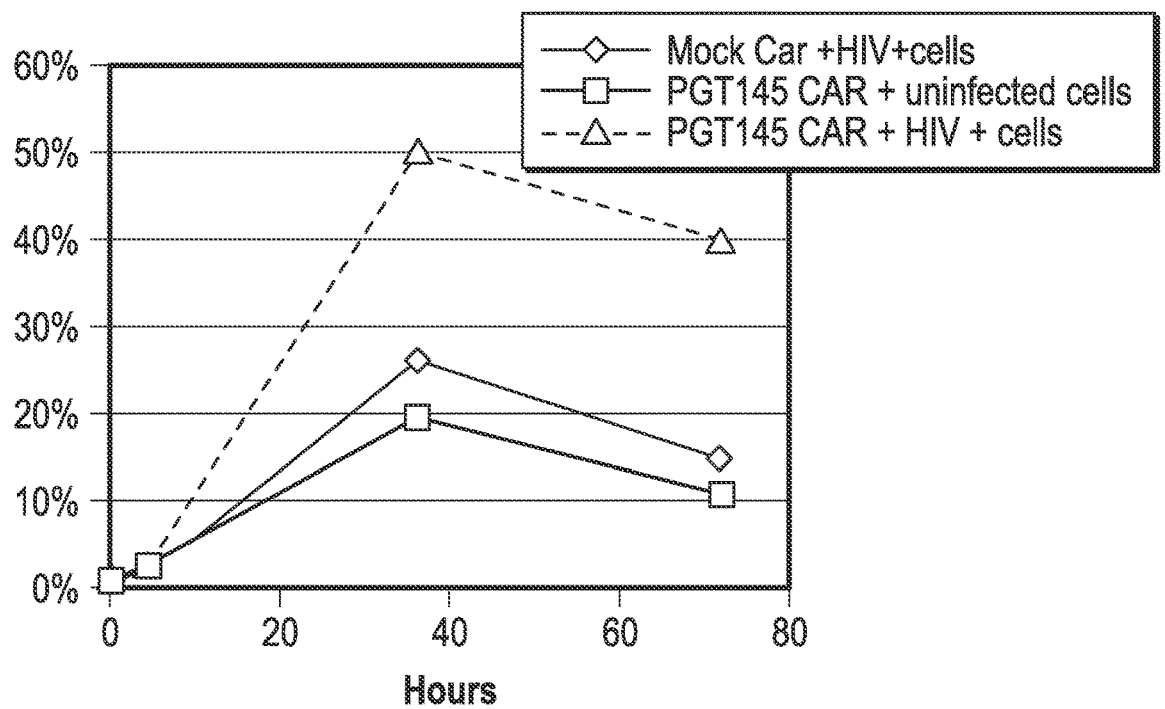
FIG. 19 is a graphs depicting kinetics of anti-HIV CAR killing. Graphs depict the percentage of HIV-infected target cells that stain as dead and the number of remaining HIV-infected target cells, as assessed by flow cytometry over 72 hours compared to controls. These experiments were performed in the presence of antiretrovirals.
Figure 19B:
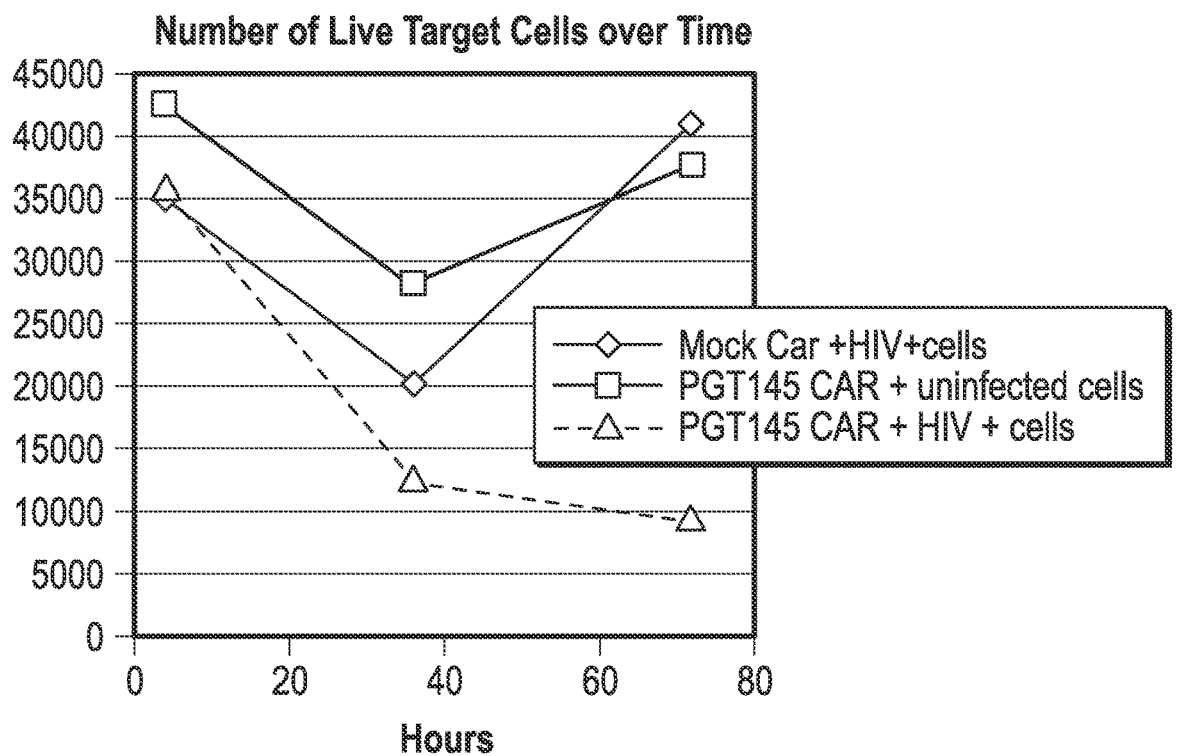

As shown in FIG. 19, the kinetics of anti-HIV CAR killing was examined using T-cells carrying the anti-HIV CARPGT145 or mock transduced T-cells mixed with HIV-infected or HIV-uninfected cells. Cell killing was examined at 36 hours and 72 hours. As shown from both controls (mock transduced T-cells mixed with HIV positive cells, and anti-HIV CAR mixed with HIV negative cells), the percentage of target cells that stained as dead/dying was at 20 to 25% and then 10-15%, respectively. However, when anti-HIV CAR expressing T-cells were exposed to HIV positive cells at 36 and 72 hours cell killing was at 50% and 40%, respectively. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Figure 20:
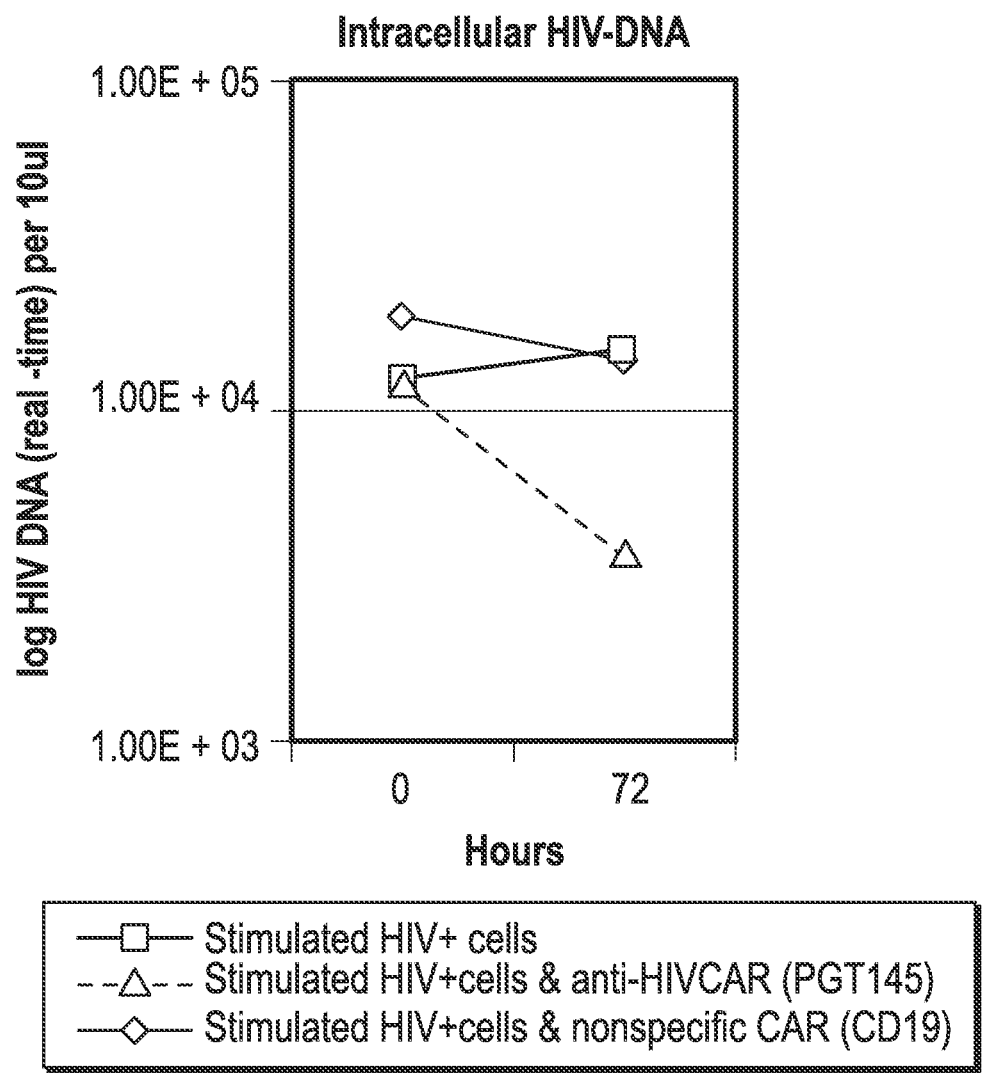
FIG. 20 graphically summarizes the results of quantitative HIV PCR experiments determining the amount of HIV DNA in the cell culture after exposure to CAR+ cells. These experiments were carried out in the presence of antiretrovirals.

Quantitative HIV PCR to Determine the Amount of HIV DNA Present after Exposure of HIV Positive Cells to Anti-HIV CAR Expressing T-Cells In order to assess the killing of HIV-infected cells by cells expressing anti-HIV CAR, the intracellular HIV DNA was quantified. Stimulated HIV positive T-cells were exposed to T-cells carrying either anti-HIV CAR or CARCD19. As shown in FIG. 20, quantitative PCR (qPCR) was run on samples of supernatant from 3 groups: Stimulated HIV positive cells, stimulated HIV positive cells in the presence of anti-HIV CARPGT145 expressing T cells, and a control sample with stimulated HIV positive cells in the presence of anti-HIV CARCD19 expressing T cells. As shown, after 72 hours, there is a substantial decrease in the amount of HIV DNA present in the supernatant after exposure of the HIV positive cells to anti-HIV CARPGT145 expressing T cells, indicating that the activity of the anti-HIV CARPGT145 expressing T cells is due to the presence of the HIV positive cells, and lead to the specific targeting and killing of the HIV positive cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Anti-HIV CAR Function as Measured by the Amount of HIV DNA

Figure 21:
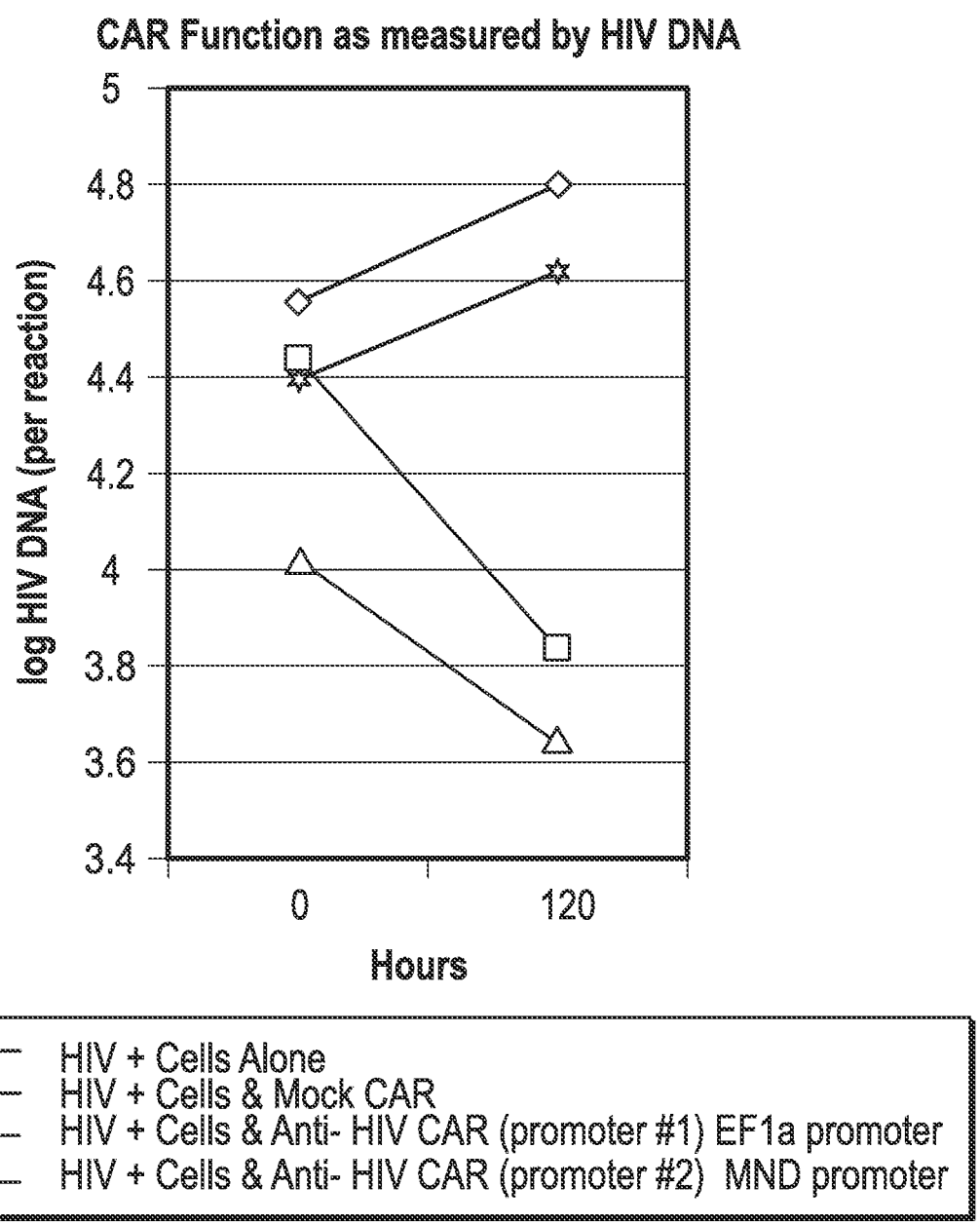
FIG. 21 is a graph depicting the CAR function as measured by the quantitated amount of HIV DNA. Experiments were done in the presence of antiretrovirals.

In order to assess the amount of cell killing, the intracellular HIV DNA in the mixed cell culture was examined after exposure of HIV positive cells to anti-CAR expressing T-cells that were under control of either an EF1a promoter or an MND promoter region. As shown in FIG. 21, the samples in these experiments were tested for the presence of HIV DNA. In the samples of HIV positive cells alone, HIV-infected cells mixed with mock-CAR expressing T-cells, HIV-infected cells mixed with anti-HIV CAR expressing T-cells under control of an EF1a promoter, and HIV-infected cells mixed with anti-HIV CAR expressing T-cells under control of an MND promoter. As shown from the HIV DNA measurement after 120 hours of exposure, the HIV cells alone and the HIV cells mixed with mock-CAR control had an increase in intracellular viral DNA. However after exposure to the anti-HIV CAR expressing T-cells, there was a substantial decrease in the amount of intracellular HIV DNA, indicative of specific targeting of HIV positive cells by anti-HIV CAR expressing T-cells. This experiment was done in the presence of three-drug combination antiretroviral therapy, which inhibits infection of new cells but doesn't inhibit expression of virus from previously infected cells, implying that the anti-HIV CAR can kill infected cells that express HIV despite the presence of antiretroviral therapy.

Anti-HIV CAR Function in the Absence of Antiretrovirals

Figure 22:
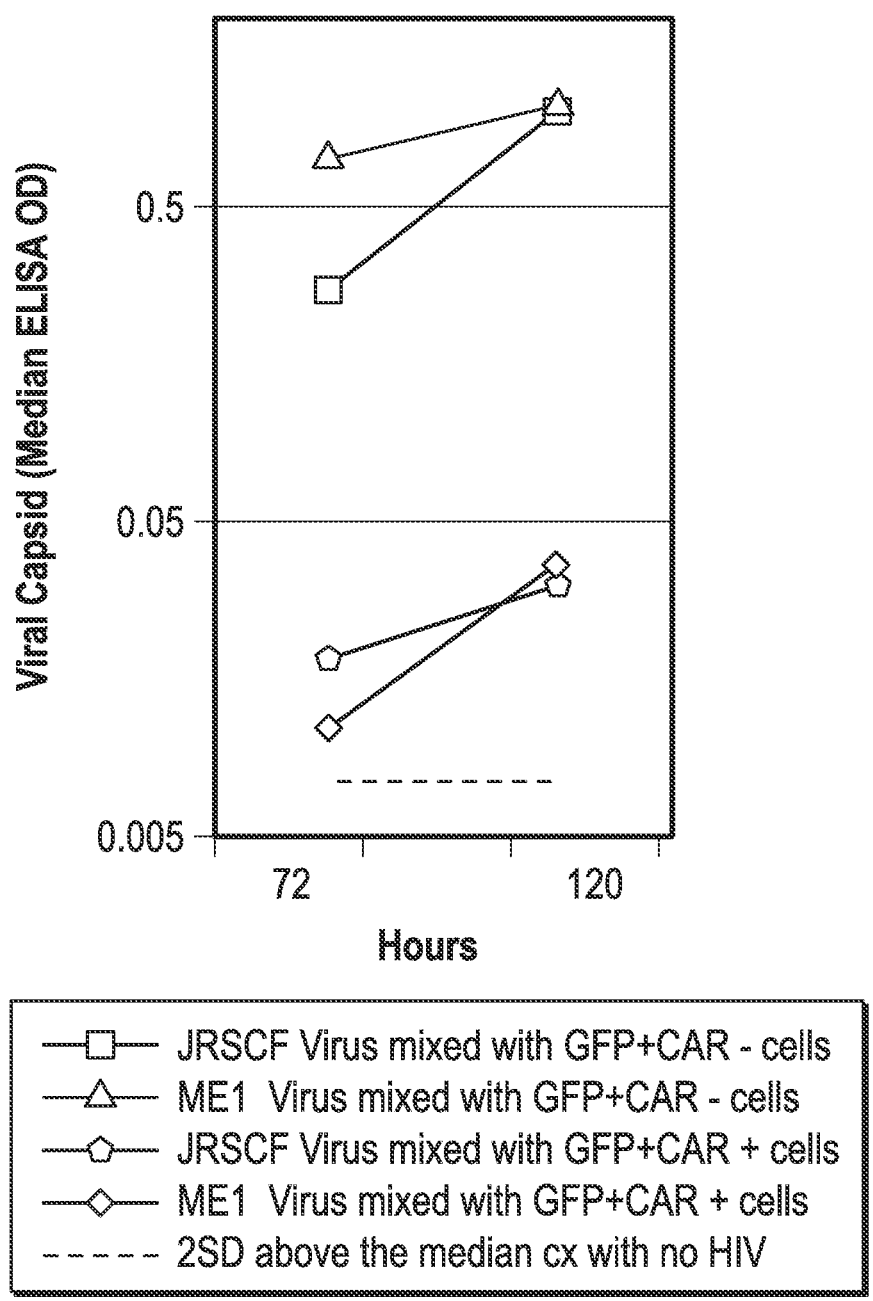
FIG. 22 is a graph depicting the amount of HIV protein detected over time in the presence of cells that do or do not contain an anti-HIV CAR. This figure shows a subset of the data presented at FIG. 4. Two different HIV strains (JRCSF and ME1) demonstrate more than a log decrease in HIV viral protein at 72 and 120 hours of culture when grown in the presence of cells that contain an anti-HIV CAR. This experiment was done in the absence of antiretrovirals.

As shown in FIG. 22, anti-HIV CAR are capable of reducing the amount of HIV that grows in culture in the absence of antiretrovirals. Two different HIV viruses (JRCSF and ME1) were grown in the donor cells for approximately three days and then mixed with allogenic cells engineered to express either GFP plus an anti-HIV CAR (CARPGT145) or GFP and no CAR (negative control). In both cases, at 72 and 120 hours, the amount of HIV protein detected was more than a log less when cells with an anti-HIV CAR (CARPGT145) were added versus when cells without an anti-HIV CAR was added. Unlike previous figures this figure shows that that anti-HIV CAR are able to decrease the amount of HIV capsid protein (p24) produce in viral culture.

It is understood that the examples and alternatives described herein are for illustrative purposes only and that various modifications or changes in light thereof will be suggested to persons skilled in the art and are to be included within the spirit and purview of this application and scope of any appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to alternatives containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method of genetically modifying a T-cell comprising a chimeric antigen receptor, wherein said T-cell lacks a co-receptor for HIV, the method comprising:
   delivering a nucleic acid sequence encoding a chimeric antigen receptor to a T-cell, wherein the chimeric antigen receptor comprises a signal peptide, an antigen-binding domain comprising an amino acid sequence selected from SEQ ID NO:01, SEQ ID NO:02, or SEQ ID NO:03, a spacer configured to improve binding to a target cell, a transmembrane CD8 hinge domain, and a co-stimulatory domain; and
   disrupting a gene encoding a co-receptor for HIV in the T-cell.

2. The method of claim 1, wherein the co-stimulatory domain is CD137.

3. The method of claim 1, wherein the transmembrane CD8 hinge region is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 amino acids in length or a length within a range defined by any two of the aforementioned lengths.

4. The method of claim 1, wherein the disrupting is performed by a nuclease for targeted genome modification.

5. The method of claim 4, wherein the nuclease is an engineered nuclease, a cleaving nuclease, a zinc finger nuclease, a transcription activator-like effector nuclease, meganuclease, a homing endonuclease, or a clustered regularly interspaced short palindromic or repeat RNA guided nuclease, or a portion thereof.

6. The method of claim 1, wherein the co-receptor is a co-receptor for HIV entry.

7. The method of claim 6, wherein the co-receptor is CCR3, CXCR4 or CCR5.

8. The method of claim 7, wherein the co-receptor is CCR5.

9. The method of claim 1, wherein the cell is a CD4+ or a CD8+ T-cell.

10. The method of claim 1, wherein delivering the nucleic acid sequence encoding a chimeric antigen receptor to the T-cell is performed by transduction with a lentiviral system.

11. The method of claim 1, wherein the antigen-binding domain comprises the amino acid sequence of SEQ ID NO:01.

12. The method of claim 1, wherein the antigen-binding domain comprises the amino acid sequence of SEQ ID NO:03.

13. A method of genetically modifying a T-cell comprising a chimeric antigen receptor, wherein said T-cell lacks a co-receptor for HIV, the method comprising:
   delivering a nucleic acid sequence encoding a chimeric antigen receptor to a T-cell, wherein the chimeric antigen receptor comprises a signal peptide, an antigen-binding domain comprising an amino acid sequence selected from SEQ ID NO:01, SEQ ID NO:02, or SEQ ID NO:03, a spacer configured to improve binding to a target cell, a transmembrane CD8 hinge domain, and a co-stimulatory domain or an intracellular domain of a T-cell receptor; and
   disrupting a gene encoding a co-receptor for HIV in the T-cell.

14. The method of claim 13, wherein the antigen-binding domain comprises the amino acid sequence of SEQ ID NO:01.

15. The method of claim 13, wherein the antigen-binding domain comprises the amino acid sequence of SEQ ID NO:02.

16. The method of claim 13, wherein the antigen-binding domain comprises the amino acid sequence of SEQ ID NO:03.

17. The method of claim 1, wherein the antigen-binding domain comprises the amino acid sequence of SEQ ID NO:02.

18. The method of claim 5, wherein the nuclease is a clustered regularly interspaced short palindromic or repeat RNA guided nuclease.

19. The method of claim 5, wherein the nuclease is a zinc finger nuclease.

20. The method of claim 5, wherein the nuclease is a transcription activator-like effector nuclease.

21. The method of claim 5, wherein the nuclease is a homing endonuclease.

22. The method of claim 5, wherein the nuclease is a meganuclease.

23. The method of claim 7, wherein the co-receptor is CCR3.

24. The method of claim 7, wherein the co-receptor is CXCR4.

25. The method of claim 9, wherein the cell is a CD4+ T-cell.

26. The method of claim 9, wherein the cell is a CD8+ T-cell.

* * * * *

SEQUENCE LISTING

<160> NUMBER OF SEQ ID NOS: 15

<210> SEQ ID NO 1
<211> LENGTH: 257
<212> TYPE: PRT
<213> ORGANISM: Artificial Sequence
<220> FEATURE:
<223> OTHER INFORMATION: PGT128-scFV

<400> SEQUENCE: 1

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

-continued

```
Ala Val Tyr Tyr Cys Gly Ser Leu Val Gly Asn Trp Asp Val Ile Phe
                85                  90                  95
Gly Gly Gly Thr Lys Leu Thr Val Leu Arg Ser Gly Gly Gly Gly Ser
            100                 105                 110
Gly Gly Gly Gly Ser Gly Gly Gly Ser Gln Pro Gln Leu Gln Glu
            115                 120                 125
Ser Gly Pro Thr Leu Val Glu Ala Ser Glu Thr Leu Ser Leu Thr Cys
130                 135                 140
Ala Val Ser Gly Asp Ser Thr Ala Ala Cys Asn Ser Phe Trp Gly Trp
145                 150                 155                 160
Val Arg Gln Pro Pro Gly Lys Gly Leu Glu Trp Val Gly Ser Leu Ser
                165                 170                 175
His Cys Ala Ser Tyr Trp Asn Arg Gly Trp Thr Tyr His Asn Pro Ser
            180                 185                 190
Leu Lys Ser Arg Leu Thr Leu Ala Leu Asp Thr Pro Lys Asn Leu Val
            195                 200                 205
Phe Leu Lys Leu Asn Ser Val Thr Ala Ala Asp Thr Ala Thr Tyr Tyr
        210                 215                 220
Cys Ala Arg Phe Gly Gly Glu Val Leu Arg Tyr Thr Asp Trp Pro Lys
225                 230                 235                 240
Pro Ala Trp Val Asp Leu Trp Gly Arg Gly Thr Leu Val Thr Val Ser
                245                 250                 255
Ser

<210> SEQ ID NO 2
<211> LENGTH: 263
<212> TYPE: PRT
<213> ORGANISM: Artificial Sequence
<220> FEATURE:
<223> OTHER INFORMATION: PGT9-scFV

<400> SEQUENCE: 2

Gln Ser Ala Leu Thr Gln Pro Ala Ser Val Ser Gly Ser Pro Gly Gln
1               5                   10                  15
Ser Ile Thr Ile Ser Cys Asn Gly Thr Ser Asn Asp Val Gly Gly Tyr
                20                  25                  30
Glu Ser Val Ser Trp Tyr Gln Gln His Pro Gly Lys Ala Pro Lys Val
            35                  40                  45
Val Ile Tyr Asp Val Ser Lys Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Gly Asp Tyr Tyr Cys Lys Ser Leu Thr Ser Thr
                85                  90                  95
Arg Arg Arg Val Phe Gly Thr Gly Thr Lys Leu Thr Val Leu Arg Ser
            100                 105                 110
Gly Gly Gly Gly Ser Gly Gly Gly Gly Ser Gly Gly Gly Gly Ser Gln
            115                 120                 125
Arg Leu Val Glu Ser Gly Gly Val Val Gln Pro Gly Ser Ser Leu
130                 135                 140
Arg Leu Ser Cys Ala Ala Ser Gly Phe Asp Phe Ser Arg Gln Gly Met
145                 150                 155                 160
His Trp Val Arg Gln Ala Pro Gly Gln Gly Leu Glu Trp Val Ala Phe
                165                 170                 175
```

-continued

```
Ile Lys Tyr Asp Gly Ser Glu Lys Tyr His Ala Asp Ser Val Trp Gly
            180                 185                 190

Arg Leu Ser Ile Ser Arg Asp Asn Ser Lys Thr Leu Tyr Leu Gln
        195                 200                 205

Met Asn Ser Leu Arg Val Glu Asp Thr Ala Thr Tyr Phe Cys Val Arg
    210                 215                 220

Glu Ala Gly Gly Pro Asp Tyr Arg Asn Gly Tyr Asn Tyr Tyr Asp Phe
225                 230                 235                 240

Tyr Asp Gly Tyr Tyr Asn Tyr His Tyr Met Asp Val Trp Gly Lys Gly
                245                 250                 255

Thr Thr Val Thr Val Ser Ser
            260
```

<210> SEQ ID NO 3
<211> LENGTH: 269
<212> TYPE: PRT
<213> ORGANISM: Artificial Sequence
<220> FEATURE:
<223> OTHER INFORMATION: PGT145-scFV

<400> SEQUENCE: 3

```
Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
            20                  25                  30

Thr Gly Ala Asn Tyr Leu Ala Trp Tyr Leu Gln Arg Pro Gly Gln Thr
        35                  40                  45

Pro Arg Leu Leu Ile His Leu Ala Thr His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Asp Asp Val Gly Thr Tyr Tyr Cys Met Gln Gly
                85                  90                  95

Leu His Ser Pro Trp Thr Phe Gly Gln Gly Thr Lys Val Glu Ile Lys
            100                 105                 110

Arg Ser Gly Gly Gly Gly Ser Gly Gly Gly Gly Ser Gly Gly Gly Gly
        115                 120                 125

Ser Gln Val Gln Leu Val Gln Ser Gly Ala Glu Val Lys Lys Pro Gly
    130                 135                 140

Ser Ser Val Lys Val Ser Cys Lys Ala Ser Gly Asn Ser Phe Ser Asn
145                 150                 155                 160

His Asp Val His Trp Val Arg Gln Ala Thr Gly Gln Gly Leu Glu Trp
                165                 170                 175

Met Gly Trp Met Ser His Glu Gly Asp Lys Thr Gly Leu Ala Gln Lys
            180                 185                 190

Phe Gln Gly Arg Val Thr Ile Thr Arg Asp Ser Gly Ala Ser Thr Val
        195                 200                 205

Tyr Met Glu Leu Arg Gly Leu Thr Ala Asp Thr Ala Ile Tyr Tyr
    210                 215                 220

Cys Leu Thr Gly Ser Lys His Arg Leu Arg Asp Tyr Phe Leu Tyr Asn
225                 230                 235                 240

Glu Tyr Gly Pro Asn Tyr Glu Glu Trp Gly Asp Tyr Leu Ala Thr Leu
                245                 250                 255

Asp Val Trp Gly His Gly Thr Ala Val Thr Val Ser Ser
            260                 265
```

```
<210> SEQ ID NO 4
<211> LENGTH: 42
<212> TYPE: PRT
<213> ORGANISM: Artificial Sequence
<220> FEATURE:
<223> OTHER INFORMATION: 4-1BB signaling domain

<400> SEQUENCE: 4

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 5
<211> LENGTH: 112
<212> TYPE: PRT
<213> ORGANISM: Artificial Sequence
<220> FEATURE:
<223> OTHER INFORMATION: CD3-zeta signaling domain

<400> SEQUENCE: 5

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 6
<211> LENGTH: 257
<212> TYPE: PRT
<213> ORGANISM: Artificial Sequence
<220> FEATURE:
<223> OTHER INFORMATION: Homo sapiens

<400> SEQUENCE: 6

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu Arg Ser Gly Gly Gly Gly Ser
```

```
                  100                 105                 110
Gly Gly Gly Gly Ser Gly Gly Gly Ser Gln Pro Gln Leu Gln Glu
            115                 120                 125

Ser Gly Pro Thr Leu Val Glu Ala Ser Glu Thr Leu Ser Leu Thr Cys
130                 135                 140

Ala Val Ser Gly Asp Ser Thr Ala Ala Cys Asn Ser Phe Trp Gly Trp
145                 150                 155                 160

Val Arg Gln Pro Pro Gly Lys Gly Leu Glu Trp Val Gly Ser Leu Ser
                165                 170                 175

His Cys Ala Ser Tyr Trp Asn Arg Gly Trp Thr Tyr His Asn Pro Ser
            180                 185                 190

Leu Lys Ser Arg Leu Thr Leu Ala Leu Asp Thr Pro Lys Asn Leu Val
        195                 200                 205

Phe Leu Lys Leu Asn Ser Val Thr Ala Ala Asp Thr Ala Thr Tyr Tyr
    210                 215                 220

Cys Ala Arg Phe Gly Gly Glu Val Leu Arg Tyr Thr Asp Trp Pro Lys
225                 230                 235                 240

Pro Ala Trp Val Asp Leu Trp Gly Arg Gly Thr Leu Val Thr Val Ser
                245                 250                 255

Ser

<210> SEQ ID NO 7
<211> LENGTH: 263
<212> TYPE: PRT
<213> ORGANISM: Artificial Sequence
<220> FEATURE:
<223> OTHER INFORMATION: Homo sapiens

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
        35                  40                  45

Val Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu Arg Ser
            100                 105                 110

Gly Gly Gly Gly Ser Gly Gly Gly Ser Gly Gly Gly Gly Ser Gln
            115                 120                 125

Arg Leu Val Glu Ser Gly Gly Val Val Gln Pro Gly Ser Ser Leu
    130                 135                 140

Arg Leu Ser Cys Ala Ala Ser Gly Phe Asp Phe Ser Arg Gln Gly Met
145                 150                 155                 160

His Trp Val Arg Gln Ala Pro Gly Gln Gly Leu Glu Trp Val Ala Phe
                165                 170                 175

Ile Lys Tyr Asp Gly Ser Glu Lys Tyr His Ala Asp Ser Val Trp Gly
            180                 185                 190

Arg Leu Ser Ile Ser Arg Asp Asn Ser Lys Asp Thr Leu Tyr Leu Gln
        195                 200                 205
```

Met Asn Ser Leu Arg Val Glu Asp Thr Ala Thr Tyr Phe Cys Val Arg
            210                 215                 220

Glu Ala Gly Gly Pro Asp Tyr Arg Asn Gly Tyr Asn Tyr Tyr Asp Phe
225                 230                 235                 240

Tyr Asp Gly Tyr Tyr Asn Tyr His Tyr Met Asp Val Trp Gly Lys Gly
            245                 250                 255

Thr Thr Val Thr Val Ser Ser
            260

<210> SEQ ID NO 8
<211> LENGTH: 269
<212> TYPE: PRT
<213> ORGANISM: Artificial Sequence
<220> FEATURE:
<223> OTHER INFORMATION: Homo sapiens

<400> SEQUENCE: 8

Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
            20                  25                  30

Thr Gly Ala Asn Tyr Leu Ala Trp Tyr Leu Gln Arg Pro Gly Gln Thr
        35                  40                  45

Pro Arg Leu Leu Ile His Leu Ala Thr His Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ser Asp Val Gly Thr Tyr Tyr Cys Met Gln Gly
                85                  90                  95

Leu His Ser Pro Trp Thr Phe Gly Gln Gly Thr Lys Val Glu Ile Lys
            100                 105                 110

Arg Ser Gly Gly Gly Gly Ser Gly Gly Gly Gly Ser Gly Gly Gly Gly
        115                 120                 125

Ser Gln Val Gln Leu Val Gln Ser Gly Ala Glu Val Lys Lys Pro Gly
130                 135                 140

Ser Ser Val Lys Val Ser Cys Lys Ala Ser Gly Asn Ser Phe Ser Asn
145                 150                 155                 160

His Asp Val His Trp Val Arg Gln Ala Thr Gly Gln Gly Leu Glu Trp
                165                 170                 175

Met Gly Trp Met Ser His Glu Gly Asp Lys Thr Gly Leu Ala Gln Lys
            180                 185                 190

Phe Gln Gly Arg Val Thr Ile Thr Arg Asp Ser Gly Ala Ser Thr Val
        195                 200                 205

Tyr Met Glu Leu Arg Gly Leu Thr Ala Asp Thr Ala Ile Tyr Tyr
    210                 215                 220

Cys Leu Thr Gly Ser Lys His Arg Leu Arg Asp Tyr Phe Leu Tyr Asn
225                 230                 235                 240

Glu Tyr Gly Pro Asn Tyr Glu Glu Trp Gly Asp Tyr Leu Ala Thr Leu
                245                 250                 255

Asp Val Trp Gly His Gly Thr Ala Val Thr Val Ser Ser
            260                 265

<210> SEQ ID NO 9
<211> LENGTH: 42
<212> TYPE: PRT
<213> ORGANISM: Artificial Sequence
<220> FEATURE:
<223> OTHER INFORMATION: Homo sapiens

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 10
<211> LENGTH: 112
<212> TYPE: PRT
<213> ORGANISM: Artificial Sequence
<220> FEATURE:
<223> OTHER INFORMATION: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 11
<211> LENGTH: 23
<212> TYPE: PRT
<213> ORGANISM: Artificial Sequence
<220> FEATURE:
<223> OTHER INFORMATION: Homo sapiens

<400> SEQUENCE: 11

Met Cys Pro Gln Lys Leu Thr Ile Ser Trp Phe Ala Ile Val Leu Leu
1               5                   10                  15

Val Ser Pro Leu Met Ala Met
            20

<210> SEQ ID NO 12
<211> LENGTH: 69
<212> TYPE: PRT
<213> ORGANISM: Artificial Sequence
<220> FEATURE:
<223> OTHER INFORMATION: Homo sapiens

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 13
<211> LENGTH: 346
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: MND promoter
<220> FEATURE:
<221> NAME/KEY: misc_feature
<223> OTHER INFORMATION: modified moloney murine leukemic virus promoter
      with myleloproliferative sarcoma virus enhancer

<400> SEQUENCE: 13
gaacagagaa acaggagaat atgggccaaa caggatatct gtggtaagca gttcctgccc      60
cggctcaggg ccaagaacag ttggaacagc agaatatggg ccaaacagga tatctgtggt     120
aagcagttcc tgccccggct cagggccaag aacagatggc cccagatgc ggtcccgccc     180 tcagcagttt ctagagaacc atcagatgtt tccagggtgc cccaaggacc tgaaatgacc     240
ctgtgcctta tttgaactaa ccaatcagtt cgcttctcgc ttctgttcgc gcgcttctgc     300
tccccgagct ctatataagc agagctcgtt tagtgaaccg tcagat                   346

<210> SEQ ID NO 14
<211> LENGTH: 938
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Long human EF1a promoter

<400> SEQUENCE: 14
gtaagtgccg tgtgtggttc ccgcgggcct ggcctcttta cgggttatgg cccttgcgtg      60
ccttgaatta cttccactgg ctgcagtacg tgattcttga tcccgagctt cgggttggaa     120
gtgggtggga gagttcgagg ccttgcgctt aaggagcccc ttcgcctcgt gcttgagttg     180
aggcctggcc tgggcgctgg ggccgccgcg tgcgaatctg gtggcacctt cgcgcctgtc     240
tcgctgcttt cgataagtct ctagccattt aaaatttttg atgacctgct gcgacgcttt     300
ttttctggca agatagtctt gtaaatgcgg gccaagatct gcacactggt atttcggttt     360
ttggggccgc gggcggcgac ggggcccgtg cgtcccagcg cacatgttcg gcgaggcggg     420
gcctgcgagc gcggccaccg agaatcggac ggggtagtc tcaagctggc cggcctgctc     480
tggtgcctgg cctcgcgccg ccgtgtatcc cccgccctg gcggcaagg ctggcccggt     540 cggcaccagt tgcgtgagcg gaaagatggc cgcttcccgg ccctgctgca gggagctcaa     600
aatggaggac gcggcgctcg ggagagcggg cgggtgagtc acccacacaa aggaaaaggg     660
cctttccgtc ctcagccgtc gcttcatgtg actccacgga gtaccgggcg ccgtccaggc     720
acctcgatta gttctcgagc ttttggagta cgtcgtcttt aggttggggg gaggggtttt     780
atgcgatgga gtttccccac actgagtggg tggagactga agttaggcca gcttggcact     840
tgatgtaatt ctccttggaa tttgcccttt ttgagtttgg atcttggttc attctcaagc     900

```
ctcagacagt ggttcaaagt ttttttcttc catttcag                              938

<210> SEQ ID NO 15
<211> LENGTH: 231
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: short human EF1a promoter

<400> SEQUENCE: 15
aggctccggt gcccgtcagt gggcagagcg cacatcgccc acagtccccg agaagttggg       60
gggaggggtc ggcaattgaa ccggtgccta gagaaggtgg cgcggggtaa actgggaaag     120
tgatgtcgtg tactggctcc gccttttttcc cgagggtggg ggagaaccgt atataagtgc     180
agtagtcgcc gtgaacgttc tttttcgcaa cgggtttgcc gccagaacac a              231
```